United States Patent
Fischer et al.

(10) Patent No.: US 8,435,549 B2
(45) Date of Patent: May 7, 2013

(54) HALOGEN ALKOXY SPIROCYCLIC TETRAMIC AND TETRONIC ACID DERIVATIVES

(75) Inventors: Reiner Fischer, Monheim (DE); Thomas Bretschneider, Lohmar (DE); Stefan Lehr, Liederbach (DE); Christian Arnold, Langenfeld (DE); Jan Dittgen, Frankfurt (DE); Dieter Feucht, Eschborn (DE); Heinz Kehne, Hofheim (DE); Olga Malsam, Rösrath (DE); Christopher Hugh Rosinger, Hofheim (DE); Eva-Maria Franken, Limonest (FR); Ulrich Görgens, Ratingen (DE)

(73) Assignee: Bayer Cropscience AG, Monheim (DE)

( * ) Notice: Subject to any disclaimer, the term of this patent is extended or adjusted under 35 U.S.C. 154(b) by 235 days.

(21) Appl. No.: 12/679,968

(22) PCT Filed: Sep. 12, 2008

(86) PCT No.: PCT/EP2008/007517
§ 371 (c)(1),
(2), (4) Date: Jun. 30, 2010

(87) PCT Pub. No.: WO2009/039975
PCT Pub. Date: Apr. 2, 2009

(65) Prior Publication Data
US 2010/0279873 A1    Nov. 4, 2010

(30) Foreign Application Priority Data
Sep. 25, 2007    (EP) ..................... 07117104

(51) Int. Cl.
C07D 207/46    (2006.01)
C07D 491/10    (2006.01)
C07D 307/94    (2006.01)
A01P 13/00     (2006.01)

(52) U.S. Cl.
USPC ........... 424/405; 504/283; 548/408; 548/544; 549/331

(58) Field of Classification Search ............ 548/544
See application file for complete search history.

(56) References Cited

U.S. PATENT DOCUMENTS

| | | |
|---|---|---|
| 2,842,476 A | 7/1958 | Schreiber |
| 4,021,224 A | 5/1977 | Pallos et al. |
| 4,186,130 A | 1/1980 | Teach |
| 4,623,727 A | 11/1986 | Hübele |
| 4,639,266 A | 1/1987 | Heubach et al. |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,985,063 A | 1/1991 | Fischer et al. |
| 5,045,560 A | 9/1991 | Fischer et al. |
| 5,116,836 A | 5/1992 | Fischer et al. |
| 5,225,434 A | 7/1993 | Bertram et al. |
| 5,258,527 A | 11/1993 | Krauskopf et al. |
| 5,262,383 A | 11/1993 | Fischer et al. |
| 5,314,863 A | 5/1994 | Löher et al. |
| 5,380,852 A | 1/1995 | Schütze et al. |
| 5,401,700 A | 3/1995 | Sohn et al. |
| 5,462,912 A | 10/1995 | Hioki et al. |
| 5,462,913 A | 10/1995 | Fischer et al. |
| 5,504,057 A | 4/1996 | Fischer et al. |
| 5,508,436 A | 4/1996 | Fischer et al. |

(Continued)

FOREIGN PATENT DOCUMENTS

| | | |
|---|---|---|
| CA | 1 162 071 | 2/1984 |
| CA | 2 671 179 A1 | 6/2008 |

(Continued)

OTHER PUBLICATIONS

Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.*, 51:131-152, SCI, United Kingdom (1997).

Becker, H., et al., Organikum, VEB Deutscher Verlag der Wissenschaften, S.505 Berlin (1977).

Bhattacharya, B., "Isoquinoline Derivatives: Part XVIII—Formation of I-Alkyl-(or alkaryl or aryl)-3-methyl-7-chloro-(or 5-chloro)-isoquinolines," *Indian J. Chem.*, 6:341-345, Council of Scientific and Industrial Research, India (1968).

(Continued)

Primary Examiner — Shawquia Young
(74) Attorney, Agent, or Firm — Sterne, Kessler, Goldstein & Fox P.L.L.C.

(57) ABSTRACT

The invention relates to novel haloalkoxyspirocyclic tetramic and tetronic acid derivatives of the formula (I)

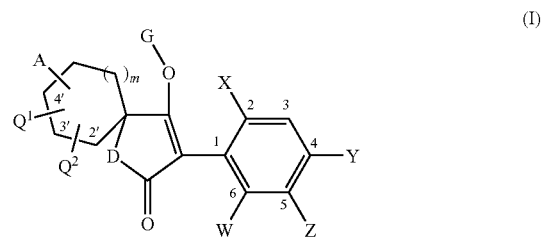

in which W, X, Y, Z, A, D, $Q^1$, $Q^2$, m and G have the meanings given above,
to a plurality of processes and intermediates for their preparation, and to their use as pesticides and/or herbicides.
Moreover, the invention provides selective herbicidal compositions comprising, firstly, haloalkoxyspirocyclic tetramic and tetronic acid derivatives and, secondly, a crop plant compatibility-improving compound.
The invention furthermore relates to increasing the action of crop protection compositions comprising compounds of the formula (I) through the addition of ammonium salts or phosphonium salts and optionally penetrants.

19 Claims, No Drawings

U.S. PATENT DOCUMENTS

| | | | |
|---|---|---|---|
| 5,516,750 A | 5/1996 | Willms et al. | |
| 5,538,937 A | 7/1996 | Hasebe et al. | |
| 5,567,671 A | 10/1996 | Fischer et al. | |
| 5,589,469 A | 12/1996 | Fischer et al. | |
| 5,610,122 A | 3/1997 | Fischer et al. | |
| 5,622,917 A | 4/1997 | Fischer et al. | |
| 5,672,718 A | 9/1997 | Fischer et al. | |
| 5,683,965 A | 11/1997 | Bachmann et al. | |
| 5,700,758 A | 12/1997 | Rösch et al. | |
| 5,705,476 A | 1/1998 | Hoffarth | |
| 5,739,079 A | 4/1998 | Holdgrün et al. | |
| 5,792,755 A | 8/1998 | Sagenmüller et al. | |
| 5,811,374 A | 9/1998 | Bertram et al. | |
| 5,830,825 A | 11/1998 | Fischer et al. | |
| 5,830,826 A | 11/1998 | Fischer et al. | |
| 5,994,274 A | 11/1999 | Fischer et al. | |
| 6,114,374 A | 9/2000 | Lieb et al. | |
| 6,133,296 A | 10/2000 | Lieb et al. | |
| 6,140,358 A | 10/2000 | Lieb et al. | |
| 6,200,932 B1 | 3/2001 | Fischer et al. | |
| 6,235,680 B1 | 5/2001 | Ziemer et al. | |
| 6,251,827 B1 | 6/2001 | Ziemer et al. | |
| 6,288,102 B1 | 9/2001 | Hagemann et al. | |
| 6,316,486 B1 | 11/2001 | Lieb et al. | |
| 6,358,887 B1 | 3/2002 | Fischer et al. | |
| 6,451,843 B1 | 9/2002 | Lieb et al. | |
| 6,458,965 B1 | 10/2002 | Lieb et al. | |
| 6,472,419 B1 | 10/2002 | Fischer et al. | |
| 6,511,940 B1 | 1/2003 | Ziemer et al. | |
| 6,589,976 B1 | 7/2003 | Fischer et al. | |
| 6,602,823 B1 | 8/2003 | Röchling et al. | |
| 6,608,211 B1 | 8/2003 | Hagemann et al. | |
| 6,645,914 B1 | 11/2003 | Woznica et al. | |
| 6,861,391 B1 | 3/2005 | Fischer et al. | |
| 6,894,005 B1 | 5/2005 | Maetzke et al. | |
| 7,727,933 B2 | 6/2010 | Fischer et al. | |
| 2002/0188136 A1* | 12/2002 | Lieb et al. | 548/368.4 |
| 2003/0171219 A1 | 9/2003 | Lieb et al. | |
| 2003/0216260 A1 | 11/2003 | Ruther et al. | |
| 2003/0224939 A1 | 12/2003 | Miles | |
| 2005/0009880 A1 | 1/2005 | Cottrell et al. | |
| 2005/0054535 A1 | 3/2005 | Fischer et al. | |
| 2005/0096386 A1 | 5/2005 | Cottrell et al. | |
| 2006/0160847 A1 | 7/2006 | Fischer et al. | |
| 2006/0166829 A1 | 7/2006 | Fischer et al. | |
| 2007/0015664 A1 | 1/2007 | Fischer et al. | |
| 2007/0032539 A1 | 2/2007 | Himmler | |
| 2007/0129252 A1 | 6/2007 | Fischer et al. | |
| 2007/0225167 A1 | 9/2007 | Fischer et al. | |
| 2007/0225170 A1 | 9/2007 | Fischer et al. | |
| 2007/0244007 A1 | 10/2007 | Fischer et al. | |
| 2007/0275858 A1 | 11/2007 | Fischer et al. | |
| 2007/0298968 A1 | 12/2007 | Bretschneider et al. | |
| 2007/0298969 A1 | 12/2007 | Fischer et al. | |
| 2008/0081807 A1 | 4/2008 | Lieb et al. | |
| 2008/0167188 A1 | 7/2008 | Fischer et al. | |
| 2008/0220973 A1 | 9/2008 | Fischer et al. | |
| 2008/0305955 A1 | 12/2008 | Bretschneider et al. | |
| 2008/0318776 A1 | 12/2008 | Fischer et al. | |
| 2009/0029858 A1 | 1/2009 | Fischer et al. | |
| 2009/0209513 A1 | 8/2009 | Fischer et al. | |
| 2009/0215624 A1 | 8/2009 | Fischer et al. | |
| 2009/0227563 A1 | 9/2009 | Fischer et al. | |
| 2009/0239906 A1 | 9/2009 | Fischer et al. | |
| 2009/0298828 A1 | 12/2009 | Fischer et al. | |
| 2009/0305891 A1 | 12/2009 | Fischer et al. | |
| 2010/0004127 A1 | 1/2010 | Fischer et al. | |
| 2010/0009850 A1 | 1/2010 | Fischer et al. | |

FOREIGN PATENT DOCUMENTS

| | | |
|---|---|---|
| DE | 10 2005 059 892 A1 | 6/2007 |
| EP | 0 262 399 A2 | 4/1988 |
| EP | 0 346 620 A1 | 5/1989 |
| EP | 0 453 086 A2 | 10/1991 |
| EP | 0 613 618 A1 | 9/1994 |
| GB | 2 266 888 A | 11/1993 |
| JP | 2000-053670 | 2/2000 |
| JP | 2002-205984 | 7/2002 |
| WO | WO 92/16108 A1 | 10/1992 |
| WO | WO 95/01971 A1 | 1/1995 |
| WO | WO 95/17817 A1 | 7/1995 |
| WO | WO 98/35553 A1 | 8/1998 |
| WO | WO 03/059065 A1 | 7/2003 |
| WO | WO 03/062244 A1 | 7/2003 |
| WO | WO 2008/067873 A1 | 6/2008 |
| WO | WO 2008/067910 A1 | 6/2008 |

OTHER PUBLICATIONS

Harrison, H.R., et al., "Use of molecular sieves in the methyl esterification of carboxylic acids," *Chem. Ind.*, p. 1568, Society of Chemical Industry, United Kingdom (1968).

Compagnon, P.L. & Miocque, M., "Addition des Réactifs Nucléophiles sur la Triple Liaison Nitrile I.—Addition des Hydrures, de L'eau, de L'hydrogéne Sulfuré et de L'hydrogéne Sélénié," *Ann. Chim.*, 5:11-22, Wiley Interscience, France (1970).

Edward, J.T. & Jitrangsri, C., "Stereochemistry of the Bucherer-Bergs and Strecker Reactions of 4-*tert*-Butylcyclohexanone," *Can. J. Chem.*, 53:3339, NRC Research Press, United States (1975).

Ito, M., et al., "Synthesis and Insecticidal Activity of Novel *N*-Oxydihydropyrrole Derivatives with a Substituted Spirocyclohexyl Group," *Biosci. Biotechnol. Biochem.*, 67:1230-1238, Japan Society for Bioscience, Biotechnology, and Agrochemistry, Japan (2003).

Munday, L., "Amino-acids of the Cyclohexane Series. Part I.," *J. Chem. Soc.*, p. 4372, Royal Society of Chemistry, United Kingdom (1961).

Schmierer, R., and Mildenberger, H., "Cyclisierung von *N*-Acylalanin- und *N*-Acylglycinestern," *Liebigs Ann. Chem.*, 6:1095-1098, VCH Verlagsgesellschaft mbH, Germany (1985).

Sonntag, N.O.V., "The Reactions of Aliphatic Acid Chlorides," *Chem. Reviews*, 52:237-416, American Chemical Society, United States (1952).

Suzuki, S., et al., "Studies on Antiviral Agents. IV. Biological Activity of Tenuazonic Acid Derivatives," *Chem. Pharm. Bull.*, 15:1120-1122, Pharmaceutical Society of Japan, Japan (1967).

English language abstract of European Patent Publication No. EP 0 346 620 A1 (1989).

English language abstract of German Patent Publication No. DE 10 2005 059 892 A1 (2007).

English language abstract of Japanese Patent Publication No. 2000-053670 (2000).

English language abstract of Japanese Patent Publication No. 2002-205984 (2002).

International Search Report of International Application No. PCT/EP2008/007517, European Patent Office, Netherlands, mailed Mar. 11, 2009.

English language translation of NPL5.

English language translation of NPL9.

\* cited by examiner

HALOGEN ALKOXY SPIROCYCLIC TETRAMIC AND TETRONIC ACID DERIVATIVES

The present invention relates to novel haloalkoxyspirocyclic tetramic and tetronic acid derivatives, to a plurality of processes for their preparation and to their use as pesticides and/or herbicides. The invention also provides selective herbicidal compositions comprising, firstly, haloalkoxyspirocyclic tetramic and tetronic acid derivatives and, secondly, a crop plant compatibility-improving compound.

The present invention furthermore relates to increasing the action of crop protection compositions comprising, in particular, haloalkoxyspirocyclic tetramic and tetronic acid derivatives, through the addition of ammonium salts or phosphonium salts and optionally penetrants, to the corresponding compositions, to processes for producing them and to their application in crop protection as insecticides and/or acaricides and/or for preventing unwanted vegetation.

Pharmaceutical properties of 3-acyl-pyrrolidine-2,4-diones have already been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones) of which, however, no herbicidal, insecticidal or acaricidal activity has become known. Unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (EP-A-377 893 and EP-A-442 077) are known to have herbicidal, insecticidal or acaricidal activity.

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869 and WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049596, WO 05/066125, WO 05/092897, WO 06/000355, WO 06/029799, WO 06/056281, WO 06/056282, WO 06/089633, WO 07/048,545, WO 07/073,856, DE-A-2005/059892, WO 07/096,058, WO 07/121,868, WO 07/140, 881, WO 08/067,873, WO 08/067,910 and WO 08/067,911. Furthermore known are ketal-substituted 1H-arylpyrrolidine-2,4-diones from WO 99/16748 and (spiro)-ketal-substituted N-alkoxyalkoxy-substituted arylpyrrolidinediones from JP-A-14 205 984 and Ito M. et. al., Bioscience, Biotechnology and Biochemistry 67, 1230-1238, (2003). The addition of safeners to ketoenols is also known in principle from WO 03/013249. Moreover, WO 06/024411 discloses herbicidal compositions comprising ketoenols.

It is known that certain $\Delta^3$-dihydrofuran-2-one derivatives have herbicidal, insecticidal or acaricidal properties: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 06/089633, WO 07/048,545 and WO 07/073,856 and WO 08/067,911.

However, the herbicidal and/or acaricidal and/or insecticidal activity and/or activity spectrum and/or the plant compatibility of the known compounds, in particular with respect to crop plants, is/are not always satisfactory.

This invention, accordingly, provides novel compounds of the formula (I)

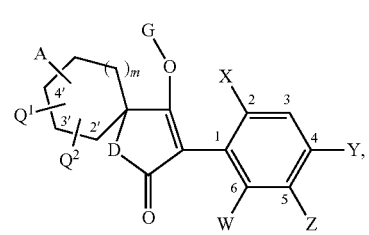

(I)

in which
W represents hydrogen, alkyl, alkenyl, alkynyl, optionally substituted cycloalkyl, halogen, alkoxy, alkenyloxy, haloalkyl, haloalkoxy or cyano,
X represents halogen, alkyl, alkenyl, alkynyl, optionally substituted cycloalkyl, alkoxy, alkenyloxy, alkylthio, alkylsulfinyl, alkylsulfonyl, haloalkyl, haloalkoxy, haloalkenyloxy, nitro or cyano,
Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl,
A represents haloalkoxy or halocycloalkylalkoxy,
D represents NH or oxygen,
$Q^1$, $Q^2$ independently of one another represent hydrogen, alkyl, haloalkyl or alkoxy,
m represents the number 0 or 1,
G represents hydrogen (a) or one of the groups

(b)

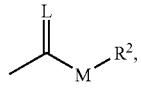

(c)

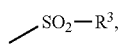

(d)

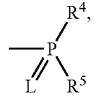

(e)

E, or (f)

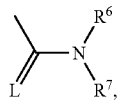 

(g)

in which
E represents a metal ion or an ammonium ion,
L represents oxygen or sulfur, M represents oxygen or sulfur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, in each case optionally halogen- or cyano-substituted alkyl, cycloalkyl, alkenyl, alkoxy, alkoxyalkyl, in each case optionally substituted phenyl or benzyl, or together with the N atom to which they are attached form an optionally substituted cycle which optionally contains oxygen or sulfur.

Depending, inter alia, on the nature of the substituents, the compounds of the formula (I) can be present as optical isomers or mixtures of isomers in varying compositions, which can be separated, if desired, in a customary manner. The present invention provides both the pure isomers and the isomer mixtures, their preparation and use and compositions comprising them. However, the following text will, for the sake of simplicity, always mention compounds of the formula (I), even though this is understood as meaning not only the pure compounds, but also, if appropriate, mixtures with various amounts of isomeric compounds.

Taking D to be NH (1) and D to be O (2), the following main structures (I-1) to (I-2) result:

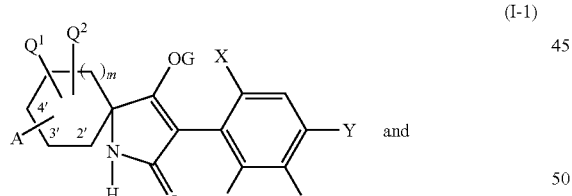

(I-1)

and

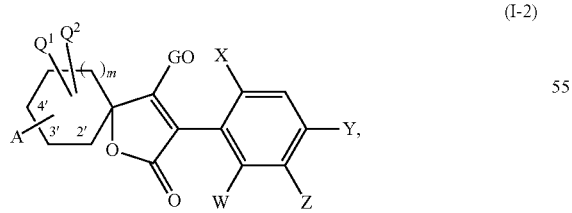

(I-2)

in which
A, G, $Q^1$, $Q^2$, m, W, X, Y and Z have the meaning given above.

Taking into consideration the various meanings (a), (b), (c), (d), (e), (f) and (g) of group G, the following main structures (I-1-a) to (I-1-g) result if D is NH (1),

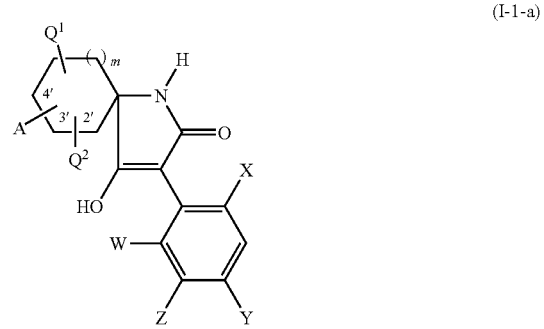

(I-1-a)

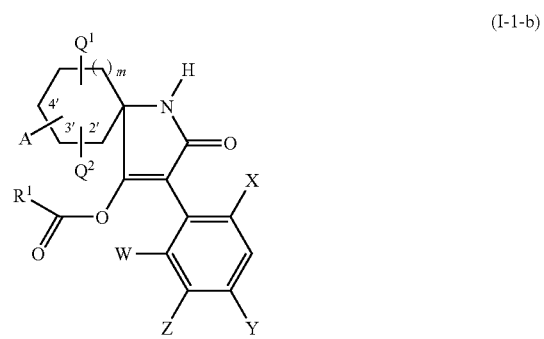

(I-1-b)

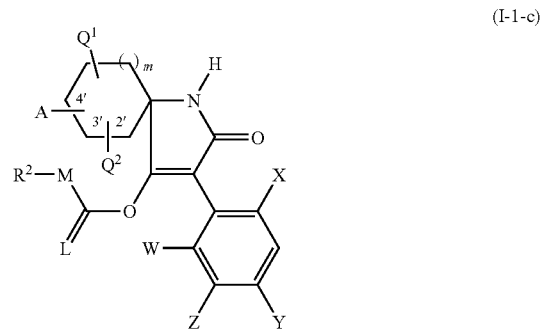

(I-1-c)

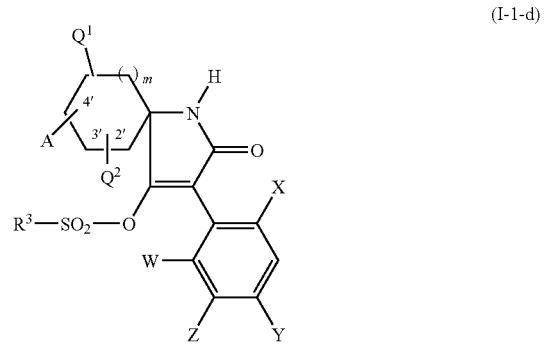

(I-1-d)

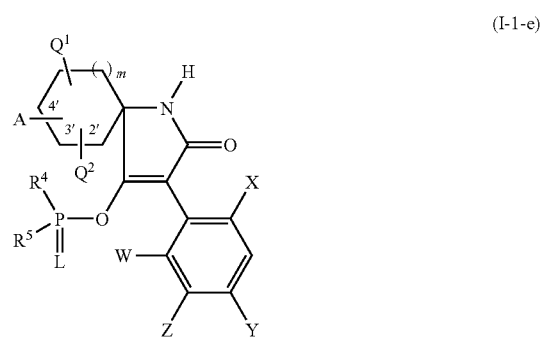

(I-1-e)

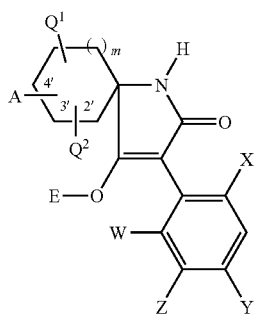
(I-1-f)

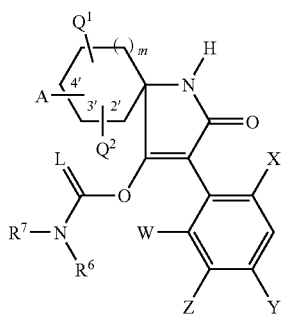
(I-1-g)

in which
A, E, L, M, $Q^1$, $Q^2$, m, W, X, Y, Z, $R^1$, $R^2$, $R^3$, $R^4$, $R^5$, $R^6$ and $R^7$ have the meanings given above.

Taking into consideration the various meanings (a), (b), (c), (d), (e), (f) and (g) of group G, the following main structures (I-2-a) to (I-2-g) result if D is O (2),

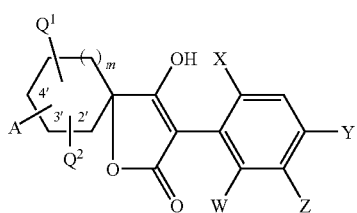
(I-2-a)

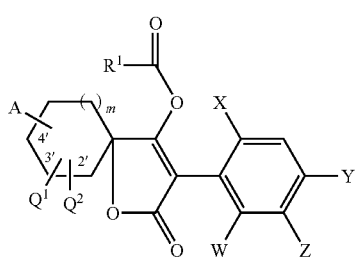
(I-2-b)

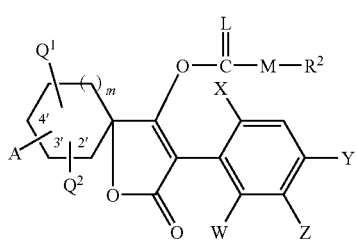
(I-2-c)

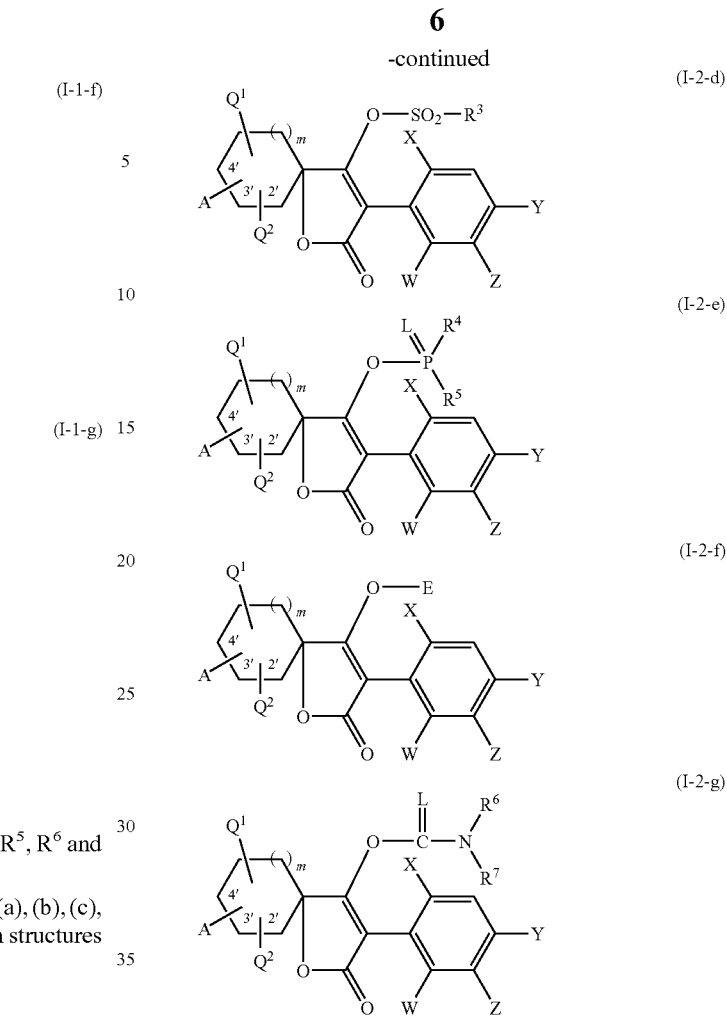

in which
A, E, L, M, $Q^1$, $Q^2$, m, W, X, Y, Z, $R^1$, $R^2$, $R^3$, $R^4$, $R^5$, $R^6$ and $R^7$ have the meaning given above.

Furthermore, it has been found that the novel compounds of the formula (I) are obtained by the process described below:

(A) Compounds of the formula (I-1-a)

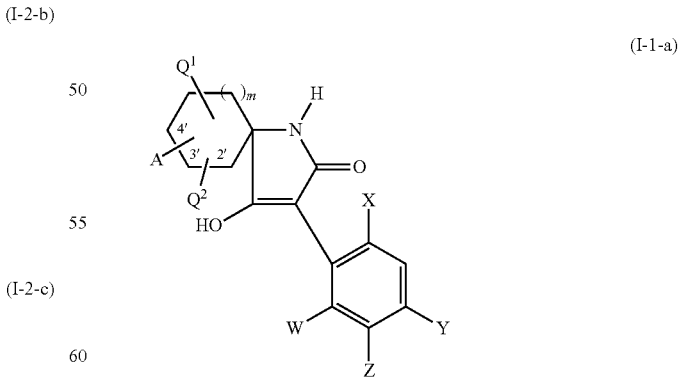
(I-1-a)

in which
A, $Q^1$, $Q^2$, m, W, X, Y and Z have the meanings given above,
are obtained when
compounds of the formula (II)

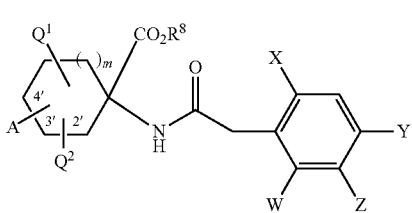

(II)

in which

A, $Q^1$, $Q^2$, m, W, X, Y and Z have the meanings given above, and $R^8$ represents alkyl (preferably $C_1$-$C_6$-alkyl)

are subjected to an intramolecular condensation reaction in the presence of a diluent and in the presence of a base.

(B) Furthermore, it has been found that compounds of the formula (I-2-a)

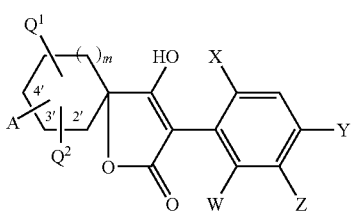

(I-2-a)

in which

A, $Q^1$, $Q^2$, m, W, X, Y and Z have the meanings given above, are obtained when compounds of the formula (III)

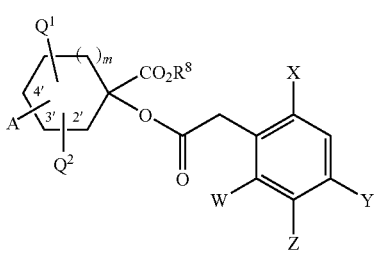

(III)

in which

A, $Q^1$, $Q^2$, m, W, X, Y, Z and $R^8$ have the meanings given above, are subjected to an intramolecular condensation reaction in the presence of a diluent and in the presence of a base.

Moreover, it has been found (C) that the compounds of the formulae (I-1-b) to (I-2-b) shown above in which $R^1$, A, $Q^1$, $Q^2$, m, W, X, Y and Z have the meanings given above are obtained when compounds of the formulae (I-1-a) to (I-2-a) shown above in which A, $Q^1$, $Q^2$, m, W, X, Y and Z have the meanings given above are in each case α) reacted with compounds of the formula (IV)

(IV)

in which $R^1$ is as defined above and

Hal represents halogen (in particular chlorine or bromine)

or

β) with carboxylic anhydrides of the formula (V)

$R^1$—CO—O—CO—$R^1$ (V)

in which $R^1$ has the meaning given above, if appropriate in the presence of a diluent and if appropriate in the presence of an acid binder;

(D) that the compounds of the formulae (I-1-c) to (I-2-c) shown above in which $R^2$, A, $Q^1$, $Q^2$, m, W, M, X, Y and Z have the meanings given above and L represents oxygen are obtained when compounds of the formulae (I-1-a) to (I-2-a) shown above in which A, $Q^1$, $Q^2$, m, W, X, Y and Z have the meanings given above are in each case reacted with chloroformic esters or chloroformic thioesters of the formula (VI)

$R^2$-M—CO—Cl (VI)

in which $R^2$ and M have the meanings given above, if appropriate in the presence of a diluent and if appropriate in the presence of an acid binder;

(E) that compounds of the formulae (I-1-c) to (I-2-c) shown above in which $R^2$, A, $Q^1$, $Q^2$, m, W, M, X, Y and Z have the meanings given above and L represents sulfur are obtained when compounds of the formulae (I-1-a) to (I-2-a) shown above in which A, $Q^1$, $Q^2$, m, W, X, Y and Z have the meanings given above are in each case reacted with chloromonothioformic esters or chlorodithioformic esters of the formula (VII)

(VII)

in which

M and $R^2$ have the meanings given above, if appropriate in the presence of a diluent and if appropriate in the presence of an acid binder, (F) that compounds of the formulae (I-1-d) to (I-2-d) shown above in which $R^3$, A, W, $Q^1$, $Q^2$, m, X, Y and Z have the meanings given above are obtained when compounds of the formulae (I-1-a) shown above to (I-2-a) shown above in which A, B, $Q^1$, $Q^2$, m, W, X, Y and Z have the meanings given above are in each case reacted with sulfonyl chlorides of the formula (VIII)

$R^3$—$SO_2$—Cl (VIII)

in which $R^3$ has the meaning given above, if appropriate in the presence of a diluent and if appropriate in the presence of an acid binder, (G) that compounds of the formulae (I-1-e) to (I-2-e) shown above in which L, $R^4$, $R^5$, A, $Q^1$, $Q^2$, m, W, X, Y and Z have the meanings given above are obtained when compounds of the formulae (I-1-a) to (I-2-a) shown above in which A, $Q^1$, $Q^2$, m, W, X, Y and Z have the meanings given above are in each case
reacted with phosphorus compounds of the formula (IX)

$$\text{Hal-P}\overset{R^4}{\underset{\underset{L}{\parallel}}{\diagdown R^5}} \quad (IX)$$

in which
L, $R^4$ and $R^5$ are as defined above and
Hal represents halogen (in particular chlorine or bromine),
if appropriate in the presence of a diluent and if appropriate in the presence of an acid binder,
(H) that compounds of the formulae (I-1-f) to (I-2-f) shown above in which E, A, $Q^1$, $Q^2$, m, W, X, Y and Z have the meanings given above are obtained when compounds of the formulae (I-1-a) to (I-2-a) in which A, $Q^1$, $Q^2$, m, W, X, Y and Z have the meanings given above are in each case reacted with metal compounds or amines of the formulae (X) or (XI)

$$\text{Me(OR}^{10})_t \quad (X)$$

$$R^{10}\underset{\underset{R^{12}}{|}}{\diagdown N \diagup} R^{11} \quad (XI)$$

in which
Me represents a monovalent or divalent metal (preferably an alkali metal or alkaline earth metal such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl)
if appropriate in the presence of a diluent,
(I) that compounds of the formulae (I-1-g) to (I-2-g) shown above in which L, $R^6$, $R^7$, A, $Q^1$, $Q^2$, m, W, X, Y and Z have the meanings given above are obtained when compounds of the formulae (I-1-a) to (I-2-a) shown above in which A, $Q^1$, $Q^2$, m, W, X, Y and Z have the meanings given above are in each case
α) reacted with isocyanates or isothiocyanates of the formula (XII)

$$R^6\text{—N}=C=L \quad (XII)$$

in which
$R^6$ and L are as defined above,
if appropriate in the presence of a diluent and if appropriate in the presence of a catalyst, or
β) reacted with carbamoyl chlorides or thiocarbamoyl chlorides of the formula (XIII)

$$R^6\underset{R^7}{\diagdown}N\diagdown\overset{\overset{L}{\parallel}}{C}\diagdown Cl \quad (XIII)$$

in which
L, $R^6$ and $R^7$ are as defined above,
if appropriate in the presence of a diluent and if appropriate in the presence of an acid binder,
(Jα) that compounds of the formulae (I-1-a) to (I-1-g) shown above in which A, D, G, $Q^1$, $Q^2$, m, W, X, Y and Z have the meaning given above are obtained when compounds of the formulae (I-1-a') to (I-2-g') in which A, D, G, $Q^1$, $Q^2$, m, W, X and Y have the meaning given above and Z' preferably represents bromine or iodine (I-1-a' to I-2-g')

and
(Jβ) that compounds of the formulae (I-1-a) to (I-2-g) shown above in which A, D, G, $Q^1$, $Q^2$, m, W, X, Y and Z have the meaning given above are obtained when compounds of the formulae (I-1-a") to (I-2-g") in which A, D, G, $Q^1$, $Q^2$, m, W, X and Z have the meaning given above and Y' preferably represents bromine or iodine (I-1-a" to I-2-g")

are coupled with (het)aryl derivatives capable of coupling, for example phenylboronic acids of the formulae (XVα) and (XVβ)

$$Z\text{—B}\overset{OH}{\diagdown OH} \quad (XV\alpha)$$

$$Y\text{—B}\overset{OH}{\diagdown OH} \quad (XV\beta)$$

or esters thereof, in the presence of a solvent, in the presence of a catalyst (for example Pd salts or Pd complexes) and in the presence of a base (for example sodium carbonate, potassium phosphate). Some of the compounds of the formula (XV) are known, some are commercially available or can be prepared by processes known in principle.

Furthermore, it has been found that the novel compounds of the formula (I) are very effective as pesticides, preferably as insecticides and/or acaricides and/or herbicides, and additionally are frequently tolerated very well by plants, in particular by crop plants.

Surprisingly, it has now also been found that certain haloalkoxyspirocyclic tetramic and tetronic acid derivatives, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in corn, soybeans and rice.

The invention also provides selective herbicidal compositions comprising an effective amount of an active compound combination comprising, as components, (a') at least one compound of the formula (I) in which A, D, G, $Q^1$, $Q^2$, m, W, X, Y and Z have the meaning given above and (b) at least one crop plant compatibility-improving compound from the following group of compounds:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulfonylbenzene, 1-[4-(N-2-methoxybenzoylsulfamoyl)phenyl]-3-methylurea (also known as N-(2-methoxybenzoyl)-4-[(methylaminocarbonyl)amino]benzenesulfonamide), 1-[4-(N-2-methoxybenzoylsulfamoyl)-phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclo-propylaminocarbonyl)benzenesulfonamide, and/or one of the following compounds, defined by general formulae, of the general formula (IIa)

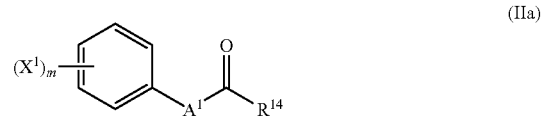

or of the general formula (IIb)

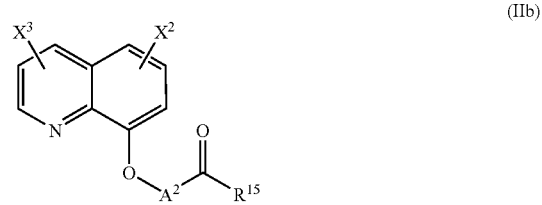

or of the formula (IIc)

where m represents a number 0, 1, 2, 3, 4 or 5, $A^1$ represents one of the divalent heterocyclic groupings shown below,

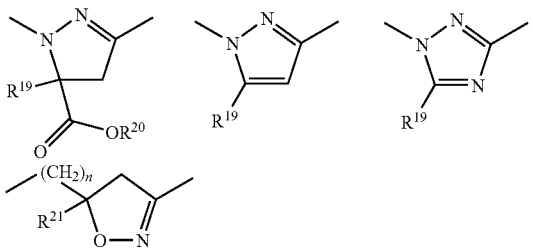

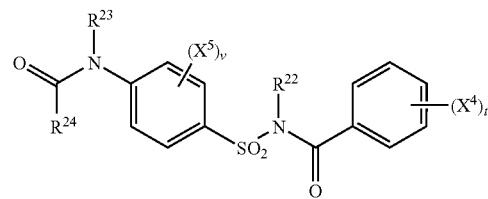

(IId)

or of the general formula (IIe)

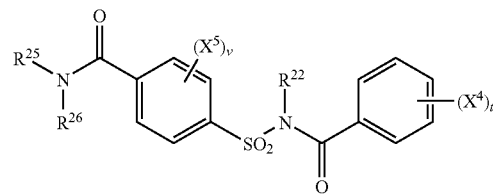

(IIe)

n represents a number 0, 1, 2, 3, 4 or 5, $A^2$ represents optionally $C_1$-$C_4$-alkyl- and/or $C_1$-$C_4$-alkoxycarbonyl- and/or $C_1$-$C_4$-alkenyloxycarbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$ haloalkyl, $C_1$-$C_4$-alkoxy or $C_1$-$C_4$-haloalkoxy.

The formula (I) provides a general definition of the compounds according to the invention. Preferred substituents or ranges of the radicals given in the formulae shown above and below are illustrated below:

W preferably represents hydrogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents halogen, $C_1$-$C_6$-alkoxy, $C_1$-$C_4$-haloalkyl, $C_1$-$C_4$-haloalkoxy or cyano, X preferably represents halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulfinyl, $C_1$-$C_6$-alkylsulfonyl, $C_1$-$C_6$-haloalkoxy, $C_3$-$C_6$-haloalkenyloxy, nitro or cyano, Y and Z independently of one another preferably represent hydrogen, halogen, $C_1$-$C_6$-alkyl, $C_2$-$C_6$-alkenyl, $C_2$-$C_6$-alkynyl, represent $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represent $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or represent one of the (het)aryl radicals

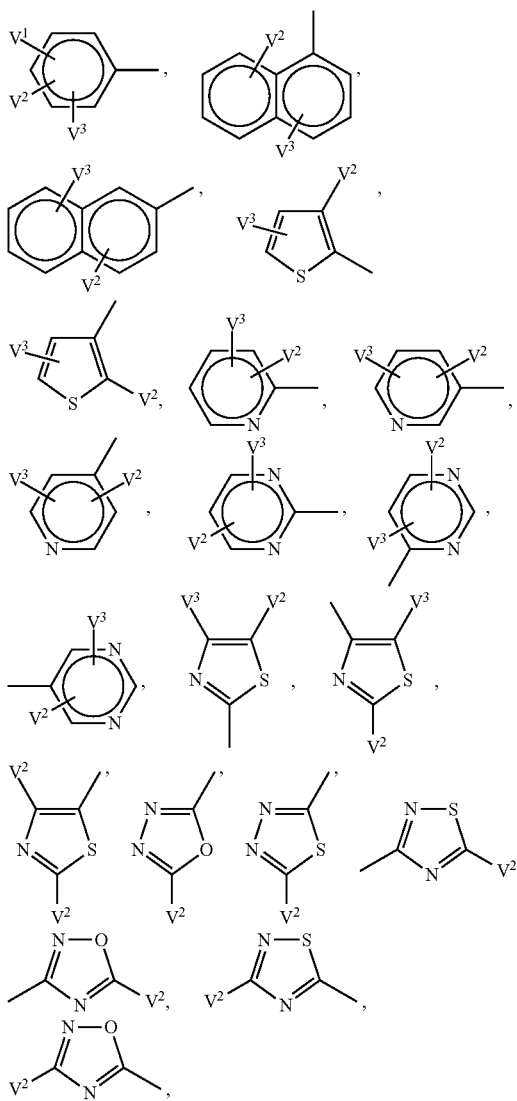

where in the case of (het)aryl only one of the radicals Y or Z may represent (het)aryl, $V^1$ preferably represents hydrogen, halogen, $C_1$-$C_{12}$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_1$-$C_4$-haloalkyl, $C_1$-$C_4$-haloalkoxy, nitro, cyano, or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally monosubstituted or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, A preferably represents $C_1$-$C_4$-alkoxy which is mono- to heptasubstituted by fluorine, chlorine, bromine and/or iodine or represents $C_3$-$C_6$-cycloalkyl-$C_1$-$C_2$-alkoxy which is mono- to pentasubstituted by fluorine, chlorine and/or bromine and which may optionally be substituted by $C_1$-$C_2$-alkyl, $C_1$-$C_2$-haloalkyl or $C_1$-$C_2$-alkoxy, D preferably represents NH (1) or oxygen (2), $Q^1$ and $Q^2$ independently of one another preferably represent hydrogen, $C_1$-$C_6$-alkyl, $C_1$-$C_2$-haloalkyl or $C_1$-$C_4$-alkoxy, m preferably represents the number 0 or 1, G preferably represents hydrogen (a) or represents one of the groups

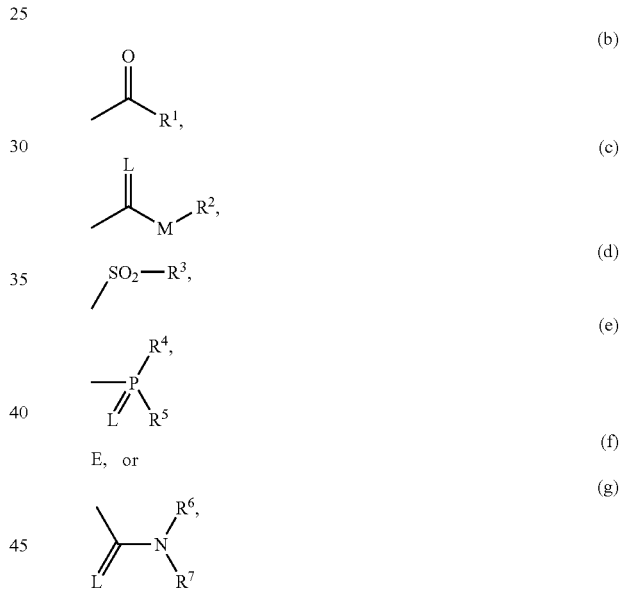

in which

E represents a metal ion or an ammonium ion,

L represents oxygen or sulfur and

M represents oxygen or sulfur, $R^1$ preferably represents in each case optionally halogen- or cyano-substituted $C_1$-$C_{20}$ alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulfur, represents phenyl which is optionally substituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio or $C_1$-$C_6$-alkylsulfonyl, represents phenyl-$C_1$-$C_6$-alkyl which is optionally substituted by halogen, nitro, cyano, $C_1$-$C_6$-alkyl, $C_1$-$C_6$-alkoxy, $C_1$-$C_6$-haloalkyl or $C_1$-$C_6$-haloalkoxy, represents optionally halogen- or $C_1$-$C_6$-alkyl-substituted 5- or 6-membered hetaryl having one or two heteroatoms from the group consisting of oxygen, sulfur and nitrogen, represents phenoxy-$C_1$-$C_6$-alkyl which is optionally substituted by halogen or $C_1$-$C_6$-alkyl, represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulfur and nitrogen.

$R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents $C_3$-$C_8$-cycloalkyl which is optionally substituted by halogen, $C_1$-$C_6$-alkyl or $C_1$-$C_6$-alkoxy, represents phenyl or benzyl, each of which is optionally substituted by halogen, cyano, nitro, $C_1$-$C_6$-alkyl, $C_1$-$C_6$-alkoxy, $C_1$-$C_6$-haloalkyl or $C_1$-$C_6$-halogenalkoxy, $R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl.

$R^4$ and $R^5$ independently of one another preferably represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulfur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_1$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_2$-haloalkyl or $C_1$-$C_2$-haloalkoxy, X particularly preferably represents chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_4$-haloalkyl, $C_1$-$C_4$-haloalkoxy or cyano, Y and Z independently of one another particularly preferably represent hydrogen, fluorine, chlorine, bromine, $C_1$-$C_4$-alkyl, $C_2$-$C_4$-alkenyl, $C_2$-$C_4$-alkynyl, represent $C_3$-$C_6$-cycloalkyl which is optionally monosubstituted by methyl, ethyl, methoxy, fluorine, chlorine, trifluoromethyl or cyclopropyl, represents $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or one of the (het)aryl radicals,

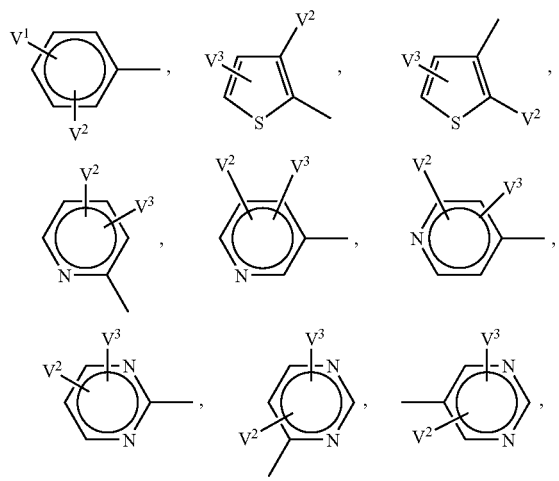

where in the case of (het)aryl only one of the radicals Y or Z may represent (het)aryl, $V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or represents phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A particularly preferably represents $C_1$-$C_4$-alkoxy which is mono- to pentasubstituted by fluorine, chlorine and/or bromine or represents $C_3$-$C_6$-cycloalkyl-$C_1$-$C_2$-alkoxy which is mono- to trisubstituted by fluorine and/or chlorine, D particularly preferably represents NH (1) or oxygen (2), $Q^1$ and $Q^2$ independently of one another particularly preferably represent hydrogen, methyl, ethyl, trifluoromethyl, methoxy or ethoxy, m particularly preferably represents the number 0 or 1, G particularly preferably represents hydrogen (a) or represents one of the groups

(b)

(c)

(d)

(e)

E, or
(f)

-continued

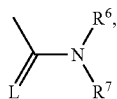
(g)

in which
E represents a metal ion or an ammonium ion,
L represents oxygen or sulfur and
M represents oxygen or sulfur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulfur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulfonyl, represents phenyl-$C_1$-$C_4$-alkyl which is optionally mono- or disubstituted by fluorine, chlorine, bromine, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine, or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulfur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, vinyl, ethynyl, propynyl, cyclopropyl, methoxy, ethoxy or trifluoromethyl, X very particularly preferably represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another very particularly preferably represent hydrogen, fluorine, chlorine, bromine, methyl, ethyl, vinyl, ethynyl, propynyl, cyclopropyl, methoxy, trifluoromethyl, trifluoromethoxy, cyano or a phenyl radical,

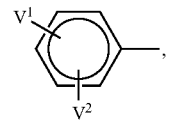

where in the case of phenyl only one of the radicals Y or Z may represent phenyl, $V^1$ very particularly preferably represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ very particularly preferably represents hydrogen, fluorine, chlorine, methyl, ethyl, n-propyl, isopropyl, methoxy, ethoxy or trifluoromethyl, A very particularly preferably represents methoxy, ethoxy, propoxy, butoxy or isobutoxy, each of which is mono- to trisubstituted by fluorine and/or chlorine, or represents cyclopropylmethoxy or cyclopropylethoxy, each of which is mono- to trisubstituted by fluorine and/or chlorine, D very particularly preferably represents NH (1) or oxygen (2), $Q^1$ and $Q^2$ very particularly preferably represent hydrogen, m very particularly preferably represents the number 1

G very particularly preferably represents hydrogen (a) or represents one of the groups

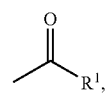
(b)

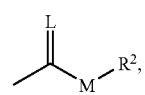
(c)

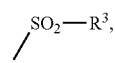
(d)

-continued

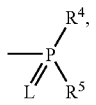
E, or

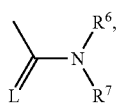

in which
E represents a metal ion or an ammonium ion,
L represents oxygen or sulfur and
M represents oxygen or sulfur,
$R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy,
represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy,
represents furanyl, thienyl or pyridyl, each of which is optionally monosubstituted by chlorine, bromine or methyl,
$R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine,
represents cyclopentyl or cyclohexyl
or represents phenyl or benzyl, each of which is optionally mono- or disubstituted by fluorine, chlorine, cyano, nitro, methyl, ethyl, methoxy, trifluoromethyl or trifluoromethoxy,
$R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro,
$R^4$ and $R^5$ independently of one another very particularly preferably represent $C_1$-$C_4$-alkoxy or $C_1$-$C_4$-alkylthio, or represent phenyl, phenoxy or phenylthio, each of which is optionally monosubstituted by fluorine, chlorine, bromine, nitro, cyano, methyl, methoxy, trifluoromethyl or trifluoromethoxy,
$R^6$ and $R^7$ independently of one another very particularly preferably represent hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulfur.
W especially preferably represents hydrogen, chlorine, bromine, methyl, ethyl or methoxy, (particularly hydrogen, methyl or ethyl),
X especially preferably represents chlorine, bromine, methyl, ethyl, methoxy or ethoxy, Y and Z independently of one another especially preferably represent hydrogen, chlorine, bromine, methyl, methoxy, cyclopropyl or the radicals

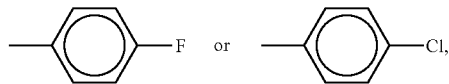

where in this case only one of the radicals Y or Z may represent a substituted phenyl radical, (Z particularly represents hydrogen, methyl, 4-Cl-phenyl or 4-F-phenyl)
A especially preferably represents methoxy, ethoxy or propoxy, each of which is mono- to trisubstituted by fluorine and/or chlorine (in particular $OCH_2CF_3$ or $OCH_2CF_2CF_3$),
D especially preferably represents NH (1) or oxygen (2),
$Q^1$ and $Q^2$ especially preferably represent hydrogen,
m especially preferably represents the number 1,
G especially preferably represents hydrogen (a) or one of the groups

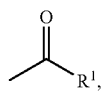

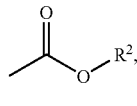

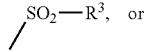

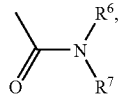

(in particular group a, b or c),
$R^1$ especially preferably represents $C_1$-$C_{10}$-alkyl, $C_1$-$C_4$-alkoxy-$C_1$-$C_2$-alkyl, $C_3$-$C_6$-cycloalkyl,
represents phenyl which is optionally monosubstituted by chlorine, or represents thienyl, (in particular $C_1$-$C_{10}$-alkyl),
$R^2$ especially preferably represents $C_1$-$C_{10}$-alkyl, $C_2$-$C_{10}$-alkenyl, or benzyl, (in particular $C_1$-$C_{10}$-alkyl),
$R^3$ especially preferably represents methyl,
$R^6$ and $R^7$ together especially preferably represent a $C_5$-$C_6$-alkylene radical in which optionally one methylene group is replaced by oxygen or sulfur.

The abovementioned general or preferred radical definitions or illustrations can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Emphasis is given to compounds of the formula (I) in which G represents hydrogen.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

Besides the compounds mentioned in the Preparation Examples, the following compounds of the formula (I-1-a) may be specifically mentioned:

TABLE 1

(I-1-a)

| A | X | W | Y | Z |
|---|---|---|---|---|
| —O—CH$_2$—CF$_3$ | CH$_3$ | H | H | H |
| —O—CH$_2$—CF$_3$ | Br | H | H | H |
| —O—CH$_2$—CF$_3$ | Cl | H | H | H |
| —O—CH$_2$—CF$_3$ | CF$_3$ | H | H | H |
| —O—CH$_2$—CF$_3$ | OCH$_3$ | H | H | H |
| —O—CH$_2$—CF$_3$ | Br | H | Cl | H |
| —O—CH$_2$—CF$_3$ | Cl | H | Br | H |
| —O—CH$_2$—CF$_3$ | Cl | H | Cl | H |
| —O—CH$_2$—CF$_3$ | Cl | H | CH$_3$ | H |
| —O—CH$_2$—CF$_3$ | CH$_3$ | H | Cl | H |
| —O—CH$_2$—CF$_3$ | Cl | Cl | H | H |
| —O—CH$_2$—CF$_3$ | Cl | OCH$_3$ | H | H |
| —O—CH$_2$—CF$_3$ | Cl | CH$_3$ | H | H |
| —O—CH$_2$—CF$_3$ | Cl | OC$_2$H$_5$ | H | H |
| —O—CH$_2$—CF$_3$ | OCH$_3$ | OCH$_3$ | H | H |
| —O—CH$_2$—CF$_3$ | CH$_3$ | CH$_3$ | H | H |
| —O—CH$_2$—CF$_3$ | C$_2$H$_5$ | CH$_3$ | H | H |
| —O—CH$_2$—CF$_3$ | C$_2$H$_5$ | C$_2$H$_5$ | H | H |
| —O—CH$_2$—CF$_3$ | Br | CH$_3$ | Br | H |
| —O—CH$_2$—CF$_3$ | Cl | CH$_3$ | Cl | H |
| —O—CH$_2$—CF$_3$ | CH$_3$ | Br | CH$_3$ | H |
| —O—CH$_2$—CF$_3$ | CH$_3$ | Cl | CH$_3$ | H |
| —O—CH$_2$—CF$_3$ | OCH$_3$ | CH$_3$ | CH$_3$ | H |
| —O—CH$_2$—CF$_3$ | OC$_2$H$_5$ | CH$_3$ | CH$_3$ | H |
| —O—CH$_2$—CF$_3$ | OC$_3$H$_7$ | CH$_3$ | CH$_3$ | H |
| —O—CH$_2$—CF$_3$ | CH$_3$ | CH$_3$ | CH$_3$ | H |
| —O—CH$_2$—CF$_3$ | Br | Br | CH$_3$ | H |
| —O—CH$_2$—CF$_3$ | Cl | Cl | CH$_3$ | H |
| —O—CH$_2$—CF$_3$ | CH$_3$ | CH$_3$ | Br | H |
| —O—CH$_2$—CF$_3$ | OCH$_3$ | C$_2$H$_5$ | CH$_3$ | H |
| —O—CH$_2$—CF$_3$ | OC$_2$H$_5$ | C$_2$H$_5$ | CH$_3$ | H |
| —O—CH$_2$—CF$_3$ | CH$_3$ | CH$_3$ | OCH$_3$ | H |
| —O—CH$_2$—CF$_3$ | Br | Cl | CH$_3$ | H |
| —O—CH$_2$—CF$_3$ | Br | CH$_3$ | Cl | H |
| —O—CH$_2$—CF$_3$ | Cl | CH$_3$ | Br | H |
| —O—CH$_2$—CF$_3$ | CH$_3$ | CH$_3$ | Cl | H |
| —O—CH$_2$—CF$_3$ | C$_2$H$_5$ | CH$_3$ | CH$_3$ | H |
| —O—CH$_2$—CF$_3$ | C$_2$H$_5$ | C$_2$H$_5$ | CH$_3$ | H |
| —O—CH$_2$—CF$_3$ | C$_2$H$_5$ | CH$_3$ | C$_2$H$_5$ | H |
| —O—CH$_2$—CF$_3$ | C$_2$H$_5$ | C$_2$H$_5$ | C$_2$H$_5$ | H |
| —O—CH$_2$—CF$_3$ | C$_2$H$_5$ | CH$_3$ | Cl | H |
| —O—CH$_2$—CF$_3$ | C$_2$H$_5$ | C$_2$H$_5$ | Cl | H |
| —O—CH$_2$—CF$_3$ | C$_2$H$_5$ | CH$_3$ | Br | H |
| —O—CH$_2$—CF$_3$ | C$_2$H$_5$ | C$_2$H$_5$ | Br | H |
| —O—CH$_2$—CF$_3$ | C$_2$H$_5$ | Cl | CH$_3$ | H |

TABLE 1-continued (I-1-a)

| A | X | W | Y | Z |
|---|---|---|---|---|
| —O—CH$_2$—CF$_3$ | C$_2$H$_5$ | Br | CH$_3$ | H |
| —O—CH$_2$—CF$_3$ | C$_2$H$_5$ | Cl | Cl | H |
| —O—CH$_2$—CF$_3$ | C$_2$H$_5$ | Br | Br | H |
| —O—CH$_2$—CF$_3$ | C$_2$H$_5$ | Cl | Br | H |
| —O—CH$_2$—CF$_3$ | C$_2$H$_5$ | Br | Cl | H |
| —O—CH$_2$—CF$_3$ | OCH$_3$ | CH$_3$ | Cl | H |
| —O—CH$_2$—CF$_3$ | OCH$_3$ | C$_2$H$_5$ | Cl | H |
| —O—CH$_2$—CF$_3$ | OC$_2$H$_5$ | CH$_3$ | Cl | H |
| —O—CH$_2$—CF$_3$ | OC$_2$H$_5$ | C$_2$H$_5$ | Cl | H |
| —O—CH$_2$—CF$_3$ | Cl | OCH$_3$ | CH$_3$ | H |
| —O—CH$_2$—CF$_3$ | Cl | OC$_2$H$_5$ | CH$_3$ | H |
| —O—CH$_2$—CF$_3$ | CH$_3$ | CH$_3$ | Cl | H |
| —O—CH$_2$—CF$_3$ | Cl | H | Cl | Cl |
| —O—CH$_2$—CF$_3$ | CH$_3$ | H | CH$_3$ | CH$_3$ |
| —O—CH$_2$—CF$_3$ | CH$_3$ | H | Cl | CH$_3$ |
| —O—CH$_2$—CF$_3$ | Br | H | Cl | CH$_3$ |
| —O—CH$_2$—CF$_3$ | Br | H | CH$_3$ | CH$_3$ |
| —O—CH$_2$—CF$_3$ | Cl | H | Br | CH$_3$ |
| —O—CH$_2$—CF$_3$ | Cl | H | Cl | CH$_3$ |
| —O—CH$_2$—CF$_3$ | CH$_3$ | H | Br | CH$_3$ |
| —O—CH$_2$—CF$_3$ | Cl | H | CH$_3$ | Cl |
| —O—CH$_2$—CF$_3$ | CH$_3$ | H | H | CH$_3$ |
| —O—CH$_2$—CF$_3$ | Cl | H | H | CH$_3$ |
| —O—CH$_2$—CF$_3$ | Br | H | H | CH$_3$ |
| —O—CH$_2$—CF$_3$ | CH$_3$ | H | H | Cl |
| —O—CH$_2$—CF$_3$ | CH$_3$ | H | H | Br |
| —O—CH$_2$—CF$_3$ | CH$_3$ | CH$_3$ | CH$_3$ | CH$_3$ |
| —O—CH$_2$—CF$_3$ | CH$_3$ | CH$_3$ | CH$_3$ | F |
| —O—CH$_2$—CF$_3$ | CH$_3$ | CH$_3$ | CH$_3$ | Cl |
| —O—CH$_2$—CF$_3$ | CH$_3$ | CH$_3$ | CH$_3$ | Br |
| —O—CH$_2$—CF$_3$ | CH$_3$ | CH$_3$ | H | Cl |
| —O—CH$_2$—CF$_3$ | CH$_3$ | CH$_3$ | H | Br |
| —O—CH$_2$—CF$_3$ | Cl | Cl | H | Br |
| —O—CH$_2$—CF$_3$ | CH$_3$ | CH$_3$ | 4-Cl—C$_6$H$_4$ | H |
| —O—CH$_2$—CF$_3$ | C$_2$H$_5$ | CH$_3$ | 4-Cl—C$_6$H$_4$ | H |
| —O—CH$_2$—CF$_3$ | C$_2$H$_5$ | C$_2$H$_5$ | 4-Cl—C$_6$H$_4$ | H |
| —O—CH$_2$—CF$_3$ | Cl | CH$_3$ | 4-Cl—C$_6$H$_4$ | H |
| —O—CH$_2$—CF$_3$ | Cl | C$_2$H$_5$ | 4-Cl—C$_6$H$_4$ | H |
| —O—CH$_2$—CF$_3$ | CH$_3$ | H | H | 4-Cl—C$_6$H$_4$ |
| —O—CH$_2$—CF$_3$ | CH$_3$ | CH$_3$ | H | 4-Cl—C$_6$H$_4$ |
| —O—CH$_2$—CF$_3$ | CH$_3$ | H | CH$_3$ | 4-Cl—C$_6$H$_4$ |
| —O—CH$_2$—CF$_3$ | CH$_3$ | CH$_3$ | CH$_3$ | 4-Cl—C$_6$H$_4$ |
| —O—CH$_2$—CF$_3$ | Cl | H | H | 4-Cl—C$_6$H$_4$ |
| —O—CH$_2$—CF$_3$ | I | H | H | H |
| —O—CH$_2$—CF$_3$ | I | H | CH$_3$ | H |
| —O—CH$_2$—CF$_3$ | I | CH$_3$ | H | H |
| —O—CH$_2$—CF$_3$ | I | C$_2$H$_5$ | H | H |
| —O—CH$_2$—CF$_3$ | CH$_3$ | H | H | I |
| —O—CH$_2$—CF$_3$ | CH$_3$ | H | CH$_3$ | I |
| —O—CH$_2$—CF$_3$ | I | CH$_3$ | CH$_3$ | H |
| —O—CH$_2$—CF$_3$ | I | C$_2$H$_5$ | CH$_3$ | H |
| —O—CH$_2$—CF$_3$ | I | CH$_3$ | Cl | H |
| —O—CH$_2$—CF$_3$ | I | C$_2$H$_5$ | Cl | H |
| —O—CH$_2$—CF$_3$ | I | Cl | CH$_3$ | H |
| —O—CH$_2$—CF$_3$ | I | H | CH$_3$ | CH$_3$ |
| —O—CH$_2$—CF$_3$ | CH$_3$ | H | I | H |
| —O—CH$_2$—CF$_3$ | C$_2$H$_5$ | H | I | H |
| —O—CH$_2$—CF$_3$ | CH$_3$ | CH$_3$ | I | H |
| —O—CH$_2$—CF$_3$ | C$_2$H$_5$ | CH$_3$ | I | H |
| —O—CH$_2$—CF$_3$ | C$_2$H$_5$ | C$_2$H$_5$ | I | H |
| —O—CH$_2$—CF$_3$ | Cl | CH$_3$ | I | H |
| —O—CH$_2$—CF$_3$ | Cl | C$_2$H$_5$ | I | H |
| —O—CH$_2$—CF$_3$ | CH$_3$ | H | I | CH$_3$ |
| —O—CH$_2$—CF$_3$ | CH$_3$ | CH$_3$ | H | I |
| —O—CH$_2$—CF$_3$ | I | H | H | CH$_3$ |
| —O—CH$_2$—CF$_3$ | C$_2$H$_5$ | H | H | H |

TABLE 1-continued (I-1-a)

| A | X | W | Y | Z |
|---|---|---|---|---|
| —O—CH$_2$—CF$_3$ | △ | H | H | H |
| —O—CH$_2$—CF$_3$ | △ | CH$_3$ | H | H |
| —O—CH$_2$—CF$_3$ | △ | H | CH$_3$ | H |
| —O—CH$_2$—CF$_3$ | △ | C$_2$H$_5$ | H | H |
| —O—CH$_2$—CF$_3$ | △ | CH$_3$ | CH$_3$ | H |
| —O—CH$_2$—CF$_3$ | △ | C$_2$H$_5$ | CH$_3$ | H |
| —O—CH$_2$—CF$_3$ | △ | CH$_3$ | Cl | H |
| —O—CH$_2$—CF$_3$ | △ | C$_2$H$_5$ | Cl | H |
| —O—CH$_2$—CF$_3$ | △ | Cl | CH$_3$ | H |
| —O—CH$_2$—CF$_3$ | CH$_3$ | H | △ | H |
| —O—CH$_2$—CF$_3$ | C$_2$H$_5$ | H | △ | H |
| —O—CH$_2$—CF$_3$ | CH$_3$ | CH$_3$ | △ | H |
| —O—CH$_2$—CF$_3$ | C$_2$H$_5$ | CH$_3$ | △ | H |
| —O—CH$_2$—CF$_3$ | C$_2$H$_5$ | C$_2$H$_5$ | △ | H |
| —O—CH$_2$—CF$_3$ | Cl | CH$_3$ | △ | H |
| —O—CH$_2$—CF$_3$ | Cl | C$_2$H$_5$ | △ | H |

Besides the compounds mentioned in the Preparation Examples, the following compounds of the formula (I-2-a) may be specifically mentioned:

TABLE 2

(I-2-a)

| A | X | W | Y | Z |
|---|---|---|---|---|
| —O—CH$_2$—CF$_3$ | CH$_3$ | H | H | H |
| —O—CH$_2$—CF$_3$ | Br | H | H | H |
| —O—CH$_2$—CF$_3$ | Cl | H | H | H |
| —O—CH$_2$—CF$_3$ | CF$_3$ | H | H | H |
| —O—CH$_2$—CF$_3$ | OCH$_3$ | H | H | H |
| —O—CH$_2$—CF$_3$ | Br | H | Cl | H |
| —O—CH$_2$—CF$_3$ | Cl | H | Br | H |
| —O—CH$_2$—CF$_3$ | Cl | H | Cl | H |
| —O—CH$_2$—CF$_3$ | Cl | H | CH$_3$ | H |
| —O—CH$_2$—CF$_3$ | CH$_3$ | H | Cl | H |
| —O—CH$_2$—CF$_3$ | Cl | Cl | H | H |
| —O—CH$_2$—CF$_3$ | Cl | OCH$_3$ | H | H |
| —O—CH$_2$—CF$_3$ | Cl | CH$_3$ | H | H |
| —O—CH$_2$—CF$_3$ | Cl | OC$_2$H$_5$ | H | H |
| —O—CH$_2$—CF$_3$ | OCH$_3$ | OCH$_3$ | H | H |
| —O—CH$_2$—CF$_3$ | CH$_3$ | CH$_3$ | H | H |
| —O—CH$_2$—CF$_3$ | C$_2$H$_5$ | CH$_3$ | H | H |
| —O—CH$_2$—CF$_3$ | C$_2$H$_5$ | C$_2$H$_5$ | H | H |
| —O—CH$_2$—CF$_3$ | Br | CH$_3$ | Br | H |
| —O—CH$_2$—CF$_3$ | Cl | CH$_3$ | Cl | H |
| —O—CH$_2$—CF$_3$ | CH$_3$ | Br | CH$_3$ | H |
| —O—CH$_2$—CF$_3$ | CH$_3$ | Cl | CH$_3$ | H |
| —O—CH$_2$—CF$_3$ | OCH$_3$ | CH$_3$ | CH$_3$ | H |
| —O—CH$_2$—CF$_3$ | OC$_2$H$_5$ | CH$_3$ | CH$_3$ | H |
| —O—CH$_2$—CF$_3$ | OC$_3$H$_7$ | CH$_3$ | CH$_3$ | H |
| —O—CH$_2$—CF$_3$ | CH$_3$ | CH$_3$ | CH$_3$ | H |
| —O—CH$_2$—CF$_3$ | Br | Br | CH$_3$ | H |
| —O—CH$_2$—CF$_3$ | Cl | Cl | CH$_3$ | H |
| —O—CH$_2$—CF$_3$ | CH$_3$ | CH$_3$ | Br | H |
| —O—CH$_2$—CF$_3$ | OCH$_3$ | C$_2$H$_5$ | CH$_3$ | H |
| —O—CH$_2$—CF$_3$ | OC$_2$H$_5$ | C$_2$H$_5$ | CH$_3$ | H |
| —O—CH$_2$—CF$_3$ | CH$_3$ | CH$_3$ | OCH$_3$ | H |
| —O—CH$_2$—CF$_3$ | Br | Cl | CH$_3$ | H |
| —O—CH$_2$—CF$_3$ | Br | CH$_3$ | Cl | H |
| —O—CH$_2$—CF$_3$ | Cl | CH$_3$ | Br | H |
| —O—CH$_2$—CF$_3$ | CH$_3$ | CH$_3$ | Cl | H |
| —O—CH$_2$—CF$_3$ | C$_2$H$_5$ | CH$_3$ | CH$_3$ | H |
| —O—CH$_2$—CF$_3$ | C$_2$H$_5$ | C$_2$H$_5$ | CH$_3$ | H |
| —O—CH$_2$—CF$_3$ | C$_2$H$_5$ | CH$_3$ | C$_2$H$_5$ | H |
| —O—CH$_2$—CF$_3$ | C$_2$H$_5$ | C$_2$H$_5$ | C$_2$H$_5$ | H |
| —O—CH$_2$—CF$_3$ | C$_2$H$_5$ | CH$_3$ | Cl | H |
| —O—CH$_2$—CF$_3$ | C$_2$H$_5$ | C$_2$H$_5$ | Cl | H |
| —O—CH$_2$—CF$_3$ | C$_2$H$_5$ | CH$_3$ | Br | H |
| —O—CH$_2$—CF$_3$ | C$_2$H$_5$ | C$_2$H$_5$ | Br | H |
| —O—CH$_2$—CF$_3$ | C$_2$H$_5$ | Cl | CH$_3$ | H |
| —O—CH$_2$—CF$_3$ | C$_2$H$_5$ | Br | CH$_3$ | H |
| —O—CH$_2$—CF$_3$ | C$_2$H$_5$ | Cl | Cl | H |
| —O—CH$_2$—CF$_3$ | C$_2$H$_5$ | Br | Br | H |
| —O—CH$_2$—CF$_3$ | C$_2$H$_5$ | Cl | Br | H |
| —O—CH$_2$—CF$_3$ | C$_2$H$_5$ | Br | Cl | H |
| —O—CH$_2$—CF$_3$ | OCH$_3$ | CH$_3$ | Cl | H |
| —O—CH$_2$—CF$_3$ | OCH$_3$ | C$_2$H$_5$ | Cl | H |
| —O—CH$_2$—CF$_3$ | OC$_2$H$_5$ | CH$_3$ | Cl | H |
| —O—CH$_2$—CF$_3$ | OC$_2$H$_5$ | C$_2$H$_5$ | Cl | H |
| —O—CH$_2$—CF$_3$ | Cl | OCH$_3$ | CH$_3$ | H |
| —O—CH$_2$—CF$_3$ | Cl | OC$_2$H$_5$ | CH$_3$ | H |
| —O—CH$_2$—CF$_3$ | CH$_3$ | CH$_3$ | Cl | H |
| —O—CH$_2$—CF$_3$ | Cl | H | Cl | Cl |
| —O—CH$_2$—CF$_3$ | CH$_3$ | H | CH$_3$ | CH$_3$ |
| —O—CH$_2$—CF$_3$ | CH$_3$ | H | Cl | CH$_3$ |
| —O—CH$_2$—CF$_3$ | Br | H | Cl | CH$_3$ |
| —O—CH$_2$—CF$_3$ | Br | H | CH$_3$ | CH$_3$ |
| —O—CH$_2$—CF$_3$ | Cl | H | Br | CH$_3$ |
| —O—CH$_2$—CF$_3$ | Cl | H | Cl | CH$_3$ |
| —O—CH$_2$—CF$_3$ | CH$_3$ | H | Br | CH$_3$ |
| —O—CH$_2$—CF$_3$ | Cl | H | CH$_3$ | Cl |
| —O—CH$_2$—CF$_3$ | CH$_3$ | H | H | CH$_3$ |
| —O—CH$_2$—CF$_3$ | Cl | H | H | CH$_3$ |

TABLE 2-continued

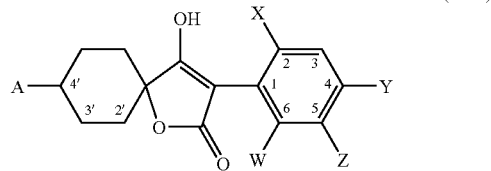

(I-2-a)

| A | X | W | Y | Z |
|---|---|---|---|---|
| —O—CH$_2$—CF$_3$ | Br | H | H | CH$_3$ |
| —O—CH$_2$—CF$_3$ | CH$_3$ | H | H | Cl |
| —O—CH$_2$—CF$_3$ | CH$_3$ | H | H | Br |
| —O—CH$_2$—CF$_3$ | CH$_3$ | CH$_3$ | CH$_3$ | CH$_3$ |
| —O—CH$_2$—CF$_3$ | CH$_3$ | CH$_3$ | CH$_3$ | F |
| —O—CH$_2$—CF$_3$ | CH$_3$ | CH$_3$ | CH$_3$ | Cl |
| —O—CH$_2$—CF$_3$ | CH$_3$ | CH$_3$ | CH$_3$ | Br |
| —O—CH$_2$—CF$_3$ | CH$_3$ | CH$_3$ | H | Cl |
| —O—CH$_2$—CF$_3$ | CH$_3$ | CH$_3$ | H | Br |
| —O—CH$_2$—CF$_3$ | Cl | Cl | H | Br |
| —O—CH$_2$—CF$_3$ | CH$_3$ | CH$_3$ | 4-Cl—C$_6$H$_4$ | H |
| —O—CH$_2$—CF$_3$ | C$_2$H$_5$ | CH$_3$ | 4-Cl—C$_6$H$_4$ | H |
| —O—CH$_2$—CF$_3$ | C$_2$H$_5$ | C$_2$H$_5$ | 4-Cl—C$_6$H$_4$ | H |
| —O—CH$_2$—CF$_3$ | Cl | CH$_3$ | 4-Cl—C$_6$H$_4$ | H |
| —O—CH$_2$—CF$_3$ | Cl | C$_2$H$_5$ | 4-Cl—C$_6$H$_4$ | H |
| —O—CH$_2$—CF$_3$ | CH$_3$ | H | H | 4-Cl—C$_6$H$_4$ |
| —O—CH$_2$—CF$_3$ | CH$_3$ | CH$_3$ | H | 4-Cl—C$_6$H$_4$ |
| —O—CH$_2$—CF$_3$ | CH$_3$ | H | CH$_3$ | 4-Cl—C$_6$H$_4$ |
| —O—CH$_2$—CF$_3$ | CH$_3$ | CH$_3$ | CH$_3$ | 4-Cl—C$_6$H$_4$ |
| —O—CH$_2$—CF$_3$ | Cl | H | H | 4-Cl—C$_6$H$_4$ |
| —O—CH$_2$—CF$_3$ | I | H | H | H |
| —O—CH$_2$—CF$_3$ | I | H | CH$_3$ | H |
| —O—CH$_2$—CF$_3$ | I | CH$_3$ | H | H |
| —O—CH$_2$—CF$_3$ | I | C$_2$H$_5$ | H | H |
| —O—CH$_2$—CF$_3$ | CH$_3$ | H | H | I |
| —O—CH$_2$—CF$_3$ | CH$_3$ | H | CH$_3$ | I |
| —O—CH$_2$—CF$_3$ | I | CH$_3$ | CH$_3$ | H |
| —O—CH$_2$—CF$_3$ | I | C$_2$H$_5$ | CH$_3$ | H |
| —O—CH$_2$—CF$_3$ | I | CH$_3$ | Cl | H |
| —O—CH$_2$—CF$_3$ | I | C$_2$H$_5$ | Cl | H |
| —O—CH$_2$—CF$_3$ | I | Cl | CH$_3$ | H |
| —O—CH$_2$—CF$_3$ | I | H | CH$_3$ | CH$_3$ |
| —O—CH$_2$—CF$_3$ | CH$_3$ | H | I | H |
| —O—CH$_2$—CF$_3$ | C$_2$H$_5$ | H | I | H |
| —O—CH$_2$—CF$_3$ | CH$_3$ | CH$_3$ | I | H |
| —O—CH$_2$—CF$_3$ | C$_2$H$_5$ | CH$_3$ | I | H |
| —O—CH$_2$—CF$_3$ | C$_2$H$_5$ | C$_2$H$_5$ | I | H |
| —O—CH$_2$—CF$_3$ | Cl | CH$_3$ | I | H |
| —O—CH$_2$—CF$_3$ | Cl | C$_2$H$_5$ | I | H |
| —O—CH$_2$—CF$_3$ | CH$_3$ | H | I | CH$_3$ |
| —O—CH$_2$—CF$_3$ | CH$_3$ | CH$_3$ | H | I |
| —O—CH$_2$—CF$_3$ | I | H | H | CH$_3$ |
| —O—CH$_2$—CF$_3$ | △ | H | H | H |
| —O—CH$_2$—CF$_3$ | △ | CH$_3$ | H | H |
| —O—CH$_2$—CF$_3$ | △ | H | CH$_3$ | H |
| —O—CH$_2$—CF$_3$ | △ | C$_2$H$_5$ | H | H |
| —O—CH$_2$—CF$_3$ | △ | CH$_3$ | CH$_3$ | H |
| —O—CH$_2$—CF$_3$ | △ | C$_2$H$_5$ | CH$_3$ | H |
| —O—CH$_2$—CF$_3$ | △ | CH$_3$ | Cl | H |
| —O—CH$_2$—CF$_3$ | △ | C$_2$H$_5$ | Cl | H |
| —O—CH$_2$—CF$_3$ | △ | Cl | CH$_3$ | H |
| —O—CH$_2$—CF$_3$ | CH$_3$ | H | △ | H |
| —O—CH$_2$—CF$_3$ | C$_2$H$_5$ | H | △ | H |
| —O—CH$_2$—CF$_3$ | CH$_3$ | CH$_3$ | △ | H |
| —O—CH$_2$—CF$_3$ | C$_2$H$_5$ | CH$_3$ | △ | H |
| —O—CH$_2$—CF$_3$ | C$_2$H$_5$ | C$_2$H$_5$ | △ | H |
| —O—CH$_2$—CF$_3$ | Cl | CH$_3$ | △ | H |
| —O—CH$_2$—CF$_3$ | Cl | C$_2$H$_5$ | △ | H |

Preferred definitions of the groups listed above in connection with the crop plant compatibility-improving compounds ("herbicide safeners") of the formulae (II), (IIb), (IIc), (IId) and (IIe) are defined below.

m preferably represents the number 0, 1, 2, 3 or 4.

A$^1$ preferably represents one of the divalent heterocyclic groupings shown below,

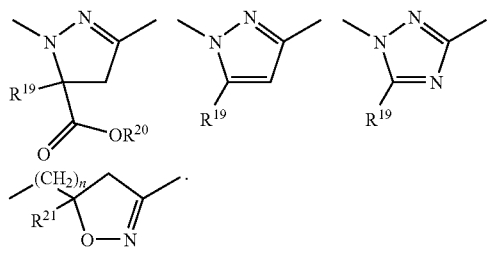

n preferably represents the number 0, 1, 2, 3 or 4.

A$^2$ preferably represents in each case optionally methyl-, ethyl-, methoxycarbonyl-, ethoxycarbonyl- or allyloxycarbonyl-substituted methylene or ethylene.

R$^{14}$ preferably represents hydroxyl, mercapto, amino, methoxy, ethoxy, n- or i-propoxy, n-, s- or t-butoxy, methylthio, ethylthio, n- or i-propylthio, n-, s- or t-butylthio, methylamino, ethylamino, n- or i-propylamino, n-, s- or t-butylamino, dimethylamino or diethylamino.

R$^{15}$ preferably represents hydroxyl, mercapto, amino, methoxy, ethoxy, n- or i-propoxy, n-, s- or t-butoxy, 1-methylhexyloxy, allyloxy, 1-allyloxymethylethoxy, methylthio, ethylthio, n- or i-propylthio, n-, s- or t-butylthio, methylamino, ethylamino, n- or i-propylamino, n-, s- or t-butylamino, dimethylamino or diethylamino.

$R^{16}$ preferably represents in each case optionally fluorine-, chlorine-, and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, s- or t-butyl-substituted phenyl.

$R^{18}$ preferably represents hydrogen, in each case optionally fluorine- and/or chlorine-substituted methyl, ethyl, n- or i-propyl, n-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, s- or t-butyl-substituted phenyl, or together with $R^{17}$ represents one of the radicals —$CH_2$—O—$CH_2$—$CH_2$— and —$CH_2$—$CH_2$—O—$CH_2$—$CH_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

$R^{20}$ preferably represents hydrogen, in each case optionally hydroxyl-, cyano-, fluorine-, chlorine-, methoxy-, ethoxy-, n- or i-propoxy-substituted methyl, ethyl, n- or i-propyl, n-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

t preferably represents the number 0, 1, 2, 3 or 4.

v preferably represents the number 0, 1, 2 or 3.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, s- or t-butyl, methoxy, ethoxy, n- or i-propoxy, n-, s- or t-butoxy, methylthio, ethylthio, n- or i-propylthio, n-, s- or t-butylthio, methylamino, ethylamino, n- or i-propylamino, n-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclo-pentyl, cyclohexyl, cyclopropyloxy, cyclobutyloxy, cyclopentyloxy, cyclohexyloxy, cyclo-propylthio, cyclobutylthio, cyclopentylthio, cyclohexylthio, cyclopropylamino, cyclobutyl-amino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulfamoyl, hydroxyl, amino, fluorine, chlorine, bromine, methyl, ethyl, n- or i-propyl, n-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulfamoyl, hydroxyl, amino, fluorine, chlorine, bromine, methyl, ethyl, n- or i-propyl, n-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

(IIa)

| Example No. | (Positions) $(X^1)_m$ | $A^1$ | $R^{14}$ |
|---|---|---|---|
| IIa-1 | (2) Cl, (4) Cl | (pyrazoline structure with $H_3C$ and $OCH_3$) | $OCH_3$ |

TABLE-continued

Examples of the compounds of the formula (IIa)

| Example No. | (Positions) $(X^1)_m$ | $A^1$ | $R^{14}$ |
|---|---|---|---|
| IIa-2 | (2) Cl, (4) Cl | 1,3-dimethyl-5-methyl-5-(ethoxycarbonyl)-4,5-dihydropyrazol-5-yl | OCH$_3$ |
| IIa-3 | (2) Cl, (4) Cl | 1,3-dimethyl-5-methyl-5-(methoxycarbonyl)-4,5-dihydropyrazol-5-yl | OC$_2$H$_5$ |
| IIa-4 | (2) Cl, (4) Cl | 1,3-dimethyl-5-methyl-5-(ethoxycarbonyl)-4,5-dihydropyrazol-5-yl | OC$_2$H$_5$ |
| IIa-5 | (2) Cl | 1,3-dimethyl-5-phenylpyrazol-4-yl | OCH$_3$ |
| IIa-6 | (2) Cl, (4) Cl | 1,3-dimethyl-5-phenylpyrazol-4-yl | OCH$_3$ |
| IIa-7 | (2) F | 1,3-dimethyl-5-phenylpyrazol-4-yl | OCH$_3$ |
| IIa-8 | (2) F | 1,3-dimethyl-5-(2-chlorophenyl)pyrazol-4-yl | OCH$_3$ |
| IIa-9 | (2) Cl, (4) Cl | 1,3-dimethyl-5-(trichloromethyl)-1,2,4-triazol-4-yl | OC$_2$H$_5$ |
| IIa-10 | (2) Cl, (4) CF$_3$ | 1,3-dimethyl-5-phenyl-1,2,4-triazol-4-yl | OCH$_3$ |
| IIa-11 | (2) Cl | 1,3-dimethyl-5-(2-fluorophenyl)pyrazol-4-yl | OCH$_3$ |
| IIa-12 | — | 3-methyl-5-phenyl-5-methyl-4,5-dihydroisoxazol-4-yl | OC$_2$H$_5$ |
| IIa-13 | (2) Cl, (4) Cl | 1,3-dimethyl-5-methylpyrazol-4-yl | OC$_2$H$_5$ |
| IIa-14 | (2) Cl, (4) Cl | 1,3-dimethyl-5-isopropylpyrazol-4-yl | OC$_2$H$_5$ |
| IIa-15 | (2) Cl, (4) Cl | 1,3-dimethyl-5-tert-butylpyrazol-4-yl | OC$_2$H$_5$ |
| IIa-16 | (2) Cl, (4) Cl | 3-methyl-5-methyl-4,5-dihydroisoxazol-4-yl (CH$_2$) | OC$_2$H$_5$ |
| IIa-17 | (2) Cl, (4) Cl | 3,5-dimethyl-4,5-dihydroisoxazol-4-yl | OC$_2$H$_5$ |

Examples of the compounds of the formula (IIa)

(IIa)

| Example No. | (Positions) $(X^1)_m$ | $A^1$ | $R^{14}$ |
|---|---|---|---|
| IIa-18 | — | 5-phenyl-3,5-dimethyl-4,5-dihydroisoxazol-5-yl group | OH |

Examples of the compounds of the formula (IIb) which are very particularly preferred as herbicide safeners according to the invention are listed in the table below.

Examples of the compounds of the formula (IIb)

(IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | $OCH_2CH(OCH_2CH_2O-)CH_3$ (cyclic acetal-type group) |
| IIb-13 | (5) Cl | — | $CH(CH_2CH=CH_2)$ | $OCH_2CH=CH_2$ |
| IIb-14 | (5) Cl | — | $CH(C_2H_5)$ | $OC_2H_5$ |
| IIb-15 | (5) Cl | — | $CH(CH_3)$ | $OCH_3$ |

Examples of the compounds of the formula (IIc) which are very particularly preferred as herbicide safeners according to the invention are listed in the table below.

Examples of the compounds of the formula (IIc)

(IIc)

| Example No. | $R^{16}$ | $N(R^{17}, R^{18})$ |
|---|---|---|
| IIc-1 | $CHCl_2$ | $N(CH_2CH=CH_2)_2$ |
| IIc-2 | $CHCl_2$ | 2,2-dimethyl-oxazolidin-3-yl |

TABLE-continued

Examples of the compounds of the formula (IIc)

(IIc)

| Example No. | $R^{16}$ | $N(R^{17}, R^{18})$ |
|---|---|---|
| IIc-3 | $CHCl_2$ | 2,3,5-trimethyl-oxazolidine |
| IIc-4 | $CHCl_2$ | 4-methyl-1-oxa-4-azaspiro[4.5]decane |
| IIc-5 | $CHCl_2$ | 2,2,3-trimethyl-5-phenyl-oxazolidine |
| IIc-6 | $CHCl_2$ | 3,4-dimethyl-3,4-dihydro-2H-1,4-benzoxazine |
| IIc-7 | $CHCl_2$ | 2,2,3-trimethyl-5-(2-furyl)-oxazolidine |

TABLE

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | cyclopropyl-NH | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IId) which are very particularly preferred as herbicide safeners according to the invention are listed in the table below.

Examples of the compounds of the formula (IIe) which are very particularly preferred as herbicide safeners according to the invention are listed in the table below.

TABLE

Examples of the compounds of the formula (IIe)

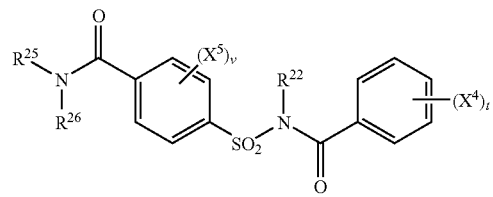

(IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | $CH_3$ | $CH_3$ | (2) $OCH_3$ | — |
| IIe-7 | H | H | $CH_3$ | (2) $OCH_3$ | (5) $CH_3$ |
| IIe-8 | H | H | $C_2H_5$ | (2) $OCH_3$ | (5) $CH_3$ |
| IIe-9 | H | H | $C_3H_7$-n | (2) $OCH_3$ | (5) $CH_3$ |
| IIe-10 | H | H | $C_3H_7$-i | (2) $OCH_3$ | (5) $CH_3$ |
| IIe-11 | H | H | cyclopropyl | (2) $OCH_3$ | (5) $CH_3$ |
| IIe-12 | H | $CH_3$ | $CH_3$ | (2) $OCH_3$ | (5) $CH_3$ |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used according to the invention as safeners are known and/or can be prepared by processes known per se (cf. WO-A-91/07874, WO-A-95/07897).

The compounds of the general formula (IIb) to be used according to the invention as safeners are known and/or can be prepared by processes known per se (cf. EP-A-191736).

The compounds of the general formula (IIc) to be used according to the invention as safeners are known and/or can be prepared by processes known per se (cf. DE-A-2218097, DE-A-2350547).

The compounds of the general formula (IId) to be used according to the invention as safeners are known and/or can be prepared by processes known per se (cf. DE-A-19621522/ U.S. Pat. No. 6,235,680).

The compounds of the general formula (IIe) to be used according to the invention as safeners are known and can be prepared by processes known per se (cf. WO-A-99/66795/ U.S. Pat. No. 6,251,827).

Examples of the selective herbicidal combinations according to the invention comprising in each case one active compound of the formula (I) and in each case one of the safeners defined above are listed in the table below.

TABLE

Examples of combinations according to the invention

| Active compounds of the formula (I) | Safeners |
|---|---|
| I-1-a | cloquintocet-mexyl |
| I-1-a | fenchlorazole-ethyl |
| I-1-a | isoxadifen-ethyl |
| I-1-a | mefenpyr-diethyl |
| I-1-a | furilazole |
| I-1-a | fenclorim |
| I-1-a | cumyluron |
| I-1-a | daimuron/dymron |
| I-1-a | dimepiperate |
| I-1-a | IIe-11 |
| I-1-a | IIe-5 |
| I-1-b | cloquintocet-mexyl |
| I-1-b | fenchlorazole-ethyl |
| I-1-b | isoxadifen-ethyl |
| I-1-b | mefenpyr-diethyl |
| I-1-b | furilazole |
| I-1-b | fenclorim |
| I-1-b | cumyluron |
| I-1-b | daimuron/dymron |
| I-1-b | dimepiperate |
| I-1-b | IIe-11 |
| I-1-b | IIe-5 |
| I-1-c | cloquintocet-mexyl |
| I-1-c | fenchlorazole-ethyl |
| I-1-c | isoxadifen-ethyl |
| I-1-c | mefenpyr-diethyl |
| I-1-c | furilazole |
| I-1-c | fenclorim |
| I-1-c | cumyluron |
| I-1-c | daimuron/dymron |
| I-1-c | dimepiperate |
| I-1-c | IIe-5 |
| I-1-c | IIe-11 |
| I-1-d | cloquintocet-mexyl |
| I-1-d | fenchlorazole-ethyl |
| I-1-d | isoxadifen-ethyl |
| I-1-d | mefenpyr-diethyl |
| I-1-d | furilazole |
| I-1-d | fenclorim |
| I-1-d | cumyluron |
| I-1-d | daimuron/dymron |
| I-1-d | dimepiperate |
| I-1-d | IIe-11 |
| I-1-d | IIe-5 |
| I-1-e | cloquintocet-mexyl |
| I-1-e | fenchlorazole-ethyl |
| I-1-e | isoxadifen-ethyl |
| I-1-e | mefenpyr-diethyl |
| I-1-e | furilazole |
| I-1-e | fenclorim |
| I-1-e | cumyluron |
| I-1-e | daimuron/dymron |
| I-1-e | dimepiperate |
| I-1-e | IIe-5 |
| I-1-e | IIe-11 |
| I-1-f | cloquintocet-mexyl |
| I-1-f | fenchlorazole-ethyl |
| I-1-f | isoxadifen-ethyl |
| I-1-f | mefenpyr-diethyl |
| I-1-f | furilazole |
| I-1-f | fenclorim |
| I-1-f | cumyluron |
| I-1-f | daimuron/dymron |
| I-1-f | dimepiperate |
| I-1-f | IIe-5 |
| I-1-f | IIe-11 |
| I-1-g | cloquintocet-mexyl |
| I-1-g | fenchlorazole-ethyl |
| I-1-g | isoxadifen-ethyl |
| I-1-g | mefenpyr-diethyl |
| I-1-g | furilazole |

TABLE-continued

Examples of combinations according to the invention

| Active compounds of the formula (I) | Safeners |
|---|---|
| I-1-g | fenclorim |
| I-1-g | cumyluron |
| I-1-g | daimuron/dymron |
| I-1-g | dimepiperate |
| I-1-g | IIe-5 |
| I-1-g | IIe-11 |
| I-2-a | cloquintocet-mexyl |
| I-2-a | fenchlorazole-ethyl |
| I-2-a | isoxadifen-ethyl |
| I-2-a | mefenpyr-diethyl |
| I-2-a | furilazole |
| I-2-a | fenclorim |
| I-2-a | cumyluron |
| I-2-a | daimuron/dymron |
| I-2-a | dimepiperate |
| I-2-a | IIe-5 |
| I-2-a | IIe-11 |
| I-2-b | cloquintocet-mexyl |
| I-2-b | fenchlorazole-ethyl |
| I-2-b | isoxadifen-ethyl |
| I-2-b | mefenpyr-diethyl |
| I-2-b | furilazole |
| I-2-b | fenclorim |
| I-2-b | cumyluron |
| I-2-b | daimuron/dymron |
| I-2-b | dimepiperate |
| I-2-b | IIe-5 |
| I-2-b | IIe-11 |
| I-2-c | cloquintocet-mexyl |
| I-2-c | fenchlorazole-ethyl |
| I-2-c | isoxadifen-ethyl |
| I-2-c | mefenpyr-diethyl |
| I-2-c | furilazole |
| I-2-c | fenclorim |
| I-2-c | cumyluron |
| I-2-c | daimuron/dymron |
| I-2-c | dimepiperate |
| I-2-c | IIe-5 |
| I-2-c | IIe-11 |
| I-2-d | cloquintocet-mexyl |
| I-2-d | fenchlorazole-ethyl |
| I-2-d | isoxadifen-ethyl |
| I-2-d | mefenpyr-diethyl |
| I-2-d | furilazole |
| I-2-d | fenclorim |
| I-2-d | cumyluron |
| I-2-d | daimuron/dymron |
| I-2-d | dimepiperate |
| I-2-d | IIe-5 |
| I-2-d | IIe-11 |
| I-2-e | cloquintocet-mexyl |
| I-2-e | fenchlorazole-ethyl |
| I-2-e | isoxadifen-ethyl |
| I-2-e | mefenpyr-diethyl |
| I-2-e | furilazole |
| I-2-e | fenclorim |
| I-2-e | cumyluron |
| I-2-e | daimuron/dymron |
| I-2-e | dimepiperate |
| I-2-e | IIe-5 |
| I-2-e | IIe-11 |
| I-2-f | cloquintocet-mexyl |
| I-2-f | fenchlorazole-ethyl |
| I-2-f | isoxadifen-ethyl |
| I-2-f | mefenpyr-diethyl |
| I-2-f | furilazole |
| I-2-f | fenclorim |
| I-2-f | cumyluron |
| I-2-f | daimuron/dymron |
| I-2-f | dimepiperate |
| I-2-f | IIe-5 |
| I-2-f | IIe-11 |
| I-2-g | cloquintocet-mexyl |
| I-2-g | fenchlorazole-ethyl |
| I-2-g | isoxadifen-ethyl |
| I-2-g | mefenpyr-diethyl |
| I-2-g | furilazole |
| I-2-g | fenclorim |
| I-2-g | cumyluron |
| I-2-g | daimuron/dymron |
| I-2-g | dimepiperate |
| I-2-g | IIe-5 |
| I-2-g | IIe-11 |

Surprisingly, it has now been found that the active compound combinations defined above of compounds of the general formula (I) and safeners (antidotes) from the group (b') set out above combine very good useful plant tolerance with a particularly high herbicidal activity and can be used in various crops, in particular in cereals (especially wheat), but also in soya, potatoes, corn and rice, for the selective control of weeds.

In this context it is to be considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of haloalkoxyspirocyclic tetramic and tetronic acid derivatives on the crop plants, without at the same time having any critical adverse effect on the herbicidal activity against the weeds.

Emphasis may be given here to the particularly advantageous effect of the particularly preferred and most preferred combination partners from group (b'), in particular with regard to the gentle treatment of cereal plants, such as wheat, barley and rye, for example, but also corn and rice, as crop plants.

In the literature it has already been described how the action of various active compounds can be increased by addition of ammonium salts. The salts in question, however, are detersive salts (e.g. WO 95/017817) or salts which have relatively long alkyl substituents and/or aryl substituents and which have a permeabilizing action or which increase the solubility of the active compound (e.g. EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Furthermore, the prior art describes the activity only for certain active compounds and/or certain applications of the corresponding compositions. In yet further cases, these are salts of sulfonic acids where the acids for their part have a paralyzing action on insects (U.S. Pat. No. 2,842,476). An increase in action by ammonium sulfate, for example, is described by way of example for the herbicides glyphosate and phosphinothricin and for phenyl-substituted cyclic ketoenols (U.S. Pat. No. 6,645,914, EP-A2 0 036 106, WO 07/068,427). A corresponding increase in action in the case of insecticides is described for certain cyclic ketoenols in WO 07/068,428.

The use of ammonium sulfate as a formulating assistant has also been described for certain active compounds and applications (WO 92/16108), but its purpose therein is to stabilize the formulation, not to increase the action.

It has now been found, likewise surprisingly, that the action of insecticides and/or acaricides and/or herbicides from the class of the haloalkoxyspirocyclic tetramic and tetronic acid derivatives can be increased significantly by the addition of ammonium salts or phosphonium salts to the application solution or by the incorporation of these salts into a formulation comprising haloalkoxyspirocyclic tetramic and tetronic acid derivatives of the formula (I). The present invention therefore provides for the use of ammonium salts or phosphonium salts for increasing the action of crop protection compositions which comprise as their active compound herbicidal and/or insecticidal and/or acaricidal haloalkoxyspirocyclic tetramic and tetronic acid derivatives of the formula (I). The invention likewise provides compositions which comprise herbicidal and/or acaricidal and/or insecticidal haloalkoxyspirocyclic tetramic and tetronic acid derivatives of the formula (I) and action-increasing ammonium salts or phosphonium salts, including both formulated active compounds and also ready-to-use compositions (spray liquors). The invention further provides, finally, for the use of these compositions for controlling insect pests and/or spider mites and/or unwanted vegetation.

The compounds of the formula (I) possess a broad insecticidal and/or acaricidal and/or herbicidal activity, but individually the activity and/or plant tolerance leaves something to be desired. However, by adding ammonium or phosphonium salts, some or all of these properties can be improved.

The active compounds can be used in the compositions of the invention in a broad concentration range. The concentration of the active compounds in the formulation is typically 0.1%-50% by weight.

Ammonium salts and phosphonium salts which, according to the invention, increase the activity of crop protection compositions comprising active compounds from the class of the haloalkoxyspirocyclic tetramic acid and tetronic acid derivatives of the formula (I) are defined by formula (III')

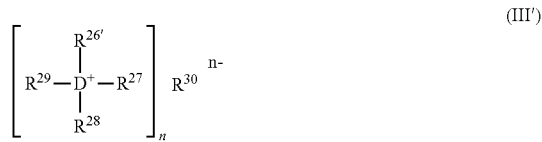

in which
D represents nitrogen or phosphorus,
D preferably represents nitrogen,
$R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26'}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano,
$R^{26'}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl,
$R^{26'}$, $R^{27}$, $R^{28}$ and $R^{29}$ very particularly preferably represent hydrogen,
n represents 1, 2, 3 or 4,
n preferably represents 1 or 2,
$R^{30}$ represents an inorganic or organic anion,
$R^{30}$ preferably represents bicarbonate, tetraborate, fluoride, bromide, iodide, chloride, monohydrogenphosphate, dihydrogenphosphate, hydrogensulfate, tartrate, sulfate, nitrate, thiosulfate, thiocyanate, formate, lactate, acetate, propionate, butyrate, pentanoate or oxalate,
$R^{30}$ particularly preferably represents lactate, sulfate, nitrate, thiosulfate, thiocyanate, oxalate or formate,
$R^{30}$ very particularly preferably represents sulfate.

Inventively emphasized combinations of active compound, salt and penetrant are listed in the table below. "Penetrant as per test" means here that any compound that acts as a penetrant in the cuticle penetration test (Baur et al., 1997, Pesticide Science 51, 131-152) is suitable.

The ammonium salts and phosphonium salts of the formula (III') can be used in a broad concentration range to increase the activity of crop protection compositions comprising ketoenols. In general, the ammonium salts or phosphonium salts are used in the ready-to-use crop protection composition in a concentration of from 0.5 to 80 mmol/l, preferably 0.75 to 37.5 mmol/l, particularly preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active compound concentration. The concentration of the salt in the formulation here is usually 1-50% by weight.

In one preferred embodiment of the invention, it is not only an ammonium salt and/or a phosphonium salt, but additionally a penetrant, that is added to the crop protection compositions to boost the activity. It is considered entirely surprising that even in these cases an even greater increase in activity is observed. The present invention therefore likewise provides for the use of a combination of penetrant and ammonium salts and/or phosphonium salts to increase the activity of crop protection compositions which comprise herbicidal and/or acaricidal and/or insecticidal, haloalkoxyspirocyclic tetramic and tetronic acid derivatives of the formula (I) as active compound. The invention likewise provides compositions which comprise herbicidal and/or acaricidal and/or insecticidal haloalkoxyspirocyclic tetramic and tetronic acid derivatives of the formula (I), penetrants and ammonium salts or phosphonium salts, including both formulated active compounds and also ready-to-use compositions (spray liquors). Finally, the invention also provides the use of these compositions for controlling harmful insects and/or spider mites.

Suitable penetrants in the present context are all those substances which are usually used for improving the penetration of agrochemical active compounds into plants. Penetrants are defined in this context by their ability to penetrate from the aqueous spray liquor and/or from the spray coating into the cuticle of the plant and thereby increase the mobility of active compounds in the cuticle. The method described in the literature (Baur et al., 1997, Pesticide Science 51, 131-152) can be used for determining this property.

Suitable penetrants are, for example, alkanol alkoxylates. Penetrants according to the invention are alkanol alkoxylates of the formula (IV')

$$R—O-(-AO)_v—R' \qquad (IV')$$

in which
R represents straight-chain or branched alkyl having 4 to 20 carbon atoms,
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or mixtures of ethylene oxide and propylene oxide radicals or butylene oxide radicals and
v represents a number from 2 to 30.

A preferred group of penetrants are alkanol alkoxylates of the formula $$R—O-(-EO—)_n—R' \qquad (IV'\text{-a})$$

in which
R has the meaning given above,
R' has the meaning given above,
EO represents —$CH_2$—$CH_2$—O— and
n represents a number from 2 to 20.

A further preferred group of penetrants are alkanol alkoxylates of the formula

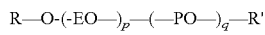 (IV'-b)

in which
R has the meaning given above,
R' has the meaning given above,
EO represents —$CH_2$—$CH_2$—O—,
PO represents

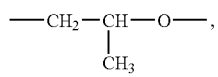

p represents a number from 1 to 10 and
q represents a number from 1 to 10.

A further preferred group of penetrants are alkanol alkoxylates of the formula

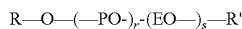 (IV'-c)

in which
R has the meaning given above,
R' has the meaning given above,
EO represents —$CH_2$—$CH_2$—O—,
PO represents

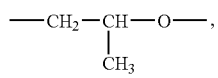

r represents a number from 1 to 10 and
s represents a number from 1 to 10.

A further preferred group of penetrants are alkanol alkoxylates of the formula

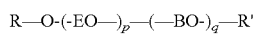 (IV'-d)

in which
R and R' have the meanings given above,
EO represents —$CH_2$—$CH_2$—O—,
BO represents

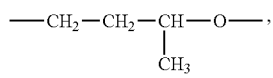

p represents a number from 1 to 10 and
q represents a number from 1 to 10.

A further preferred group of penetrants are alkanol alkoxylates of the formula

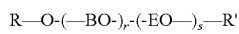 (IV'-e)

in which
R and R' have the meanings given above,
BO represents

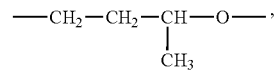

EO represents —$CH_2$—$CH_2$—O—,
r represents a number from 1 to 10 and
s represents a number from 1 to 10.

A further preferred group of penetrants are alkanol alkoxylates of the formula

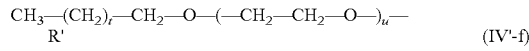 (IV'-f)

in which
R' has the meaning given above,
t represents a number from 8 to 13,
u represents a number from 6 to 17.

In the formulae given above,
R preferably represents butyl, isobutyl, n-pentyl, isopentyl, neopentyl, n-hexyl, isohexyl, n-octyl, isooctyl, 2-ethyl-hexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV-c), mention may be made of 2-ethyl-hexyl alkoxylate of the formula

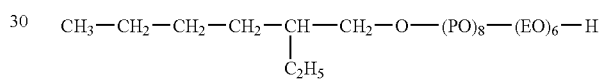 (IV'-c-1)

in which
EO represents —$CH_2$—$CH_2$—O—,
PO represent

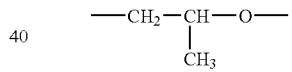

and
the numbers 8 and 6 represent average values.

As an example of an alkanol alkoxylate of the formula (IV-d), mention may be made of the formula

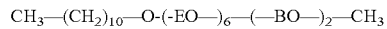 (IV'-d-1)

in which
EO represents —$CH_2$—$CH_2$—O—,
BO represents

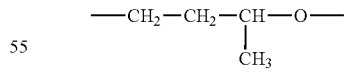

and
the numbers 10, 6 and 2 represent average values.

Particularly preferred alkanol alkoxylates of the formula (IV'-f) are compounds of this formula in which
t represents a number from 9 to 12 and
u represents a number from 7 to 9.

With very particular preference, mention may be made of alkanol alkoxylate of the formula (IV'-f-1)

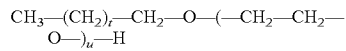 (IV'-f-1)

in which t represents the average value 10.5 and u represents the average value 8.4.

The above formulae provide general definitions of the alkanol alkoxylates. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865)

Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters.

The concentration of penetrant in the compositions of the invention can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentration is generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Mention may preferably be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and also polyoxyalkylenamine derivatives.

Suitable anionic surfactants include all substances of this type that can typically be used in agrochemical compositions. Preference is given to alkali metal salts and alkaline earth metal salts of alkylsulfonic acids or alkylarylsulfonic acids.

A further preferred group of anionic surfactants and/or dispersing assistants are the following salts that are of low solubility in vegetable oil: salts of polystyrenesulfonic acids, salts of polyvinylsulfonic acids, salts of naphthalenesulfonic acid-formaldehyde condensation products, salts of condensation products of naphthalenesulfonic acid, phenolsulfonic acid and formaldehyde, and salts of lignosulfonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulfated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, in accordance with process (A), for example ethyl N-[(4-chloro-2,6-dimethyl)-phenylacetyl]-1-amino-4-trifluoroethoxycyclohexanecarboxylate as starting material, the course of the process according to the invention can be represented by the following reaction scheme:

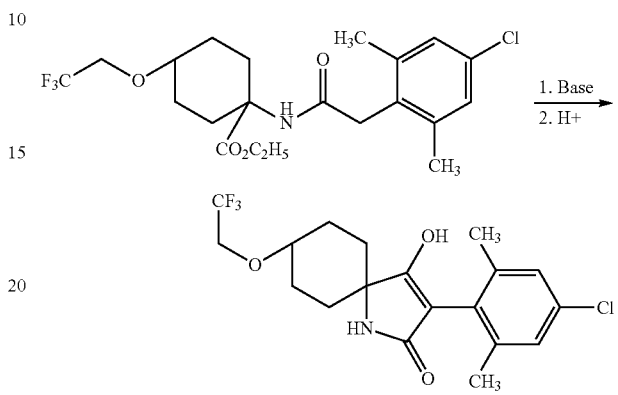

Using, in accordance with process (B), for example ethyl O-[(2-chloro-6-methyl)phenylacetyl]-1-hydroxy-4-trifluoroethoxycyclohexanecarboxylate, the course of the process according to the invention can be represented by the following reaction scheme:

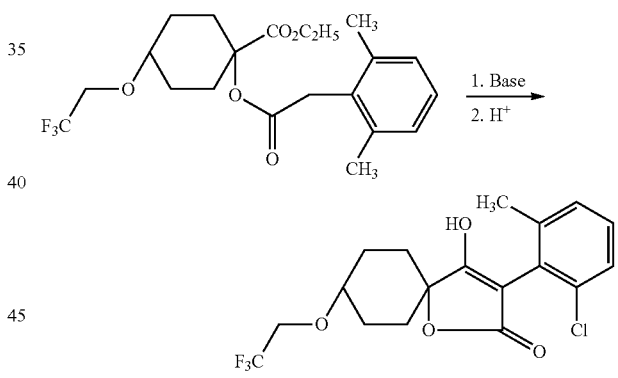

Using, in accordance with process (Cα), for example 8-trifluoroethoxy-3-[(4-chloro-2,6-dimethyl)phenyl]-1-azaspiro[4,5]decane-2,4-dione and pivaloyl chloride as starting materials, the course of the process according to the invention can be represented by the following reaction scheme:

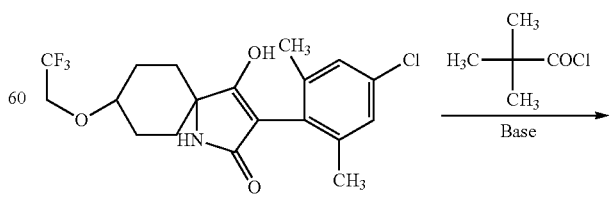

-continued

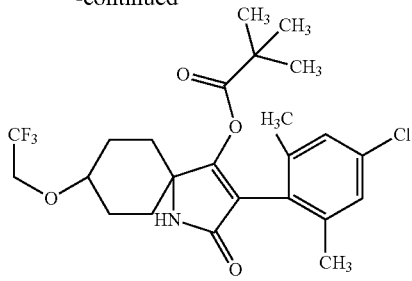

Using, in accordance with process (C) (variant β), for example 8-trifluoroethoxy-3-[(2,4-dichloro)phenyl]-1-oxaspiro[4,5]decane-2,4-dione and acetic anhydride as starting materials, the course of the process according to the invention can be represented by the following reaction scheme:

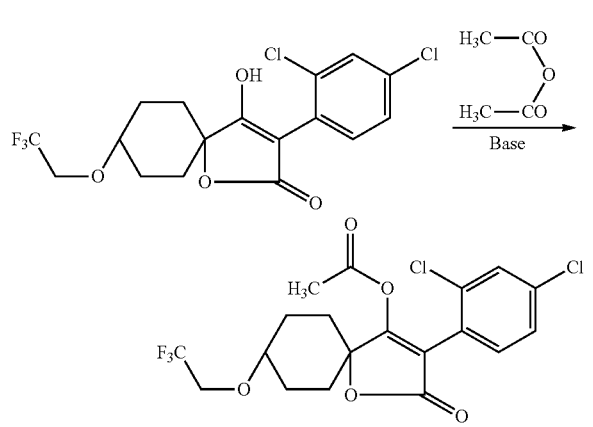

Using, in accordance with process (D), for example 8-trifluoroethoxy-3-[(2,4-dichloro-6-methyl)phenyl]-1-azaspiro[4,5]decane-2,4-dione and ethyl chloroformate as starting materials, the course of the process according to the invention can be represented by the following reaction scheme:

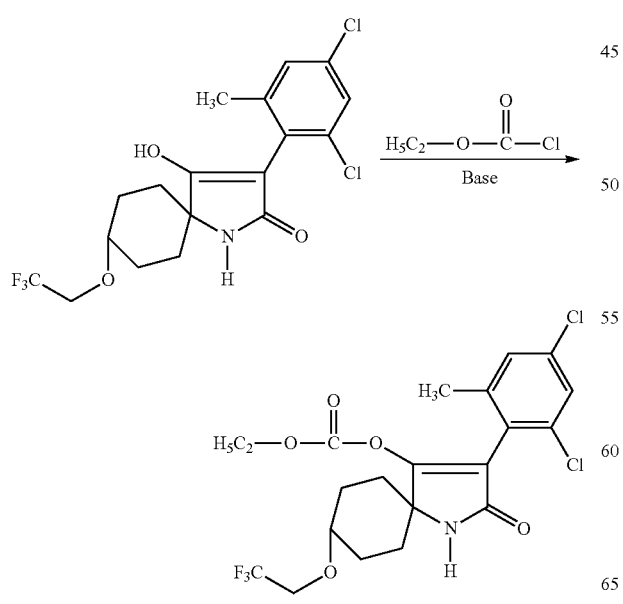

Using, in accordance with process (E), for example 8-trifluoroethoxy-3-[(2,4,6-trimethyl)phenyl]-1-oxaspiro[4,5]decane-2,4-dione and methyl chloromonothioformate as starting materials, the course of the reaction can be represented as follows:

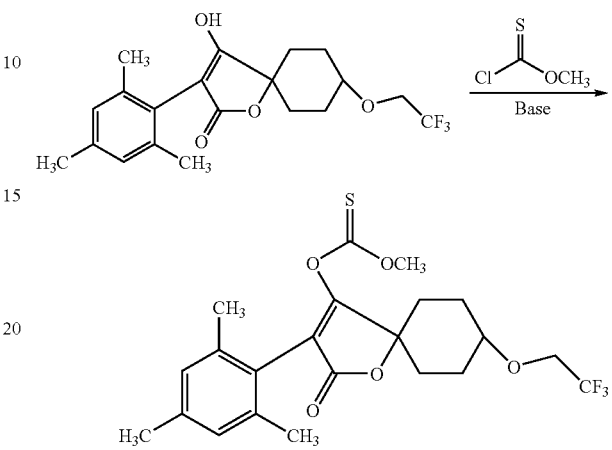

Using, in accordance with process (F), for example 8-trifluoroethoxy-3-[(2,4,6-trimethyl)phenyl]-1-azaspiro[4,5]decane-2,4-dione and methanesulfonyl chloride as starting materials, the course of the reaction can be represented by the following reaction scheme:

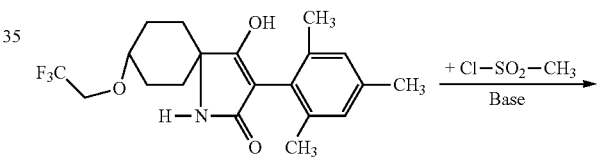

Using, in accordance with process (G), for example 8-trifluoroethoxy-3-[(2,4-dichloro-6-methyl)-phenyl]-1-oxaspiro[4,5]decane-2,4-dione and 2,2,2-trifluoroethyl methanethiophosphonyl chloride as starting materials, the course of the reaction can be represented by the following reaction scheme:

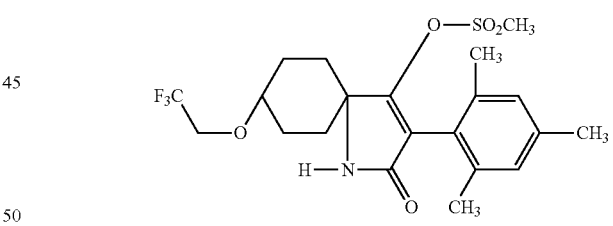

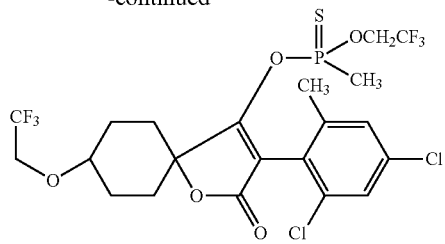

Using, in accordance with process (H), for example 8-trifluoroethoxy-3-[(2,3,4,6-tetramethylphenyl]-1-azaspiro[4,5]decane-2,4-dione and NaOH as components, the course of the process according to the invention can be represented by the following reaction scheme:

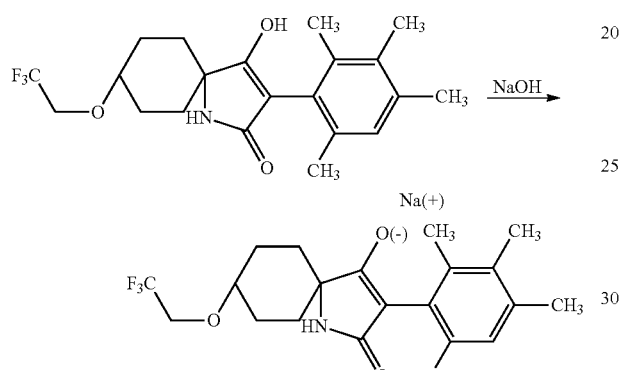

Using, in accordance with process (I) (variant α), for example 8-trifluoroethoxy-3-[(2,4,5-trimethyl)phenyl]-1-oxaspiro[4,5]decane-2,4-dione and ethyl isocyanate as starting materials, the course of the reaction can be represented by the following reaction scheme:

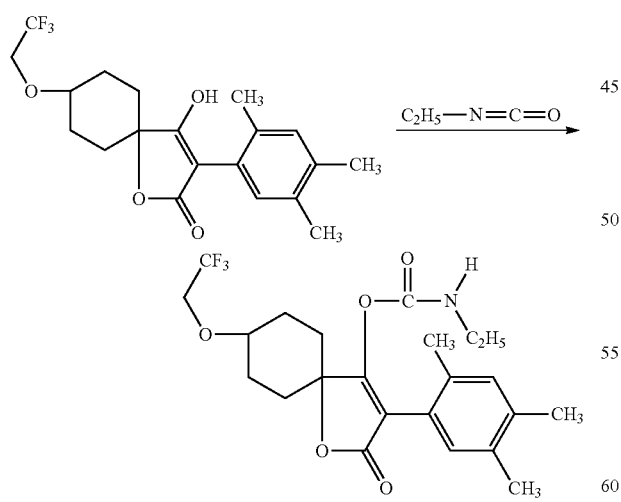

Using, in accordance with process (I) (variant β), for example 8-trifluoroethoxy-3-[(2,4,6-trimethyl)phenyl]-1-azaspiro[4,5]decane-2,4-dione and dimethylcarbamoyl chloride as starting materials, the course of the reaction can be represented by the following scheme:

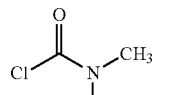
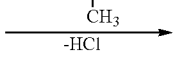

Using, in accordance with process (Jβ), for example 8-trifluoroethoxy-3-[(4-bromo-2,6-dimethyl-phenyl)]-1-azaspiro[4,5]decane-2,4-dione and 4-chlorophenylboronic acid as starting materials, the course of the reaction can be represented by the following scheme:

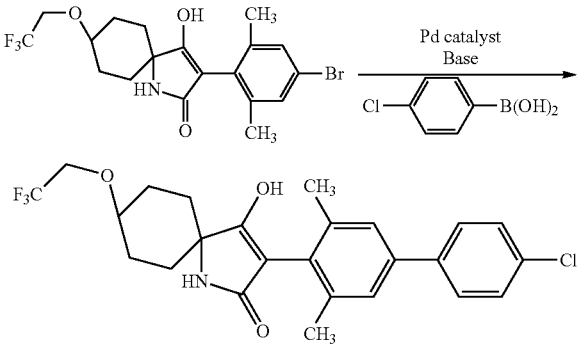

The compounds of the formula (II)

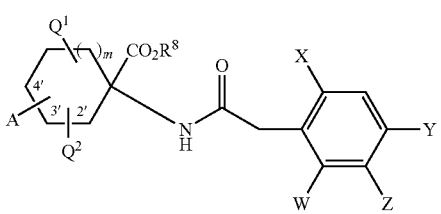

(II)

in which

A, $Q^1$, $Q^2$, m, W, X, Y, Z and $R^8$ have the meanings given above, are novel.

The acylamino acid esters of the formula (II) are obtained, for example, when amino acid derivatives of the formula (XVI)

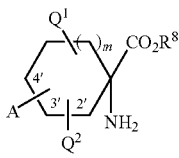

(XVI)

in which
A, m, $Q^1$ and $Q^2$ and $R^8$ have the meaning given above,
are acylated with substituted phenylacetic acid derivatives of the formula (XVII)

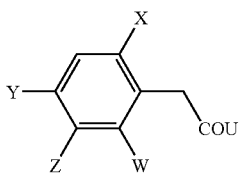

(XVII)

in which
W, X, Y and Z have the meanings given above and
U represents a leaving group introduced by reagents for the activation of carboxylic acids, such as carbonyldiimidazole, carbonyldiimides (such as, for example, dicyclohexylcarbodiimide), phosphorylating agents (such as, for example, $POCl_3$, BOP-Cl), halogenating agents, such as, for example thionyl chloride, oxalyl chloride, phosgene or chloroformic esters,
(Chem. Reviews 52, 237-416 (1953); Bhattacharya, Indian J. Chem. 6, 341-5, 1968)
or when acylamino acids of the formula (XVIII)

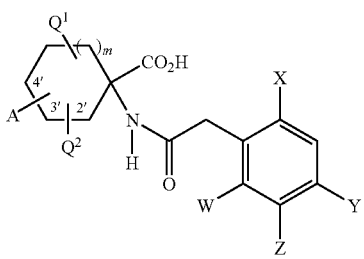

(XVIII)

in which
A, $Q^1$, $Q^2$, m, W, X, Y and Z have the meanings given above, are esterified (Chem. Ind. (London) 1568 (1968)).

The compounds of the formula (XVIII)

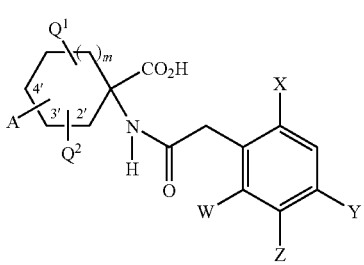

(XVIII)

in which
A, $Q^1$, $Q^2$, m, W, X, Y and Z have the meanings given above, are novel.

The compounds of the formula (XVIII) are obtained, for example, when 1-aminocyclohexane-carboxylic acids of the formula (XIX)

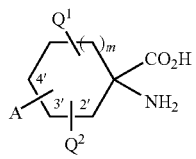

(XIX)

in which
A, m, $Q^1$ and $Q^2$ have the meanings mentioned above
are acylated with substituted phenylacetic acid derivatives of the formula (XVII)

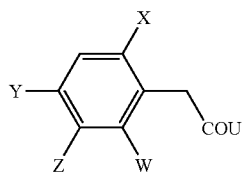

(XVII)

in which
U, W, X, Y and Z have the meanings given above and
for example following the method of Schotten-Baumann (Organikum [Organic Chemistry], VEB Deutscher Verlag der Wissenschaften, Berlin 1977, p. 505).

Some of the compounds of the formula (XVII) are known, and/or can be prepared by the known processes of the laid-open patents cited at the outset.

The compounds of the formulae (XVI) and (XIX) are novel and can be prepared by known processes (see, for example, Compagnon, Ann. Chim. (Paris) [14] 5, p. 11-22, 23-27 (1970), L. Munday, J. Chem. Soc. 4372 (1961); J. T. Eward, C. Jitrangeri, Can. J. Chem. 53, 3339 (1975)).

The novel 1-aminocyclohexanecarboxylic acids (XIX) are generally obtainable by the Bucherer-Bergs synthesis or by the Strecker synthesis and are in each case obtained in different isomer forms. For the sake of simplicity, hereinbelow the isomers in which the radical A in the 4-position and the amino group are positioned equatorial/axial or axial/equatorial are referred to as β. For the sake of simplicity, hereinbelow the isomers in which the amino group and the radical A in the 4-position are equatorial/equatorial or axial/axial are referred to as α.

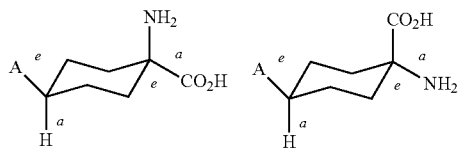

Example: β-isomer    Example: α-isomer (L. Munday, J. Chem. Soc. 4372 (1961)).

The compounds of the formula (XIX) are obtained, for example, by reacting compounds of the formula (XXIII)

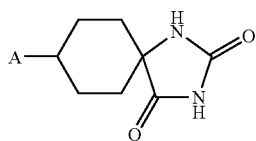

(XXIII)

in which A has the meanings given above. Some of the compounds of the formula (XXIII) are novel, and can be prepared by known processes of the laid-open patents cited at the outset.

Furthermore, the starting materials of the formula (II), used in the above process (A),

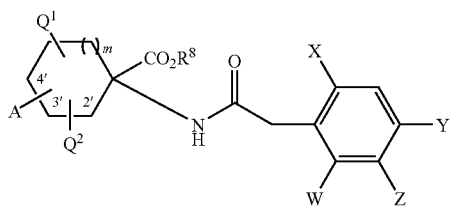

(II)

in which
A, $Q^1$, $Q^2$, m, W, X, Y, Z and $R^8$ have the meanings given above,
can be prepared by reacting 1-aminocyclohexanecarbonitriles of the formula (XX)

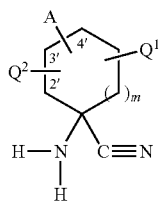

(XX)

in which
A, m, $Q^1$ and $Q^2$ have the meanings given above,
with substituted phenylacetic acid derivatives of the formula (XVII)

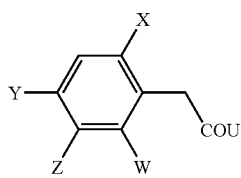

(XVII)

in which
U, W, X, Y and Z have the meanings given above,
to give compounds of the formula (XXI)

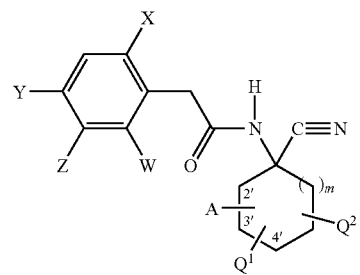

(XXI)

in which
A, m, $Q^1$, $Q^2$, W, X, Y and Z have the meanings given above,
and subsequently subjecting the latter to acid alcoholysis.

The compounds of the formula (XXI) are likewise novel. Some of the compounds of the formula (XX) are novel, and can be prepared, for example, as described in EP-A-595 130.

The compounds of the formula (III)

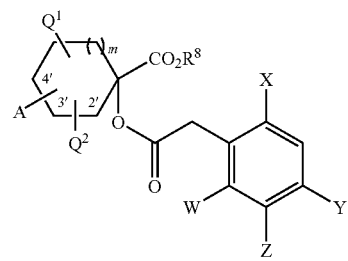

(III)

in which
A, m, $Q^1$, $Q^2$, W, X, Y, Z and $R^8$ have the meanings given above,
are novel.

They can be prepared in a simple manner by methods known in principle.

The compounds of the formula (III), for example, are obtained when 1-hydroxycyclohexanecarboxylic esters of the formula (XXII)

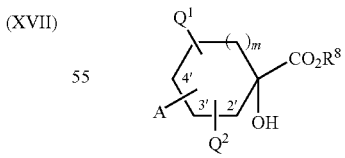

(XXII)

in which
A, m, $Q^1$, $Q^2$ and $R^8$ have the meanings given above,
are acylated with substituted phenylacetic acid derivatives of the formula (XVII)

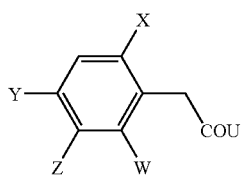

(XVII)

in which
U, W, X, Y and Z have the meanings given above,
(Chem. Reviews 52, 237-416 (1953)).

The 1-hydroxyhaloalkoxycyclohexylcarboxylic esters of the formula (XXII) are novel. They are obtained, for example, when substituted 1-hydroxyhaloalkoxycyclohexanecarbonitriles are reacted in the presence of acids, for example according to Pinner, with alcohols. The cyanohydrin is obtained, for example, by reaction of substituted haloalkoxycyclohexan-1-ones with hydrocyanic acid (see WO 99/16748).

The acyl halides of the formula (IV), carboxylic anhydrides of the formula (V), chloroformic esters or chloroformic thioesters of the formula (VI), chloromonothioformic esters or chlorodithioformic esters of the formula (VII), sulfonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII) and boronic acids of the formula (XV) furthermore required as starting materials for carrying out the processes (C), (D), (E), (F), (G), (H), (I) and (J) according to the invention are generally known compounds from organic and inorganic chemistry.

In addition, the compounds of the formulae (XVII), (I-1-a'-I-2-g') and (I-1-a"-I-2-g") are known from the patent applications cited at the outset, and/or they can be prepared by the methods given in these publications.

The process (A) is characterized in that compounds of the formula (II) in which A, $Q^1$, $Q^2$, m, W, X, Y, Z and $R^8$ have the meanings given above are subjected to an intramolecular condensation in the presence of a diluent and in the presence of a base.

Suitable diluents for the process (A) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)-amine). Alkali metals such as sodium or potassium can furthermore be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperature can be varied within a relatively wide range. In general, the process is carried out at temperatures between −75° C. and 200° C., preferably between −50° C. and 150° C.

Process (A) according to the invention is generally carried out under atmospheric pressure.

When carrying out the process (A) according to the invention, the reaction component of the formula (II) and the deprotonating base are generally employed in equimolar to approximately double-equimolar amounts. However, it is possible to use one or the other reactants in a larger excess (up to 3 mol).

Suitable diluents for the process (B) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methyl-pyrrolidone. It is also possible to employ alcohols, such as methanol, ethanol, propanol, isopropanol, butanol, isobutanol and tert-butanol.

Bases (deprotonating agents) which can be employed when carrying out process (B) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)-amine). Alkali metals such as sodium or potassium can furthermore be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (B) according to the invention, the reaction temperature can be varied within a relatively wide range. In general, the process is carried out at temperatures between −75° C. and 200° C., preferably between −50° C. and 150° C.

Process (B) according to the invention is generally carried out under atmospheric pressure.

When carrying out process (B) according to the invention, the reactants of the formula (II) and the deprotonating bases are generally employed in approximately twice the equimolar amounts. However, it is possible to use either reactant in a larger excess (up to 3 mol).

The process ($C_\alpha$) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for the process ($C_\alpha$) according to the invention are all solvents which are inert to the acyl halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulfoxide and sulfolane. If the acid halide is sufficiently stable to hydrolysis, the reaction may also be carried out in the presence of water.

Suitable acid binders for the reaction according to the process ($C_\alpha$) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig Base and N,N-dimethyl-anilin, furthermore alkali metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

The reaction temperature in the process ($C_\alpha$) according to the invention can be varied within a relatively wide range. In general, the process is carried out at temperatures between $-20°$ C. and $+150°$ C., preferably between $0°$ C. and $100°$ C.

When carrying out the process ($C_\alpha$) according to the invention, the starting materials of the formulae (I-1-a) to (I-2-a) and the carbonyl halide of the formula (IV) are generally in each case employed in approximately equivalent amounts. However, it is also possible to employ the carboxylic acid halides in a larger excess (of up to 5 mol). Work-up is carried out by customary methods.

The process ($C_\beta$) is characterized in that compounds of the formulae (I-1-a) to (I-2-a) are in each case reacted with carboxylic anhydrides of the formula (V), if appropriate in the presence of a diluent and if appropriate in the presence of an acid binder.

Preferred diluents for the process ($C_\beta$) according to the invention are those diluents which are also preferred when acyl halides are used. Besides, a carboxylic anhydride used in excess may also simultaneously act as the diluent.

In the process ($C_\beta$), acid binders which are added, if appropriate, are preferably those acid binders which are also preferred when acyl halides are used.

In the process ($C_\beta$) according to the invention, the reaction temperature can be varied within a relatively wide range. In general, the process is carried out at temperatures between $-20°$ C. and $+150°$ C., preferably between $0°$ C. and $100°$ C.

When carrying out the process ($C_\beta$) according to the invention, the starting materials of the formulae (I-1-a) to (I-2-a) and the carboxylic anhydride of the formula (V) are generally each employed in approximately equivalent amounts. However, it is also possible to employ the carboxylic anhydride in a larger excess (of up to 5 mol). Work-up is carried out by customary methods.

In general, a procedure is followed in which diluent, excess carboxylic anhydride and the carboxylic acid which forms are removed by distillation or by washing with an organic solvent or with water.

Process (D) is characterized in that compounds of the formulae (I-1-a) to (I-2-a) are reacted in each case with chloroformic esters or chloroformic thioesters of the formula (VI), if appropriate in the presence of a diluent and if appropriate in the presence of an acid binder.

Suitable acid binders for the reaction according to the invention are all customary acid acceptors. Preference is given to using tertiary amines, such as triethylamine, pyridine, DABCO, DBU, DBN, Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Diluents which can be employed in process (D) according to the invention are all solvents which are inert to the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethylformamide, dimethyl sulfoxide and sulfolane.

When carrying out the process (D) according to the invention, the reaction temperature can be varied within a relatively wide range. The reaction temperature is generally between $-20°$ C. and $+100°$ C., preferably between $0°$ C. and $50°$ C.

Process (D) according to the invention is generally carried out under atmospheric pressure.

When carrying out process (D) according to the invention, the starting materials of the formulae (I-1-a) to (I-2-a) and the corresponding chloroformic ester or chloroformic thioester of the formula (VI) are generally used in each case in approximately equivalent amounts. However, it is also possible to employ one or the other reactant in a larger excess (of up to 2 mol). Work-up is carried out by customary methods. In general, a procedure is followed in which the salts which have precipitated are removed and the reaction mixture which remains is concentrated by stripping off the diluent.

Process (E) according to the invention is characterized in that compounds of the formulae (I-1-a) to (I-2-a) are reacted in each case with compounds of the formula (VII) in the presence of a diluent and, if appropriate, in the presence of an acid binder.

In preparation process (E), approximately 1 mol of chloromonothioformic ester or chlorodithioformic ester of the formula (VII) is reacted at from 0 to $120°$ C., preferably at from 20 to $60°$ C., per mole of starting compound of the formulae (I-1-a) to (I-2-a).

Suitable diluents which are added, if appropriate, are all inert polar organic solvents, such as ethers, amides, sulfones, sulfoxides, but also haloalkanes.

Preference is given to using dimethyl sulfoxide, tetrahydrofuran, dimethylformamide, ethyl acetate or methylene chloride.

If, in a preferred embodiment, the enolate salt of the compounds (I-1-a) to (I-2-a) by addition of strong deprotonating agents such as, for example, sodium hydride or potassium tertiary-butylate, the further addition of acid binders can be dispensed with.

Suitable bases for the process (E) are all customary proton acceptors. Preference is given to using alkali metal hydrides, alkali metal alkoxides, alkali metal or alkaline earth metal carbonates or bicarbonates or nitrogen bases. Examples which may be mentioned are sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out under atmospheric pressure or under elevated pressure, preferably under atmospheric pressure. Work-up is carried out by customary methods.

Process (F) according to the invention is characterized in that compounds of the formulae (I-1-a) to (I-2-a) are reacted in each case with sulfonyl chloride of the formula (VIII), if appropriate in the presence of a diluent and if appropriate in the presence of an acid binder.

In preparation process (F), about 1 mol of sulfonyl chloride of the formula (VIII) is reacted per mole of starting material of the formulae (I-1-a) to (I-2-a), at from −20 to 150° C., preferably at from 0 to 70° C.

The process (F) is preferably carried out in the presence of a diluent.

Suitable diluents are all inert polar organic solvents, such as ethers, amides, ketones, carboxylic esters, nitriles, sulfones, sulfoxides or halogenated hydrocarbons, such as methylene chloride.

Preference is given to using dimethyl sulfoxide, tetrahydrofuran, dimethylformamide, ethyl acetate or methylene chloride.

If, in a preferred embodiment, the enolate salt of the compounds (I-1-a) to (I-2-a) is synthesized by addition of strong deprotonating agents (such as, for example, sodium hydride or potassium tertiary-butoxide), the further addition of acid binders can be dispensed with.

If acid binders are employed, these are customary inorganic or organic bases, for example sodium hydroxide, sodium carbonate, potassium carbonate, pyridine and triethylamine.

The reaction can be carried out under atmospheric pressure or under elevated pressure, preferably under atmospheric pressure. Work-up is carried out by customary methods.

Process (G) according to the invention is characterized in that compounds of the formulae (I-1-a) to (I-2-a) are reacted in each case with phosphorus compounds of the formula (IX), if appropriate in the presence of a diluent and if appropriate in the presence of an acid binder.

In preparation process (G), 1 to 2, preferably 1 to 1.3, mole of the phosphorus compound of the formula (IX) are reacted at temperatures of between −40° C. and 150° C., preferably between −10 and 110° C., per mole of the compounds (I-1-a) to (I-2-a) in order to obtain compounds of the formulae (I-1-e) to (I-2-e).

The process (G) is preferably carried out in the presence of a diluent.

Suitable diluents are all inert polar organic solvents, such as ethers, carboxylic esters, halogenated hydrocarbons, ketones, amides, nitriles, sulfones, sulfoxides, etc.

Substances which are preferably employed are acetonitrile, dimethyl sulfoxide, tetrahydrofuran, dimethylformamide, methylene chloride.

Suitable acid binders which are optionally added are customary inorganic or organic bases such as hydroxides, carbonates or amines. Examples include sodium hydroxide, sodium carbonate, potassium carbonate, pyridine and triethylamine.

The reaction can be carried out under atmospheric pressure or under elevated pressure, preferably under atmospheric pressure. Work-up is carried out by customary methods of organic chemistry. The end products are preferably purified by crystallization, chromatographic purification or "incipient distillation", i.e. removal of the volatile components under reduced pressure.

The process (H) is characterized in that compounds of the formulae (I-1-a) to (I-2-a) are in each case reacted with metal hydroxides or metal alkoxides of the formula (X) or amines of the formula (XI), if appropriate in the presence of a diluent.

Preferred diluents for the process (H) according to the invention are ethers, such as tetrahydrofuran, dioxane, diethyl ether, or else alcohols, such as methanol, ethanol, isopropanol, but also water. Process (H) according to the invention is generally carried out under atmospheric pressure. The reaction temperature is generally between −20° C. and 100° C., preferably between 0° C. and 50° C.

The process (I) according to the invention is characterized in that compounds of the formulae (I-1-a) to (I-2-a) are in each case reacted with (Iα) compounds of the formula (XII), if appropriate in the presence of a diluent and if appropriate in the presence of a catalyst, or (Iβ) with compounds of the formula (XIII), if appropriate in the presence of a diluent and if appropriate in the presence of an acid binder.

In the preparation process (Iα), approximately 1 mol of isocyanate of the formula (XII) is reacted per mole of starting material of the formulae (I-1-a) to (I-2-a), at from 0 to 100° C., preferably at from 20 to 50° C.

The process (Iα) is preferably carried out in the presence of a diluent.

Suitable diluents are all inert organic solvents, such as aromatic hydrocarbons, halogenated hydrocarbons, ethers, amides, nitriles, sulfones or sulfoxides.

If appropriate, catalysts may be added to accelerate the reaction. Catalysts which can be employed very advantageously are organotin compounds such as, for example, dibutyltin dilaurate.

The process is preferably carried out under atmospheric pressure.

In the preparation process (Iβ), approximately 1 mol of carbamoyl chloride of the formula (XIII) is reacted per mole of starting material of the formulae (I-1-a) to (I-2-a), at from 0 to 150° C., preferably at from 20 to 70° C.

Suitable diluents which are added, if appropriate, are all inert polar organic solvents, such as ethers, carboxylic esters, nitriles, ketones, amides, sulfones, sulfoxides or halogenated hydrocarbons.

Preference is given to using dimethyl sulfoxide, tetrahydrofuran, dimethylformamide or methylene chloride.

If, in a preferred embodiment, the enolate salt of the compound (I-1-a) to (I-2-a) is synthesized by adding strong deprotonating agents (such as, for example, sodium hydride or potassium tertiary-butoxide), the further addition of acid binders can be dispensed with.

If acid binders are employed, these are customary inorganic or organic bases, for example sodium hydroxide, sodium carbonate, potassium carbonate triethylamine or pyridine.

The reaction can be carried out under atmospheric pressure or under elevated pressure, preferably under atmospheric pressure. Work-up is carried out by customary methods.

Suitable catalysts for carrying out the processes (Jα) and (Jβ) according to the invention are palladium(0) complexes. Preference is given, for example, to tetrakis(triphenylphosphine)palladium. If appropriate, it is also possible to use palladium(II) compounds, for example $PdCl_2$, $Pd(OAc)_2$. If palladium(II) compounds are used, phosphines, such as, for example, tricyclohexylphosphine, are generally employed as complex formers.

Suitable acid acceptors for carrying out the processes (Jα) and (Jβ) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate, cesium carbonate or ammonium carbonate, sodium bicarbonate or potassium bicarbonate, alkali metal fluorides, such as, for example, cesium fluoride, alkali metal phosphates, such as, for example, potassium dihydrogen phosphate, potassium phosphate and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the processes (Jα) and (Jβ) according to the invention are water, organic solvents and any mixtures thereof. There may be mentioned by way of example: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monomethyl ether; water.

In the processes (Jα) and (Jβ) according to the invention, the reaction temperature can be varied within a relatively wide range. In general, the process is carried out at temperatures between 0° C. and +140° C., preferably between 50° C. and +100° C.

When carrying out the processes (Jα) and (Jβ) according to the invention, the boronic acids of the formulae (XVα) and (XVβ) in which Y and Z have the meaning given above and compounds of the formulae (I-1-a') to (I-2-g') in which A, D, G, $Q^1$, $Q^2$, W, X, Y and Z' have the meaning given above and the compounds of the formulae (I-1-a") to (I-2-g") in which A, D, G, $Q^1$, $Q^2$, m, W, X, Z and Y' have the meaning given above are employed in a molar ratio of from 1:1 to 3:1, preferably of from 1:1 to 2:1. In general, from 0.005 to 0.5 mol, preferably from 0.01 mol to 0.1 mol, of catalyst are employed per mole of the compounds of the formulae (I-1-a') to (I-2-g') or (I-1-a") to (I-2-g"). The base is generally employed in excess. Work-up is carried out by customary methods.

The active compounds according to the invention, in combination with good plant tolerance, favourable toxicity to warm-blooded animals and being tolerated well by the environment, are suitable for protecting plants and plant organs, for increasing harvest yields, for improving the quality of harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus carpophagus* and *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Steprnechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the *Dermaptera*, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella*

*nativa, Trichinella britovi, Trichinella nelsoni, Trichinella pseudopsiralis, Trichostrongulus* spp., *Trichuris trichuria, Wuchereria bancrofti.*

It is furthermore possible to control Protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonic* and *Vespa* spp.

From the order of the Isopoda, for example, *Armadillidium vulgare, Oniscus asellus* and *Porcellio scaber.*

From the order of the Isoptera, for example, *Reticulitermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Theimesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp. and *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (Rickettsia-like organisms). If appropriate, they can also be used as intermediates or precursors for the synthesis of other active compounds.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injecting, and, in the case of propagation material, in particular in the case of seeds, also by applying one or more coats.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, that is, liquid solvents, and/or solid carriers, optionally with the use of surfactants, that is to say emulsifiers and/or dispersants, and/or foam-formers. The formulations are prepared either in suitable plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

Suitable Solid Carriers are:
for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite, dolomite, and also synthetic granules of inorganic and organic meals, and granules of organic material such as paper, sawdust, coconut shells, corn cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be present in its commercially available formulations and in the use foams, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of plant parts or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" and "parts of plants" or "plant parts" have been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus possible are, for example, reduced application rates and/or a widening of the activity spectrum and/or an increase of the activity of the compounds and compositions which can be used according to the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processibility of the harvested products, which exceed the effects normally to be expected.

The transgenic plants or plant cultivars (i.e. those obtained by genetical engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), corn, soybeans, potatoes, sugar beets, tomatoes, peas and other types of vegetable, cotton, tobacco, oilseed rape and also fruit plants (with the fruits apples, pears, citrus fruits and grapes), with particular emphasis being given to corn, soybeans, potatoes, cotton, tobacco and oilseed rape. Traits that are emphasized in particular are increased defense of the plants against insects, arachnids, nematodes and molluscs by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are corn varieties, cotton varieties, soybean varieties and potato varieties which are sold under the trade names YIELD GARD® (for example corn, cotton, soybeans), KnockOut® (for example corn), StarLink® (for example corn), Bollgard® (cotton), Nucotn® (cotton) and NewLeaf® (potato). Examples of herbicide-tolerant plants which may be mentioned are corn varieties, cotton varieties and soybean varieties which are sold under the trade names Roundup Ready® (tolerance to glyphosate, for example corn, cotton, soybean), Liberty Link® (tolerance to phosphinotricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include the varieties sold under the name Clearfield® (for example corn). Of course, these statements also apply to plant cultivars having these genetic traits or genetic traits still to be developed, which plants will be developed and/or marketed in the future.

The plants stated can be treated particularly advantageously in accordance with the invention with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis*, *Periplaneta americana*, *Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp.,

*Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing, powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

It has furthermore been found that the compounds according to the invention also have a strong insecticidal action against insects which destroy industrial materials.

The following insects may be mentioned as examples and as preferred—but without a limitation:
beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticuliteimes lucifugus, Mastoteiiues darwiniensis, Zootermopsis nevadensis, Coptotermes formosanus;*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

The ready-to-use compositions can also comprise other insecticides, if appropriate, and also one or more fungicides, if appropriate.

With respect to additional partners for mixing, reference is made to the insecticides and fungicides mentioned above.

The compounds according to the invention can at the same time be employed for protecting objects which come into contact with saltwater or brackish water, such as hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Avicularüdae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp.,

*Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, especially, as weedkillers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The according to the invention have strong herbicidal activity and a broad active spectrum when used on the soil and on above-ground plant parts. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is to say, emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite, dolomite, and also synthetic granules of inorganic and organic meals, and granules of organic material such as sawdust, coconut shells, corn cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

A mixture with other known active compounds, such as fungicides, insecticides, acaricides, nematicides, bird repellents, plant nutrients and agents which improve soil structure, is also possible.

The active compounds or active compound combinations can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds or active compound combinations according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular in the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form of their formulations or in the use forms prepared therefrom by further dilution, such as ready-to-use solutions, suspensions, emulsions, powders, pastes and granules. They are used in a customary manner, for example by watering, spraying, atomizing, dusting or broadcasting.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), corn, soybeans, potatoes, cotton, oilseed rape, beet, sugar cane and also fruit plants (with the fruits apples, pears, citrus fruits and grapevines), greater emphasis being given to cereals, corn, soybeans, potatoes, cotton and oilseed rape.

The term "active compounds" always also includes the active compound combinations mentioned here.

The preparation and the use of the active compounds according to the invention is illustrated by the examples below.

PREPARATION EXAMPLES

Example I-1-a-1

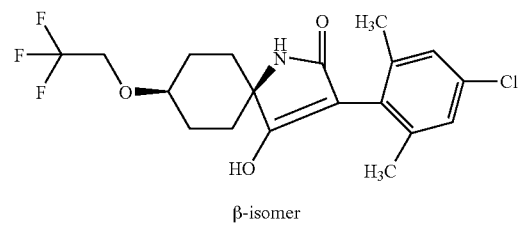 [SMILES: Cc1cc(Cl)cc(C)c1C1=C(O)[C@]2(CC[C@H](OCC(F)(F)F)CC2)NC1=O]

β-isomer

Under argon, 2.98 g of potassium tert-butoxide (95%) are initially charged in 10 ml of dimethylacetamide. At 40° C., 4.4 g of the compound of Example II-1 in 10 ml dimethylacetamide are added dropwise. The mixture is stirred at 40° C. for 4 h. After the reaction has ended (monitored by TLC) the mixture is stirred into 400 ml of ice-water, adjusted to pH 2 using conc. HCl and filtered off with suction. This is followed by purification by column chromatography on silica gel (methylene chloride/ethyl acetate 3:1).

Yield: 1.4 g (34% of theory), m.p. 262° C.

The following compounds of the formula (I-1-a) where $Q^1$ and $Q^2$=H and m=1 are obtained analogously to Example (I-1-a-1) and following the general preparation instructions

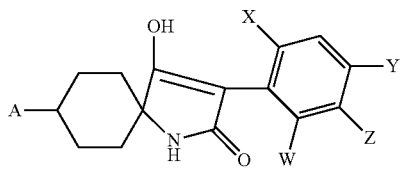

(I-1-a)

| Ex. No. | W | X | Y | Z | A | M.p. °C. | Isomer |
|---|---|---|---|---|---|---|---|
| I-1-a-2 | C₂H₅ | Br | CH₃ | H | —O—CH₂—CF₃ | 128 | α:β 2:7 |
| I-1-a-3 | CH₃ | CH₃ | H | 4-F—Ph | —O—CH₂—CF₃ | 280 | β |
| I-1-a-4 | C₂H₅ | OCH₃ | Cl | H | —O—CH₂—CF₃ | 189 | α:β 1:2 |
| I-1-a-5 | CH₃ | CH₃ | CH₃ | H | —O—CH₂—CF₃ | 203 | α:β 5:9 |
| I-1-a-6 | CH₃ | CH₃ | H | 4-F—Ph | —O—CH₂—CF₃ | 260 | α |
| I-1-a-7 | C₂H₅ | Br | CH₃ | H | —O—CH₂—CF₃ | 111 | α |
| I-1-a-8 | H | CH₃ | Cl | H | —O—CH₂—CF₃ | 210 | α:β about 1:9 |
| I-1-a-9 | CH₃ | CH₃ | Br | H | —O—CH₂—CF₃ | 269 | β |
| I-1-a-10 | H | CH₃ | H | H | —O—CH₂—CF₃ | 217 | α:β about 1:7.5 |
| I-1-a-11 | H | CH₃ | H | CH₃ | —O—CH₂—CF₃ | 212 | β |
| I-1-a-12 | C₂H₅ | C₂H₅ | CH₃ | H | —O—CH₂—CF₃ | 174 | β |
| I-1-a-13 | C₂H₅ | CH₃ | CH₃ | H | —O—CH₂—CF₃ | 176 | β |
| I-1-a-14 | C₂H₅ | O—C₂H₅ | Cl | H | —O—CH₂—CF₃ | 169 | β |
| I-1-a-15 | C₂H₅ | O—C₂H₅ | Cl | H | —O—CH₂—CF₃ | 106 | α |
| I-1-a-16 | CH₃ | CH₃ | CH₃ | CH₃ | —O—CH₂—CF₃ | 254 | β |
| I-1-a-17 | CH₃ | CH₃ | CH₃ | CH₃ | —O—CH₂—CF₃ | 243 | α |
| I-1-a-18 | H | Cl | H | 4-Cl—Ph | —O—CH₂—CF₃ | 247 | α |
| I-1-a-19 | H | Cl | H | 4-Cl—Ph | —O—CH₂—CF₃ | 226 | β |
| I-1-a-20 | H | Cl | H | 4-F—Ph | —O—CH₂—CF₃ | 247 | α |
| I-1-a-21 | H | Cl | H | 4-F—Ph | —O—CH₂—CF₃ | >300 | β |
| I-1-a-22 | CH₃ | OCH₃ | Cl | H | —O—CH₂—CF₃ | 167 | β |
| I-1-a-23 | CH₃ | OCH₃ | Cl | H | —O—CH₂—CF₃ | wax | α |
| I-1-a-24 | CH₃ | CH₃ | H | 4-Cl—Ph | —O—CH₂—CF₃ | 273 | α |
| I-1-a-25 | CH₃ | CH₃ | H | 4-Cl—Ph | —O—CH₂—CF₃ | 288 | β |
| I-1-a-26 | H | CH₃ | CH₃ | CH₃ | —O—CH₂—CF₃ | 126 | α |
| I-1-a-27 | H | CH₃ | CH₃ | CH₃ | —O—CH₂—CF₃ | 220 | β |
| I-1-a-28 | CH₃ | CH₃ | Cl | H | —O—CH₂—CF₂—CF₃ | * | α |
| I-1-a-29 | CH₃ | CH₃ | Cl | H | —O—CH₂—CF₂—CF₃ | 202 | β |
| I-1-a-30 | CH₃ | CH₃ | cyclopropyl | H | —O—CH₂—CF₃ | 281 | β |
| I-1-a-31 | H | CH₃ | H | 4-F—Ph | —O—CH₂—CF₃ | 140 | α + β about 1:2 |
| I-1-a-32 | H | CH₃ | H | CH₃ | —O—CH₂—CF₂—CF₃ | 200 | β |

¹H-NMR (400 MHz, d₆-DMSO): δ = 1.21-1.24 (dm, 2H, CH₂), 2.08 (s, 6H, Ar—CH₃), 3.75 (zm, 1H, CH—OCH₂CF₃), 4.05-4.12 (dt, 2H, OCH₂CF₃), 7.08 (s, 2H, Ar—H) ppm.

Example I-1-b-1

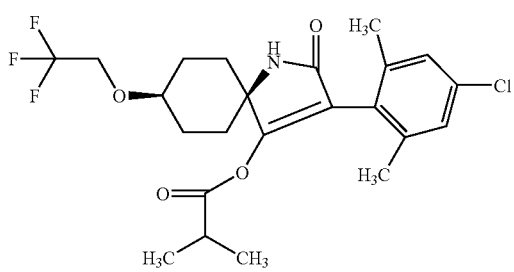 [SMILES: Cc1cc(Cl)cc(C)c1C1=C(OC(=O)C(C)C)[C@]2(CC[C@H](OCC(F)(F)F)CC2)NC1=O]

β-isomer

Under argon, 0.4 g of the compound of Example I-1-a-1 (0.001 mol) is initially charged in 20 ml of ethyl acetate (anhydrous) and 0.1 g of triethylamine (0.14 ml). 10 mg of Steglich base are used as catalyst; 0.11 g of isobutyryl chloride (0.001 mol) in 3 ml of ethyl acetate (anhydrous) is added dropwise at 70° C. The mixture is stirred at 70° C. for 1 h. After concentration, the product is purified by column chromatography on silica gel (dichloromethane: ethyl acetate=10:1)

Yield: 0.25 g (52% of theory), m.p. 219° C.

The following compounds of the formula (I-1-b) where Q¹ and Q²=H and m=1 are obtained analogously to Example (I-1-b-1) and following the general preparation instructions

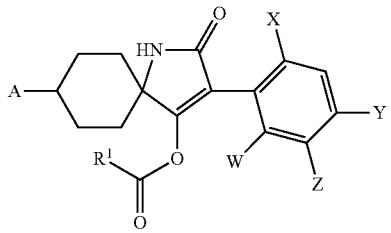

(I-1-b)

| Ex. No. | W | X | Y | Z | A | R¹ | m.p. °C. | Isomer |
|---|---|---|---|---|---|---|---|---|
| I-1-b-2 | CH₃ | CH₃ | H | 4-F—Ph | O—CH₂—CF₃ | i-C₃H₇ | 210 | β |
| I-1-b-3 | C₂H₅ | OCH₃ | Cl | H | O—CH₂—CF₃ | CH₃ | 204-206 | β |

Example I-1-c-1

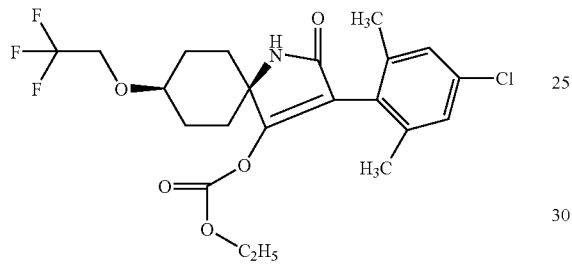

β-isomer

Under argon, 0.4 g of the compound of Example I-1-a-1 (0.001 mol) is initially charged in 20 ml of methylene chloride (anhydrous) and 0.1 g of triethylamine (0.14 ml). 10 mg of Steglich base are used as catalyst; 0.1 ml of ethyl chloroformate (0.001 mol) in 3 ml of methylene chloride (anhydrous) is added dropwise at 20° C. The mixture is stirred at 20° C. for 1 h. After concentration, the product is purified by column chromatography on silica gel (dichloromethane: ethyl acetate=10:1).

Yield: 0.3 g (62.6% of theory), m.p. 174° C.

The following compounds of the formula (I-1-c) where $Q^1$ and $Q^2$=H and m=1 are obtained analogously to Example (I-1-c-1) and following the general preparation instructions Example II-1

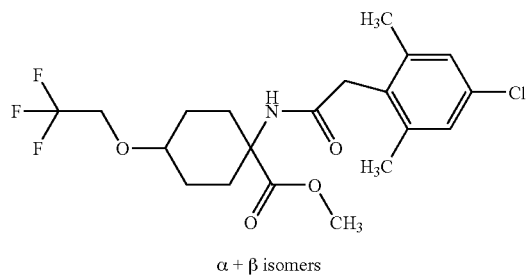

α + β isomers

Under argon, 3.2 g of the compound of Example XVI-1 are initially charged in 30 ml of ethyl acetate. 11 ml of 1N NaOH are added. At 0-5° C., 10 ml of 1N NaOH and 2.17 g of 4-chloro-2,6-dimethylphenylacetyl chloride in 10 ml of ethyl acetate are simultaneously added dropwise. The mixture is stirred for another 1 h. The aqueous phase is separated off and extracted with methylene chloride. The combined organic phases are washed with NaHCO₃ solution, dried with magnesium sulfate and concentrated on a rotary evaporator. Purification is carried out on silica gel using the mobile phase magnesium sulfate.

Yield: 4.5 g (80% of theory), m.p. 162° C.

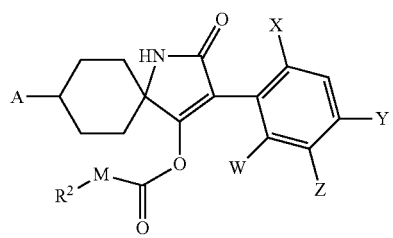

| Ex. No. | W | X | Y | Z | A | M | R² | m.p. °C. | Isomer |
|---|---|---|---|---|---|---|---|---|---|
| I-1-c-2 | CH₃ | CH₃ | H | 4-F—Ph | —O—CH₂—CF₃ | O | CH₃ | 196 | β |
| I-1-c-3 | C₂H₅ | Br | CH₃ | H | —O—CH₂—CF₃ | O | C₂H₅ | 204-206 | β |

The following compounds of the formula (II) where $Q^1$ and $Q^2$=H and m=1 are obtained analogously to Example (II-1) and following the general preparation instructions

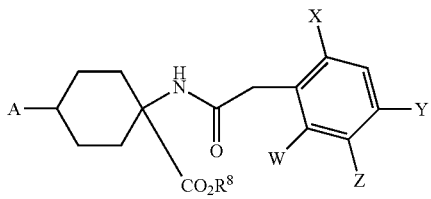

(II)

| Ex. No. | W | X | Y | Z | A | $R^8$ | M.p. ° C. | Isomer |
|---|---|---|---|---|---|---|---|---|
| II-2 | $CH_3$ | $CH_3$ | $CH_3$ | H | —O—$CH_2$—$CF_3$ | $CH_3$ | 160 | α + β mixture |
| II-3 | $CH_3$ | $CH_3$ | H | 4-F—Ph | —O—$CH_2$—$CF_3$ | $CH_3$ | 139 | α + β mixture |
| II-4 | $C_2H_5$ | $OCH_3$ | Cl | H | —O—$CH_2$—$CF_3$ | $CH_3$ | 136 | α + β mixture |
| II-5 | $C_2H_5$ | Br | 4-$CH_3$ | H | —O—$CH_2$—$CF_3$ | $CH_3$ | 138 | α + β mixture |
| II-6 | H | $CH_3$ | H | $CH_3$ | —O—$CH_2$—$CF_3$ | $CH_3$ | 151 | α + β mixture |
| II-7 | H | $CH_3$ | Cl | H | —O—$CH_2$—$CF_3$ | $CH_3$ | 155 | α + β mixture |
| II-8 | H | $CH_3$ | H | H | —O—$CH_2$—$CF_3$ | $CH_3$ | 130 | α + β mixture |
| II-9 | $CH_3$ | $CH_3$ | Br | H | —O—$CH_2$—$CF_3$ | $CH_3$ | 174 | α + β mixture |
| II-10 | $CH_3$ | $CH_3$ | $CH_3$ | H | —O—$CH_2$—$CF_2$—$CF_3$ | $CH_3$ | 143 | α + β mixture |
| II-11 | $CH_3$ | $C_2H_5$ | $CH_3$ | H | —O—$CH_2$—$CF_3$ | $CH_3$ | 130 | α + β mixture |
| II-12 | $CH_3$ | $OCH_3$ | Cl | H | —O—$CH_2$—$CF_3$ | $CH_3$ | 160 | α + β mixture |
| II-13 | $C_2H_5$ | $C_2H_5$ | $CH_3$ | H | —O—$CH_2$—$CF_3$ | $CH_3$ | 143 | α + β mixture |
| II-14 | $CH_3$ | $CH_3$ | $CH_3$ | $CH_3$ | —O—$CH_2$—$CF_3$ | $CH_3$ | 165 | α + β mixture |
| II-15 | $C_2H_5$ | $OC_2H_5$ | Cl | H | —O—$CH_2$—$CF_3$ | $CH_3$ | 152 | α + β mixture |
| II-16 | $CH_3$ | $CH_3$ | cyclopropyl | H | —O—$CH_2$—$CF_3$ | $CH_3$ | 135 | α + β mixture |
| II-17 | H | Cl | H | 4-F—Ph | —O—$CH_2$—$CF_3$ | $CH_3$ | 131 | α + β mixture |
| II-18 | H | $CH_3$ | H | 4-Cl—Ph | —O—$CH_2$—$CF_3$ | $CH_3$ | 152 | α + β mixture |
| II-19 | $CH_3$ | $CH_3$ | H | 4-Cl—Ph | —O—$CH_2$—$CF_3$ | $CH_3$ | 188 | α + β mixture |
| II-20 | H | Cl | H | 4-Cl—Ph | —O—$CH_2$—$CF_3$ | $CH_3$ | 160 | α + β mixture |
| II-21 | H | $CH_3$ | $CH_3$ | $CH_3$ | —O—$CH_2$—$CF_3$ | $CH_3$ | 153 | α + β mixture |
| II-22 | $CH_3$ | $CH_3$ | Cl | H | —O—$CH_2$—$CF_2$—$CF_3$ | $CH_3$ | oil | α + β mixture |
| II-23 | H | $CH_3$ | H | $CH_3$ | —O—$CH_2$—$CF_2$—$CF_3$ | $CH_3$ | oil | α + β mixture |
| II-24 | H | $CH_3$ | H | 4-F—Ph | —O—$CH_2$—$CF_3$ | $CH_3$ | 116 | α + β mixture |
| II-25 | $C_2H_5$ | Br | $CH_3$ | H | —O—$CH_2$—$CF_2$—$CF_3$ | $CH_3$ | 116 | α + β mixture |

Example XVI-1

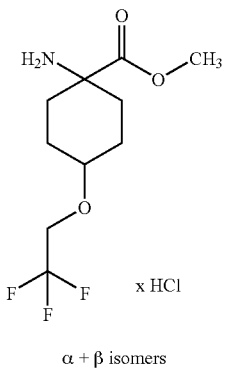 [SMILES: COC(=O)C1(N)CCC(OCC(F)(F)F)CC1]

α + β isomers

Under argon, 43 g of the compound of Example XIX-1 are initially charged in 500 ml of methanol, and 15 ml (0.205 mol) of thionyl chloride are slowly added dropwise at 0-5° C. The mixture is stirred at 0° C. for 30 min and then at 40° C. for 24 h. The solution is cooled to 5° C. The precipitate is filtered off with suction and the solvent is removed on a rotary evaporator. The residue is triturated with methyl tert-butyl ether and the precipitate is filtered off with suction. The product is precipitated from methylene chloride/n-hexane.

Yield starting from 4-trifluoroethoxycyclohexanone: 37 g (=95% of theory), m.p. 176° C. about 1:2 α+β isomers The following examples of the formula (XVI) where $Q^1$ and $Q^2$=H and m=1 are obtained analogously to Example XVI-1

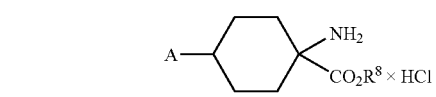
(XVI)

| Ex. No. | A | $R^8$ | $^1$H-NMR (ppm) (400 MHz, $d_6$-DMSO) | Isomer |
|---|---|---|---|---|
| XVI-2 | O—CH$_2$—CF$_2$—CF$_3$ | CH$_3$ | 3.74, 3.75 (s, 3H, OC$\underline{H}_3$) 4.08, 4.15 (tm, 2H, O—C$\underline{H}_2$—CF$_2$) | α + β |
| XVI-3 | O—CH$_2$—CF$_2$—CHF$_2$ | CH$_3$ | 3.75, 3.76 (s, 3H, OC$\underline{H}_3$) 3.87-3.95 (tm, 2H, O—C$\underline{H}_2$—CF$_2$) 6.27-6.73 (qm, 1, CF$_2$—C$\underline{H}$F$_2$) | α + β |

Example XIX-1

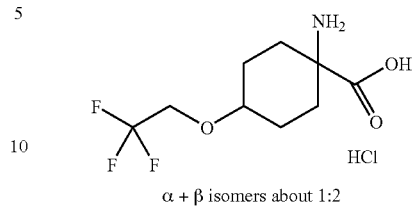

α + β isomers about 1:2

Under argon, 41.5 g of the compound of Example XXIII-1 are suspended in 250 ml of 30% strength KOH. The mixture is stirred under reflux (nitrogen) for 24 h. The mixture is concentrated to about 25% of its original volume, at 0-10° C. adjusted to pH 5 using conc. HCl, the water is removed using a rotary evaporator and the precipitate is dried. The crude product is reacted without additional purification.

The following compounds of the formula (XIX) where $Q^1$ and $Q^2$=H and m=1 are obtained analogously to Example XIX-1

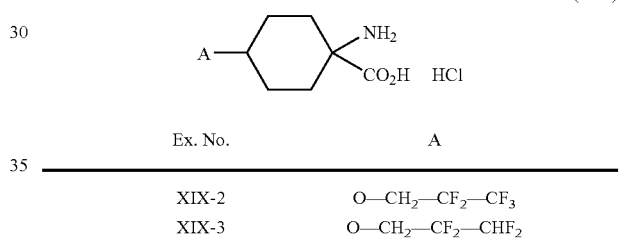
(XIX)

| Ex. No. | A |
|---|---|
| XIX-2 | O—CH$_2$—CF$_2$—CF$_3$ |
| XIX-3 | O—CH$_2$—CF$_2$—CHF$_2$ |

Example XXIII-1

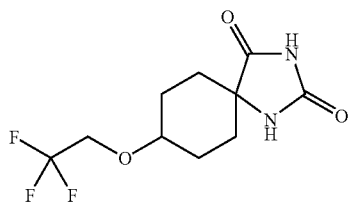

α + β isomers about 1:2

270 ml of water, 64 g (0.666 mol) of ammonium carbonate and 7.15 g (0.146 mol) of sodium cyanide are initially charged under argon. 26 g (0.1325 mol) of 4-trifluoroethoxy-cyclohexanone are added dropwise at 20° C. The reaction mixture is stirred at 55° C. to 60° C. for 24 h, then at 0° C. to 5° C. for 2 h. The solid is filtered off with suction, washed with the mother liquor and dried. The crude product is reacted without additional purification.

The following compounds of the formula (XXIII) where $Q^1$ and $Q^2$=H and m=1 are obtained analogously to Example XXIII-1

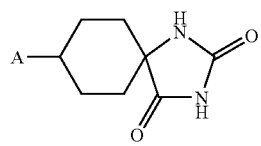

(XXIII)

| Ex. No. | A | ¹H-NMR (ppm) (400 MHz, d₆-DMSO) | Isomer |
|---|---|---|---|
| XXIII-2 | O—CH₂—CF₂—CF₃ | 3.49-3.56; 3.63-3.68 (2m, 1H, CH—OCH₂CF₂) 4.03-4.14 (qm, 2H, OCH₂—CF₂) | α + β |
| XXIII-3 | O—CH₂—CF₂—CHF₂ | 3.45-3.51; 3.63 (2m, 1H, CH—OCH₂CF₂) 3.85-3.96 (qm, 2H, O—CH₂—CF₂) 6.24-6.54 (tm, 1H, CF₂—CHF₂) 8.12, 8.17 (2sb, 1H, NH) | α + β 1:2 |

Preparation of 4-trifluoroethoxycyclohexanone

Step 1

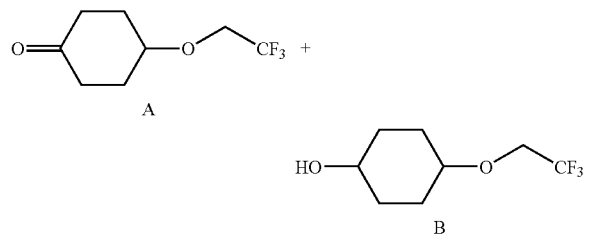

Under nitrogen, 53 g (0.276 mol) of 4-trifluoroethoxyphenol are initially charged in 420 ml of methylcyclohexane, and 0.3 g (0.8 mmol) of borax and the catalyst (5% Pd/C, 6 g) are added. A hydrogen pressure of 50 bar is applied, and the reaction mixture is heated to 160° C. The hydrogen pressure is then increased to 100 bar, and hydrogenation is continued until nearly all of the starting material has been converted. After emptying, the autoclave is carefully rinsed with dichloromethane, the combined organic phases are filtered through Celite 545 and the filter cake is washed with 500 ml of dichloromethane. The filtrate is concentrated at a water bath temperature of at most 40° C. and 78 mbar.

Yield: This gives 51 g of a light-pink liquid comprising about 31% 4-trifluoroethoxycyclohexanone, about 51% of 4-trifluoroethoxycyclohexanol and about 14% of methylcyclohexane. Without further purification, the crude product is oxidized with pyridinium dichromate.

Step 2

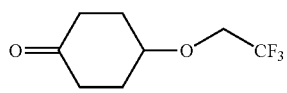

100 g of molecular sieves and 105.25 g (0.28 mol) of finely powdered pyridinium dichromate are suspended in 450 ml of dichloromethane, and 51 g of the mixture from step 1 in about 50 ml of dichloromethane are added dropwise. With monitoring by gas chromatography, the reaction mixture is stirred at room temperature for 18 h. After the reaction has ended, (550 ml) of diethyl ether is added and the mixture is filtered through Celite. The filter cake is washed with diethyl ether. The filtrate is washed with 1N HCl (3×250 ml), water (200 ml) and saturated NaCl solution (200 ml) and dried. The solvent is carefully removed at 35° C. and 60 mbar. The residue is distilled under reduced pressure.

Yield: 24 g (b.p.₁₇ 102-104° C.)

Example (I-2-a-1)

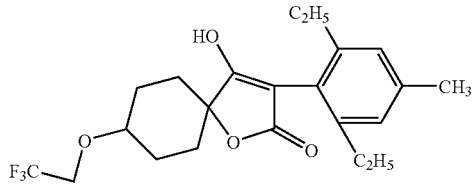 [SMILES: CCc1cc(C)cc(CC)c1C1=C(O)C2(CCC(OCC(F)(F)F)CC2)OC1=O]

1.081 g (4 mmol) of ethyl 4-trifluoroethoxy-1-hydroxycyclohexanecarboxylate (XXII-1) and 0.899 g (4 mmol) of 2,6-diethyl-4-methylphenylacetyl chloride are heated at 120° C. for 8 h, cooled, divided between methyl tert-butyl ether (MTBE) and 5% strength aqueous sodium hydroxide solution, the phases are separated, and the organic phase is dried and concentrated on a rotary evaporator. This gives 1.6 g of product which is initially charged in 30 ml of N,N-dimethylformamide, 0.59 g of potassium tert-butoxide are added and the mixture is stirred at room temperature overnight. The reaction mixture is stirred into water and extracted with MTBE, the aqueous phase is acidified with hydrochloric acid and extracted with methylene chloride and the extract is dried and concentrated on a rotary evaporator.

Yield: 1.4 g (=92% of theory) isomer mixture α+β about 1:1, log P α 3.78; β 3.64

The following compounds of the formula (I-2-a) where $Q^1$ and $Q^2$=H and m=1 are obtained analogously to Example (I-1-a-2) and following the general preparation instructions:

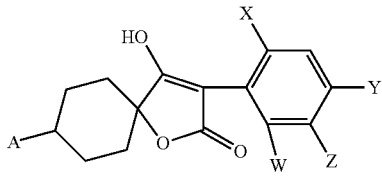

(I-2-a)

| Ex. No. | W | X | Y | Z | A | log P | Isomer |
|---|---|---|---|---|---|---|---|
| I-2-a-2 | H | CH₃ | H | CH₃ | —O—CH₂—CF₃ | α 3.10 β 2.95 | α + β about 1:1 |
| I-2-a-3 | CH₃ | CH₃ | CH₃ | H | —O—CH₂—CF₃ | α 3.31 β 3.18 | α + β about 1:1 |
| I-2-a-4 | H | CH₃ | CH₃ | CH₃ | —O—CH₂—CF₃ | α 3.34 β 3.20 | α + β about 1:1 |
| I-2-a-5 | CH₃ | C₂H₅ | CH₃ | H | —O—CH₂—CF₃ | α 3.54 β 3.41 | α + β about 1:1 |
| I-2-a-6 | CH₃ | CH₃ | H | 4-Cl—Ph | —O—CH₂—CF₃ | α 4.29 β 4.13 | α + β about 1:1 |
| I-2-a-7 | H | CH₃ | H | 4-Cl—Ph | —O—CH₂—CF₃ | α 4.09 α 3.93 | α + β about 1:1 |
| I-2-a-8 | CH₃ | CH₃ | Cl | H | —O—CH₂—CF₃ | α 3.39 β 3.25 | α + β about 1:1 |
| I-2-a-9 | CH₃ | CH₃ | CH₃ | H | —O—CH₂—CF₃ | 3.29 | α* |
| I-2-a-10 | CH₃ | CH₃ | CH₃ | H | —O—CH₂—CF₃ | 3.16 | β* |
| I-2-a-11 | CH₃ | OCH₃ | CH₃ | H | —O—CH₂—CF₃ | α 3.07 β 2.94 | α + β about 1:1 |
| I-2-a-12 | CH₃ | C₂H₅ | 4-Cl—Ph | H | —O—CH₂—CF₃ | α 4.51 β 4.36 | α + β about 1:1 |

*isolated by preparative HPLC

Example (I-2-b-1)   α-Isomer

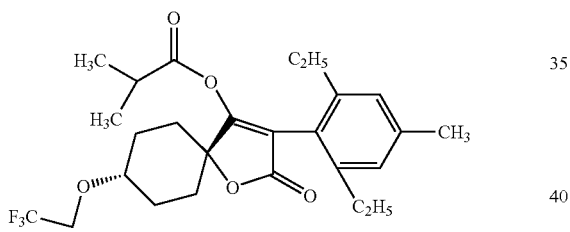

Example (I-2-b-2)   β-Isomer

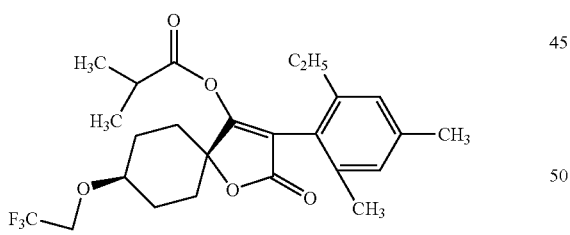

At room temperature, 0.062 g (0.582 mmol) of isobutyryl chloride in methyl chloride are added to 0.2 g (0.485 mmol) of the compound of Example (I-2-a-1) and 0.06 g (0.582 mmol) of triethylamine in 10 ml of methylene chloride, and the mixture is stirred at room temperature overnight. The reaction mixture is concentrated and the residue is separated by preparative HPLC on RP18 silica gel using an acetonitrile/water gradient (0.05% formic acid) 50:50→100:0 over 20 min.

Yield:

59 mg=24% of theory (I-2-b-1), log P 5.69 and 72 mg=30% of theory (I-2-b-2), log P 5.40

The following compounds of the formula (I-2-b) where $Q^1$ and $Q^2$=H and m=1 are obtained analogously to Examples (I-2-b-1) and (I-2-b-2) and following the general preparation instructions:

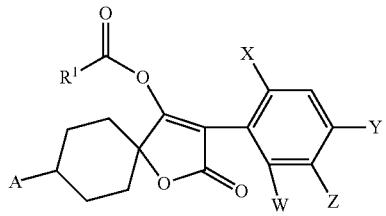

(I-2-b)

| Ex. No. | W | X | Y | Z | A | R¹ | log P | Isomer |
|---|---|---|---|---|---|---|---|---|
| I-2-b-3 | CH₃ | C₂H₅ | CH₃ | H | —O—CH₂—CF₃ | i-C₃H₇ | 5.44 | α |
| I-2-b-4 | CH₃ | C₂H₅ | CH₃ | H | —O—CH₂—CF₃ | i-C₃H₇ | 5.15 | β |
| I-2-b-5 | H | CH₃ | H | CH₃ | —O—CH₂—CF₃ | i-C₃H₇ | 4.88 | α |
| I-2-b-6 | H | CH₃ | H | CH₃ | —O—CH₂—CF₃ | i-C₃H₇ | 4.62 | β |
| I-2-b-7 | H | CH₃ | CH₃ | CH₃ | —O—CH₂—CF₃ | i-C₃H₇ | 5.14 | α |
| I-2-b-8 | H | CH₃ | CH₃ | CH₃ | —O—CH₂—CF₃ | i-C₃H₇ | 4.87 | β |
| I-2-b-9 | CH₃ | CH₃ | CH₃ | H | —O—CH₂—CF₃ | i-C₃H₇ | 5.14 | α |
| I-2-b-10 | CH₃ | CH₃ | CH₃ | H | —O—CH₂—CF₃ | i-C₃H₇ | 4.88 | β |
| I-2-b-11 | CH₃ | CH₃ | H | 4-Cl—Ph | —O—CH₂—CF₃ | i-C₃H₇ | 6.11 | α |
| I-2-b-12 | CH₃ | CH₃ | H | 4-Cl—Ph | —O—CH₂—CF₃ | i-C₃H₇ | 5.83 | β |
| I-2-b-13 | H | CH₃ | H | 4-Cl—Ph | —O—CH₂—CF₃ | i-C₃H₇ | 5.84 | α |
| I-2-b-14 | H | CH₃ | H | 4-Cl—Ph | —O—CH₂—CF₃ | i-C₃H₇ | 5.55 | β |
| I-2-b-15 | CH₃ | CH₃ | Cl | H | —O—CH₂—CF₃ | i-C₃H₇ | 5.25 | α |
| I-2-b-16 | CH₃ | CH₃ | Cl | H | —O—CH₂—CF₃ | i-C₃H₇ | 4.97 | β |
| I-2-b-17 | CH₃ | C₂H₅ | 4-Cl—Ph | H | —O—CH₂—CF₃ | i-C₃H₇ | 6.33 | α |
| I-2-b-18 | CH₃ | C₂H₅ | 4-Cl—Ph | H | —O—CH₂—CF₃ | i-C₃H₇ | 6.02 | β |
| I-2-b-19 | CH₃ | OCH₃ | CH₃ | H | —O—CH₂—CF₃ | i-C₃H₇ | 4.72 | α |
| I-2-b-20 | CH₃ | OCH₃ | CH₃ | H | —O—CH₂—CF₃ | i-C₃H₇ | 4.48 | β |

Ph = phenyl

Determination of the Log P Values (LC/MS, HCOOH Method):

The log P values given in the tables were determined in accordance with EEC Directive 79/831 Annex V.A8 by HPLC (High Performance Liquid Chromatography) using a reversed-phase column (C 18). Temperature: 55° C.

Mobile phases for determination in the acidic range (pH 3.4):

Mobile phase A: acetonitrile+1 ml formic acid/liter. Mobile phase B: water+0.9 ml formic acid/liter. Gradient: from 10% mobile phase A/90% mobile phase B to 95% mobile phase A/5% mobile phase B over 4.25 min. Calibration was carried out using unbranched alkan-2-ones (having 3 to 16 carbon atoms) with known log P values (determination of the log P values by the retention times using linear interpolation between two successive alkanones). The lambda max values were determined in the maxima of the chromatographic signals using the UV spectra from 200 nm to 400 nm.

Precursor for Example (XXII-1)

1-Hydroxy-4-trifluoroethoxycyclohexanecarbonitrile

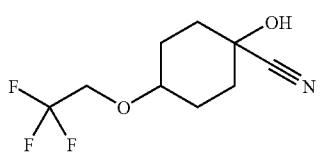 [SMILES: N#CC1(O)CCC(OCC(F)(F)F)CC1]

13.74 g of sodium cyanide are dissolved in 200 ml of water. Over a period of 30 min, 50 g of 4-trifluoroethoxycyclohexanone are then added dropwise at 20-28° C. with slight cooling. The mixture is stirred at 25° C. for 5 minutes, and 31.48 g of sodium disulfite, dissolved in 100 ml of water, are then added dropwise with cooling at 25-30° C. over a period of 30 min. With monitoring by thin-layer chromatography, the mixture is stirred at room temperature. The aqueous phase is extracted 3× with in each case 90 ml of toluene. The organic phases are combined and concentrated under reduced pressure.

Yield: 32.52 g

Example (XXII-1)

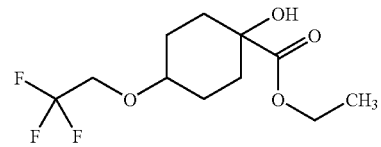 [SMILES: CCOC(=O)C1(O)CCC(OCC(F)(F)F)CC1]

24 g of 1-hydroxy-4-trifluoroethoxycyclohexanecarbonitrile are dissolved in 150 ml of ethanol. HCl gas is introduced at −20° C. The cooling bath is allowed to thaw slowly (end at −5° C.), duration of HCl introduction about 2 h. The mixture is stirred without cooling overnight. Ethanol is distilled off at 45° C. 150 ml of ice-water are added to the residue, and the mixture is stirred at room temperature for 3 hours. The reaction mixture is extracted 3× with in each case 150 ml of methylene chloride. The combined methylene chloride phases are washed with 200 ml of saturated sodium bicarbonate solution and concentrated. Distillation is carried out under high vacuum using a column (estimated boiling point at 8·10⁻² mbar: ~85° C.).

Yield: 25.6 g

USE EXAMPLES

Example No. 1

Phaedon Test

Spray Treatment

| Solvent: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (Brassica pekinensis) are sprayed with an active compound preparation of the desired concentration and, after drying, populated with larvae of the mustard beetle (Phaedon cochleariae).

After the desired period of time, the effect in % is determined. 100% means that all beetle larvae have been killed; 0% means that none of the beetle larvae have been killed.

In this test, for example, the following compounds of the Preparation Examples show, at an application rate of 100 g/ha, an effect of ≧80%:

Ex. Nos. I-1-a-1, I-1-b-1, I-2-a-4, I-2-b-6

In this test, for example, the following compounds of the Preparation Examples show, at an application rate of 500 g/ha, an effect of ≧80%:

Ex. Nos. I-1-a-2, I-1-a-3, I-1-a-5, I-1-a-6, I-1-a-7, I-1-a-8, I-1-a-9, I-1-a-12, I-1-a-13, I-1-a-15, I-1-a-16, I-1-a-17, I-1-a-18, I-1-a-19, I-1-a-20, I-1-a-21, I-1-a-22, I-1-a-23, I-1-a-24, I-1-a-25, I-1-a-26, I-1-a-27, I-1-a-28, I-1-a-29, I-1-a-30, I-1-b-2, I-1-b-3, I-1-c-1, I-1-c-2, I-1-c-3, I-2-a-1, I-2-a-2, I-2-a-3, I-2-a-5, I-2-a-6, I-2-a-8, I-2-a-9, I-2-a-10, I-2-a-11, I-2-a-12, I-2-a-7, I-2-a-8, I-2-b-3, I-2-b-9, I-2-b-10, I-2-b-11, I-2-b-12, I-2-b-13, I-2-b-14, I-2-b-15, I-2-b-5, I-2-b-8, I-2-b-16

Example No. 2

Myzus Test

MYZUPE Spray Treatment

| Solvent: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (Brassica pekinensis) infested by all stages of the green peach aphid (Myzus persicae) are sprayed with an active compound preparation of the desired concentration.

After the desired period of time, the effect in % is determined. 100% means that all the aphids have been killed; 0% means that none of the aphids have been killed.

In this test, for example, the following compounds of the Preparation Examples show, at an application rate of 500 g/ha, an effect of ≧80%:

Ex. Nos. I-1-a-1, I-1-a-2, I-1-a-3, I-1-a-5, I-1-a-6, I-1-a-7, I-1-a-8, I-1-a-9, I-1-a-10, I-1-a-11, I-1-a-23, I-1-a-24, I-1-a-25, I-1-a-26, I-1-a-27, I-1-a-28, I-1-a-29, I-1-a-30, I-1-b-2, I-1-b-3, I-1-c-1, I-1-c-2, I-1-c-3, I-2-a-1, I-2-a-2, I-2-a-3, I-2-a-4, I-2-a-5, I-2-a-6, I-2-a-8, I-2-a-9, I-2-a-10, I-2-a-11, I-2-a-12, I-2-b-4, I-2-b-5, I-2-b-8, I-2-b-10, I-2-b-11, I-2-b-12, I-2-b-14, I-2-b-15, I-2-b-16

In this test, for example, the following compounds of the Preparation Examples show, at an application rate of 100 g/ha, an effect of ≧80%:

Ex. Nos. I-1-b-1, I-2-b-6, I-1-a-17

Example No. 3

Tetranychus Test

OP-Resistant (TETRUR Spray Treatment)

| Solvent: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of bean leaves (Phaseolus vulgaris) which are infested by all stages of the greenhouse red spidermite (Tetranychus urticae) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 100 g/ha, an effect of ≧80%: see table Ex. Nos. I-1-a-1, I-1-a-2, I-1-a-3, I-1-a-4, I-1-a-5, I-1-a-6, I-1-a-7, I-1-a-8, I-1-a-9, I-1-a-11, I-1-a-12, I-1-a-16, I-1-a-20, I-1-a-22, I-1-a-23, I-1-a-24, I-1-a-25, I-1-a-29, I-1-a-30, I-1-b-2, I-1-b-3, I-1-c-1, I-1-c-2, I-1-c-3, I-2-a-6, I-2-a-7, I-2-a-8, I-2-a-9, I-2-a-10, I-2-a-11, I-2-a-12, I-2-b-3, I-2-b-4, I-2-b-7, I-2-b-8, I-2-b-10, I-2-b-11, I-2-b-13, I-2-b-14, I-2-b-15

Example No. 4

Spodoptera frugiperda Test

SPODFR Spray Treatment

| Solvent: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of corn leaves (*Zea mays*) are sprayed with an active compound preparation of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show, at an application rate of 500 g/ha, an effect of ≧80%:

Ex. Nos. I-1-a-3, I-1-a-6, I-1-a-9, I-1-a-11, I-1-a-19, I-1-a-25, I-1-a-27, I-1-a-29, I-1-b-1, I-1-b-2, I-2-a-3, I-2-a-6, I-2-a-10, I-2-b-10, I-2-b-11, I-2-b-12

Example No. 5

*Boophilus microplus* Test

BOOPMI Injection

| Solvent: | dimethyl sulfoxide |
|---|---|

To prepare a suitable active compound preparation, 1 part by weight of active compound is mixed with the stated amount of solvent, and the concentrate is diluted with water to the desired concentration.

The solution of active compound is injected into the abdomen (*Boophilus microplus*), and the animals are transferred into dishes and kept in a climatised room. The activity is assessed by oviposition of fertile eggs.

After the desired period of time, the effect in % is determined. 100% means that none of the ticks have laid any fertile eggs.

In this test, for example, the following compounds of the Preparation Examples show, at an application rate of 20 μg/animal, an effect of ≧80%:

Ex. Nos. I-1-a-1, I-1-a-2, I-1-a-3, I-1-a-5, I-1-a-8, I-1-a-9, I-1-b-1, I-1-b-2, I-1-c-1, I-1-c-2

Example No. 6

*Lucilia Cuprina* Test

LUCICU

| Solvent: | dimethyl sulfoxide |
|---|---|

To prepare a suitable active compound preparation, 1 part by weight of active compound is mixed with the stated amount of solvent, and the concentrate is diluted with water to the desired concentration.

Vessels containing horse meat treated with the active compound preparation of the desired concentration are populated with *Lucilia cuprina* larvae.

After the desired period of time, the kill in % is determined. 100% means that all of the larvae have been killed; 0% means that none of the larvae have been killed.

In this test, for example, the following compounds of the Preparation Examples show, at an application rate of 100 ppm, an effect of ≧80%:

Ex. Nos. I-1-a-1, I-1-a-3, I-1-a-5, I-1-a-6, I-1-a-8, I-1-a-9, I-1-b-1, I-1-b-2, I-1-c-1, I-1-c-2

Example No. 7

*Meloidogyne* Test

MELGIN Spray Treatment

| Solvent: | 80 parts by weight of acetone |
|---|---|

To prepare a suitable active compound preparation, 1 part by weight of active compound is mixed with the stated amount of solvent, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal action is determined in % by the gall formation. 100% means that no galls have been found; 0% means that the number of galls on the treated plants corresponds to that of the untreated control.

In this test, for example, the following compounds of the Preparation Examples show, at an application rate of 20 ppm, an effect of ≧80%:

Ex. Nos. I-1-a-3, I-1-a-7

Example No. 8

Enhancement of Activity by Ammonium/Phosphonium Salts

*Myzus persicae* Test

| Solvent: | 7 parts by weight of dimethylformamide |
|---|---|
| Emulsifier: | 2 part by weight of alkylaryl polyglycol ether |

To produce a suitable preparation of active compound, 1 part by weight of active compound is mixed with the stated amounts of solvent and emulsifier, and the concentrate is diluted with water to the desired concentration. For application with ammonium or phosphonium salts, these are added to the spray liquor in a concentration of 1000 ppm.

Bell pepper plants (*Capsicum annuum*) which are heavily infested by the green peach aphid (*Myzus persicae*) are treated by spraying to runoff point with the active compound preparation of the desired concentration. After the desired period of time, the kill in % is determined. 100% means that all animals have been killed; 0% means that none of the animals have been killed.

| Active compound | Active compound ppm | Kill rate/% after 6 days | +AS (1000 ppm) |
|---|---|---|---|
| I-1-a-5 | 4 | 5 | 99 |

Example No. 9

*Aphis gossypii* Test

| Solvent: | 7 parts by weight of dimethylformamide |
|---|---|
| Emulsifier: | 2 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration. For application with ammonium or phosphonium salts, these are added to the spray liquor in a concentration of 1000 ppm.

Cotton plants (*Gossypium hirsutum*) which are heavily infested by the cotton aphid (*Aphis gossypii*) are treated by spraying to runoff point with the active compound preparation of the desired concentration.

After the desired period of time, the kill in % is determined. 100% means that all the aphids have been killed; 0% means that none of the aphids have been killed.

| Active compound | Active compound ppm | Kill rate/% after 6 days | +AS (1000 ppm) |
|---|---|---|---|
| I-1-a-1 | 4 | 25 | 95 |

Example No. 10

Enhancement of Activity by Ammonium/Phosphonium Salts in Combination with Penetrants

*Myzus persicae* Test

| Solvent: | 7 parts by weight of dimethylformamide |
|---|---|
| Emulsifier: | 2 part by weight of alkylaryl polyglycol ether |

To produce a suitable preparation of active compound, 1 part by weight of active compound is mixed with the stated amounts of solvent and emulsifier, and the concentrate is diluted with water to the desired concentration. For application with ammonium or phosphonium salts and penetrants (rapeseed oil methyl ester 500 EW) these are added to the spray liquor in each case in a concentration of 1000 ppm.

Bell pepper plants (*Capsicum annuum*) which are heavily infested by the green peach aphid (*Myzus persicae*) are treated by spraying to runoff point with the active compound preparation of the desired concentration. After the desired period of time, the kill in % is determined. 100% means that all animals have been killed; 0% means that none of the animals have been killed.

| Active compound | Concentration/ ppm | Kill rate/% after 6 days | | |
|---|---|---|---|---|
| | | +AS (1000 ppm) | +RME (1000 ppm) | +RME + AS (1000 ppm each) |
| I-1-a-1 | 4 | 95 | 90 | 99 | 100 |
| I-1-a-1 | 0.8 | 0 | 0 | 0 | 95 |

Example No. 11

*Aphis gossypii* Test

| Solvent: | 7 parts by weight of dimethylformamide |
|---|---|
| Emulsifier: | 2 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration. For application with ammonium or phosphonium salts and penetrants (rapeseed oil methyl esters 500 EW) these are added to the spray liquor in each case in a concentration of 1000 ppm.

Cotton plants (*Gossypium hirsutum*) which are heavily infested by the cotton aphid (*Aphis gossypii*) are treated by spraying to runoff point with the active compound preparation of the desired concentration.

After the desired period of time, the kill in % is determined. 100% means that all the aphids have been killed; 0% means that none of the aphids have been killed.

| Active compound | Concentration/ ppm | Kill rate/% after 6 days | | |
|---|---|---|---|---|
| | | +AS (1000 ppm) | +RME (1000 ppm) | +RME + AS (1000 ppm each) |
| I-1-a-3 | 20 | 25 | 5 | 10 | 90 |
| I-1-a-3 | 4 | 0 | 0 | 5 | 25 |

Example No. 12

*Heliothis virescens* Test

Treatment of Transgenic Plants

| Solvent: | 7 parts by weight of acetone |
|---|---|
| Emulsifier: | 1 parts by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soybean shoots (Glycine max) of the cultivar Roundup Ready (trade name of Monsanto Comp. USA) are treated by being dipped into the preparation of active compound of the desired concentration and are populated with the tobacco bud worm Heliothis virescens while the leaves are still moist.

After the desired period of time, the kill of the insects is determined.

Example No. 13

Critical Concentration Test/Soil Insects

Treatment of Transgenic Plants

| Test insect: | Diabrotica balteata - larvae in soil |
|---|---|
| Solvent: | 7 parts by weight of acetone |
| Emulsifier: | 1 parts by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually irrelevant, only the amount by weight of active compound per volume unit of soil, which is stated in ppm (mg/l) matters. The soil is filled into 0.25 l pots and these are allowed to stand at 20° C.

Immediately after preparation, 5 pre-germinated corn corms of the cultivar YIELD GUARD (trade mark of Monsanto Comp., LISA) are placed into each pot. After 2 days, the test insects in question are placed into the treated soil. After a further 7 days, the efficacy of the active compound is determined by counting the corn plants that have emerged (1 plant=20% efficacy).

Example No. 14

1. Herbicidal Pre-Emergence Action

Seeds of monocotyledonous and dicotyledonous weed and crop plants are placed in sandy loam in wood fiber pots and covered with soil. The test compounds, formulated in the form of wettable powders (WP) are then, as an aqueous suspension with a water application rate of 600 l/ha (converted), with 0.2% of wetting agent added, applied at various dosages to the surface of the covering soil.

After the treatment, the pots are placed in a greenhouse and kept under good growth conditions for the test plants. The visual assessment of the emergence damage to the test plants is carried out after a trial period of 3 weeks by comparison with untreated controls (herbicidal activity in percent: 100% activity=the plants have died, 0% activity=like control plants).

In addition to the compounds mentioned above, the following compounds show a pre-emergence action of ≧80% against Lolium multiflorum and Setaria viridis at 320 g/ha of a.i.: I-1-a-1, I-1-a-2, I-1-a-4, I-1-a-5, I-1-a-7, I-1-a-8, I-1-a-9, I-1-a-12, I-1-a-13, I-1-a-14, I-1-b-1, I-1-b-3, I-1-c-1, I-1-c-2, I-1-c-3.

2. Herbicidal Post-Emergence Action

Seeds of monocotyledonous and dicotyledonous weed and crop plants are placed in sandy loam in wood fiber pots, covered with soil and cultivated in a greenhouse under good growth conditions. 2 to 3 weeks after sowing, the test plants are treated at the one-leaf stage. The test compounds, formulated as wettable powders (WP) are then, with a water application rate of 600 l/ha (converted), with 0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (herbicidal activity in percent: 100% activity=the plants have died, 0% activity=like control plants).

In addition to the compounds mentioned above, the following compounds show a post-emergence action of ≧80% against Echinocloa crus-galli, Lolium multiflorum and Setaria viridis at 80 g/ha: I-1-a-2, I-1-a-4, I-1-a-5, I-1-a-7, I-1-a-9, I-1-a-12, I-1-a-13, I-1-a-14, I-1-b-3.

Use of Safeners:

If it is additionally to be tested as to whether safeners can improve the plant compatibility of test substances in the case of crop plants, the following options are used for applying the safeners:
- seeds of the crop plants are, before sowing, dressed with the safener substance (the amount of safener stated in percent, based on the weight of the seed)
- before application of the test substances, the crop plants are sprayed with the safener at a certain application rate per hectare (usually 1 day before the application of the test substances)
- the safener is applied together with the test substance as a tank mix (the amount of safener stated in g/ha or as a ratio, based on the herbicide).

TABLE

| | Application rate g a.i./ha | 10 days after application Summer wheat observed (%) | 28 days after application Summer wheat observed (%) |
|---|---|---|---|
| Ex. (I-1-a-7) | 100 | 60 | 40 |
| | 50 | 60 | 30 |
| | 25 | 50 | 20 |
| | 12.5 | 40 | 10 |
| Ex. (I-1-a-7) + mefenpyr | 100 + 50 | 40 | 20 |
| | 50 + 50 | 40 | 20 |
| | 25 + 50 | 30 | 10 |
| | 12.5 + 50 | 25 | 0 |

Application of the safener 1 day prior to the herbicide

The invention claimed is:

1. A compound of the formula (I)

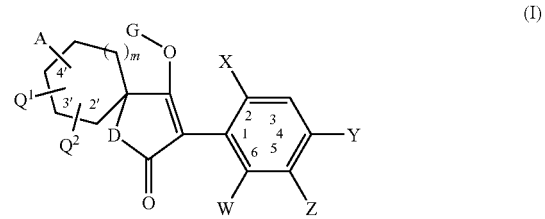

in which

W represents hydrogen, alkyl, alkenyl, alkynyl, optionally substituted cycloalkyl, halogen, alkoxy, alkenyloxy, haloalkyl, haloalkoxy or cyano, X represents halogen, alkyl, alkenyl, alkynyl, optionally substituted cycloalkyl, alkoxy, alkenyloxy, alkylthio, alkylsulfinyl, alkylsulfonyl, haloalkyl, haloalkoxy, haloalkenyloxy, nitro or cyano, Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl, A represents haloalkoxy or halocycloalkylalkoxy, D represents NH or oxygen, $Q^1$, $Q^3$ independently of one another represent hydrogen, alkyl, haloalkyl or alkoxy, m represents the number 0 or 1, G represents hydrogen (a) or one of the groups

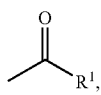 (b)

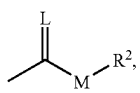 (c)

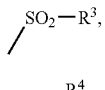 (d)

 (e)

E, or (f)

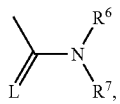 (g)

in which

E represents a metal ion or an ammonium ion,

L represents oxygen or sulfur,

M represents oxygen or sulfur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, in each case optionally halogen- or cyano-substituted alkyl, cycloalkyl, alkenyl, alkoxy, alkoxyalkyl, in each case optionally substituted phenyl or benzyl, or together with the N atom to which they are attached form an optionally substituted cycle which optionally contains oxygen or sulfur.

2. The compound of the formula (I) as claimed in claim 1 in which

W represents hydrogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents halogen, $C_1$-$C_6$-alkoxy, $C_1$-$C_4$-haloalkyl, $C_1$-$C_4$-haloalkoxy or cyano, X represents halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulfinyl, $C_1$-$C_6$-alkylsulfonyl, $C_1$-$C_6$-haloalkoxy, $C_3$-$C_6$-haloalkenyloxy, nitro or cyano, Y and Z independently of one another represent hydrogen, halogen, $C_1$-$C_6$-alkyl, $C_2$-$C_6$-alkenyl, $C_2$-$C_6$-alkynyl, represent $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represent $C_1$-$C_6$-alkoxy, $C_1$-$C_6$-haloalkyl, $C_1$-$C_6$-haloalkoxy, cyano, $C_2$-$C_6$-alkenyl, $C_1$-$C_6$-alkynyl or one of the (het) aryl radicals

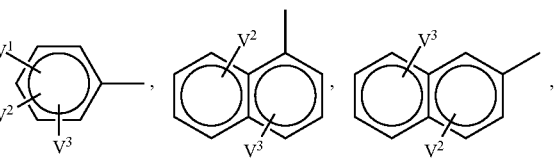

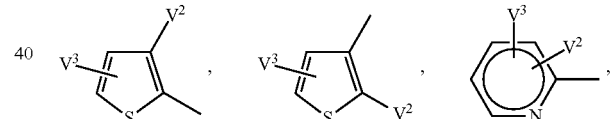

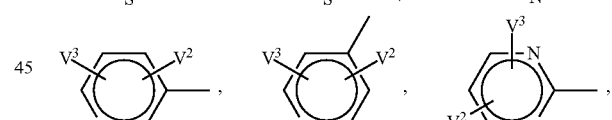

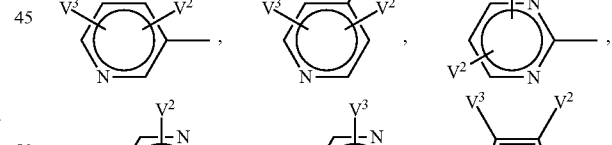

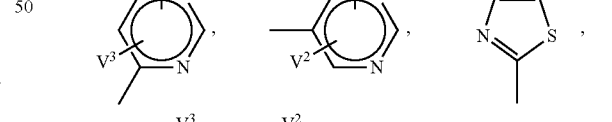

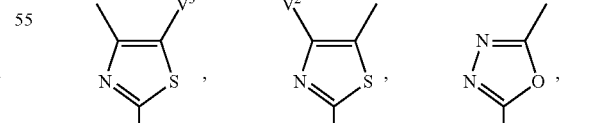

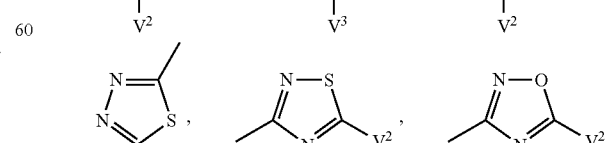

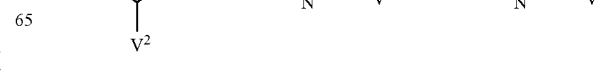

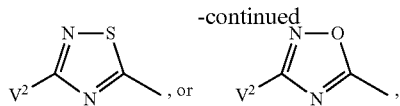

where in the case of (het)aryl only one of the radicals Y or Z may represent (het)aryl, $V^1$ represents hydrogen, halogen, $C_1$-$C_{12}$-alkyl, $C_1$-$C_6$-alkoxy, $C_1$-$C_6$-alkylthio, $C_1$-$C_4$-haloalkyl, $C_1$-$C_4$-haloalkoxy, nitro, cyano, or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally monosubstituted or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, A represents $C_1$-$C_4$-alkoxy which is mono- to heptasubstituted by fluorine, chlorine, bromine and/or iodine or represents $C_3$-$C_6$-cycloalkyl-$C_1$-$C_2$-alkoxy which is mono- to pentasubstituted by fluorine, chlorine and/or bromine and which may optionally be substituted by $C_1$-$C_2$-alkyl, $C_1$-$C_2$-haloalkyl or $C_1$-$C_2$-alkoxy, D represents NH (1) or oxygen (2), $Q^1$ and $Q^2$ independently of one another represent hydrogen, $C_1$-$C_6$-alkyl, $C_1$-$C_2$-haloalkyl or $C_1$-$C_4$-alkoxy, m represents the number 0 or 1, G represents hydrogen (a) or one of the groups

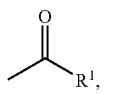
(b)

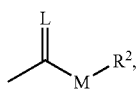
(c)

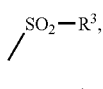
(d)

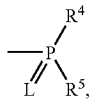
(e)

E, or (f)

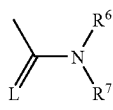
(g)

in which

E represents a metal ion or an ammonium ion,

L represents oxygen or sulfur and

M represents oxygen or sulfur, $R^1$ represents in each case optionally halogen- or cyano-substituted $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulfur, represents phenyl which is optionally substituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio or $C_1$-$C_6$-alkylsulfonyl, represents phenyl-$C_1$-$C_6$-alkyl which is optionally substituted by halogen, nitro, cyano, $C_1$-$C_6$-alkyl, $C_1$-$C_6$-alkoxy, $C_1$-$C_6$-haloalkyl or $C_1$-$C_6$-haloalkoxy, represents optionally halogen- or $C_1$-$C_6$-alkyl-substituted 5- or 6-membered hetaryl having one or two heteroatoms from the group consisting of oxygen, sulfur and nitrogen, represents phenoxy-$C_1$-$C_6$-alkyl which is optionally substituted by halogen or $C_1$-$C_6$-alkyl, represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulfur and nitrogen, $R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, or represents $C_3$-$C_8$-cycloalkyl which is optionally substituted by halogen, $C_1$-$C_6$-alkyl or $C_1$-$C_6$-alkoxy, or represents phenyl or benzyl, each of which is optionally substituted by halogen, cyano, nitro, $C_1$-$C_6$-alkyl, $C_1$-$C_6$-alkoxy, $C_1$-$C_6$-haloalkyl or $C_1$-$C_6$-halogenalkoxy, $R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulfur.

3. The compound of the formula (I) as claimed in claim 1 in which

W represents hydrogen, chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_2$-haloalkyl or $C_1$-$C_2$-haloalkoxy, X represents chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_4$-haloalkyl, $C_1$-$C_4$-haloalkoxy or cyano, Y and Z independently of one another represent hydrogen, fluorine, chlorine, bromine, $C_1$-$C_4$-alkyl, $C_2$-$C_4$-alkenyl, $C_2$-$C_4$-alkynyl, represent $C_3$-$C_6$-cycloalkyl which is optionally monosubstituted by methyl, ethyl, methoxy, fluorine, chlorine, trifluoromethyl or cyclopropyl, represents $C_1$-$C_6$-alkoxy, haloalkyl, $C_1$-$C_4$-haloalkoxy, cyano, $C_2$-$C_4$-alkenyl, $C_2$-$C_4$-alkynyl or one of the (het)aryl radicals,

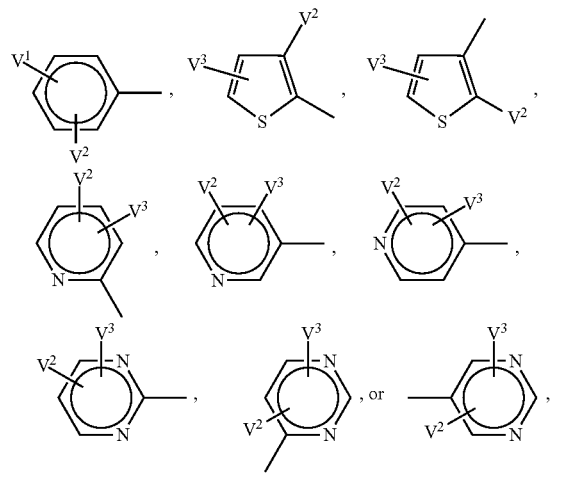

where in the case of (het)aryl only one of the radicals Y or Z may represent (het)aryl, $V^1$ represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or represents phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A represents $C_1$-$C_4$-alkoxy which is mono- to pentasubstituted by fluorine, chlorine and/or bromine or represents $C_3$-$C_6$-cycloalkyl-$C_1$-$C_2$-alkoxy which is mono- to trisubstituted by fluorine and/or chlorine, D represents NH (1) or oxygen (2), $Q^1$ and $Q^2$ independently of one another represent hydrogen, methyl, ethyl, trifluoromethyl, methoxy or ethoxy, m represents the number 0 or 1, G represents hydrogen (a) or one of the groups

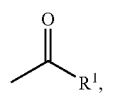 (b)

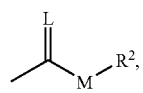 (c)

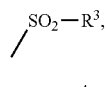 (d)

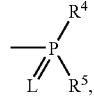 (e)

E, or (f)

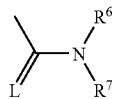 (g)

in which

E represents a metal ion or an ammonium ion,

L represents oxygen or sulfur and

M represents oxygen or sulfur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulfur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulfonyl, represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulfur.

4. The compound of the formula (I) as claimed in claim 1 in which

W represents hydrogen, chlorine, bromine, methyl, ethyl, vinyl, ethynyl, propynyl, cyclopropyl, methoxy, ethoxy or trifluoromethyl, X represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another represent hydrogen, fluorine, chlorine, bromine, methyl, ethyl, vinyl, ethynyl, propynyl, cyclopropyl, methoxy, trifluoromethyl, trifluoromethoxy, cyano or a phenyl radical,

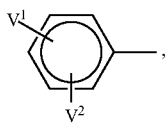

where in the case of phenyl only one of the radicals Y or Z may represent phenyl, $V^1$ represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ represents hydrogen, fluorine, chlorine, methyl, ethyl, n-propyl, isopropyl, methoxy, ethoxy or trifluoromethyl, A represents methoxy, ethoxy, propoxy, butoxy or isobutoxy, each of which is mono- to trisubstituted by fluorine and/or chlorine, or represents cyclopropylmethoxy or cyclopropylethoxy, each of which is mono- to trisubstituted by fluorine and/or chlorine, D represents NH (1) or oxygen (2), $Q^1$ and $Q^2$ represent hydrogen, m represents the number 1, G represents hydrogen (a) or one of the groups

(b)

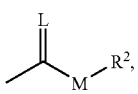
(c)

(d)

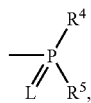
(e)

E, or
(f)

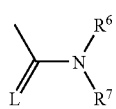
(g)

in which

E represents a metal ion or an ammonium ion,

L represents oxygen or sulfur and

M represents oxygen or sulfur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy, represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl, or represents phenyl or benzyl, each of which is optionally mono- or disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another represent hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulfur.

5. The compound of the formula (I) as claimed in claim 1 in which

W represents hydrogen, chlorine, bromine, methyl, ethyl or methoxy,

X represents chlorine, bromine, methyl, ethyl, methoxy or ethoxy,

Y and Z independently of one another represent hydrogen, chlorine, bromine, methyl, methoxy, cyclopropyl or represent the radicals

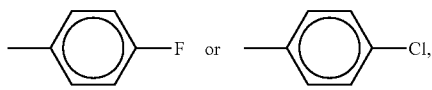 F or Cl, where in this case only one of the radicals Y or Z may represent a substituted phenyl radical, A represents methoxy, ethoxy or propoxy, each of which is mono- to trisubstituted by fluorine and/or chlorine, D represents NH (1) or oxygen (2), $Q^1$ and $Q^2$ represent hydrogen, m represents the number 1, G represents hydrogen (a) or one of the groups

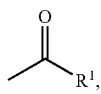 (b)

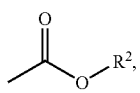 (c)

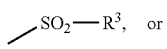 (d)

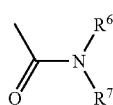 (g)

$R^1$ represents $C_1$-$C_{10}$-alkyl, $C_1$-$C_4$-alkoxy-$C_1$-$C_2$-alkyl, $C_3$-$C_6$-cycloalkyl,
represents phenyl which is optionally monosubstituted by chlorine, or represents thienyl, $R^2$ represents $C_1$-$C_{10}$-alkyl, $C_2$-$C_{10}$-alkenyl, or represents benzyl, $R^3$ represents methyl, $R^6$ and $R^7$ together represent a $C_5$-$C_6$-alkylene radical in which optionally one methylene group is replaced by oxygen or sulfur.

6. A process for the preparation of a compound of the formula (I) as claimed in claim 1, characterized in that, to obtain (A) compounds of the formula (I-1-a)

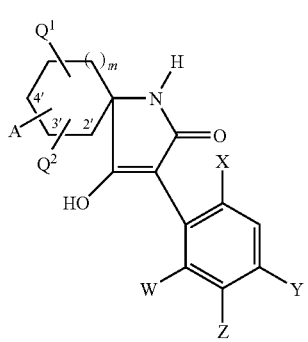 (I-1-a)

in which

A, $Q^1$, $Q^2$, m, W, X, Y and Z have the meanings given above, compounds of the formula (II)

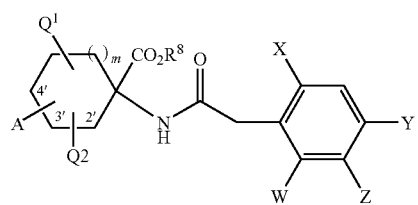 (II)

in which

A, $Q^1$, $Q^2$, m, W, X, Y and Z have the meanings given above, and $R^8$ represents alkyl, are subjected to an intramolecular condensation reaction in the presence of a diluent and in the presence of a base, (B) compounds of the formula (I-2-a)

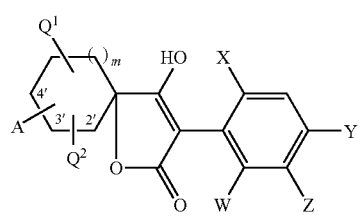 (I-2-a)

in which

A, $Q^1$, $Q^2$, m, W, X, Y and Z have the meanings given above, compounds of the formula (III)

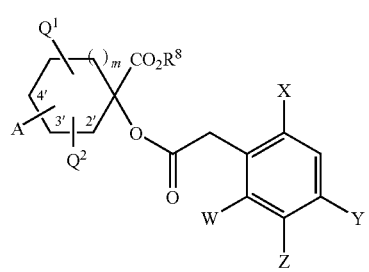 (III)

in which

A, $Q^1$, $Q^2$, m, W, X, Y, Z and $R^8$ have the meanings given above, are subjected to an intramolecular condensation reaction in the presence of a diluent and in the presence of a base, (C) compounds of the formulae (I-1-b) to (I-2-b) shown above in which $R^1$, A, $Q^1$, $Q^2$, m, W, X, Y and Z have the meanings given above, compounds of the formulae (I-1-a) to (I-2-a) in which A, $Q^1$, $Q^2$, m, W, X, Y and Z have the meanings given above are in each case α) reacted with compounds of the formula (IV)

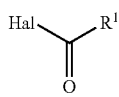

in which
R¹ the meaning given above and
Hal represents halogen
or
β) with carboxylic anhydrides of the formula (V)

R¹—CO—O—CO—R¹ (V)

in which
R¹ has the meaning given above,
if appropriate in the presence of a diluent and if appropriate in the presence of an acid binder;
(D) compounds of the formulae (I-1-c) to (I-2-c) shown above in which $R^2$, A, $Q^1$, $Q^2$, m, W, M, X, Y and Z have the meanings given above, and L represents oxygen, compounds of the formulae (I-1-a) to (I-2-a) shown above in which A, $Q^1$, $Q^2$, m, W, X, Y and Z have the meanings given above are in each case
reacted with chloroformic esters or chloroformic thioesters of the formula (VI)

R²-M-CO—Cl (VI)

in which
$R^2$ and M have the meanings given above,
if appropriate in the presence of a diluent and if appropriate in the presence of an acid binder;
(E) compounds of the formulae (I-1-c) to (I-2-c) shown above in which $R^2$, A, $Q^1$, $Q^2$, m, W, M, X, Y and Z have the meanings given above, and L represents sulfur, compounds of the formulae (I-1-a) to (I-2-a) shown above in which A, $Q^1$, $Q^2$, m, W, X, Y and Z have the meanings given above are in each case
reacted with chloromonothioformic esters or chlorodithioformic esters of the formula (VII)

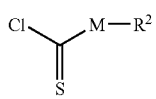

in which
M and $R^2$ have the meanings given above,
if appropriate in the presence of a diluent and if appropriate in the presence of an acid binder,
(F) compounds of the formulae (I-1-d) to (I-2-d) shown above in which $R^3$, A, W, $Q^1$, $Q^2$, m, X, Y and Z have the meanings given above, compounds of the formulae (I-1-a) to (I-2-a) shown above in which A, B, $Q^1$, $Q^2$, m, W, X, Y and Z have the meanings given above are in each case
reacted with sulfonyl chlorides of the formula (VIII)

R³—SO₂—Cl (VIII)

in which
$R^3$ has the meaning given above,
if appropriate in the presence of a diluent and if appropriate in the presence of an acid binder,
(G) compounds of the formulae (I-1-e) to (I-2-e) shown above in which L, $R^4$, $R^5$, A, $Q^1$, $Q^2$, m, W, X, Y and Z have the meanings given above, compounds of the formulae (I-1-a) to (I-2-a) shown above in which A, $Q^1$, $Q^2$, m, W, X, Y and Z have the meanings given above are in each case reacted with phosphorus compounds of the formula (IX)

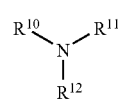

in which
L, $R^4$ and $R^5$ have the meanings given above and
Hal represents halogen
if appropriate in the presence of a diluent and if appropriate in the presence of an acid binder,
(H) compounds of the formulae (I-1-f) to (I-2-f) shown above in which E, A, $Q^1$, $Q^2$, m, W, X, Y and Z have the meanings given above, compounds of the formulae (I-1-a) to (I-2-a) in which A, $Q^1$, $Q^2$, m, W, X, Y and Z have the meanings given above are in each case
reacted with metal compounds or amines of the formulae (X) or (XI)

Me(OR¹⁰)ₜ (X)

$$R^{10}\diagdown \underset{\underset{R^{12}}{|}}{N}\diagup R^{11}$$ (XI)

in which
Me represents a monovalent or divalent, metal,
t represents the number 1 or 2 and
$R^{10}$, $R^{11}$, $R^{12}$ independently of one another represent hydrogen or alkyl,
if appropriate in the presence of a diluent,
(I) compounds of the formulae (I-1-g) to (I-2-g) shown above in which L, $R^6$, $R^7$, A, $Q^2$, M, W, X, Y and Z have the meanings given above, compounds of the formulae (I-1-a) to (I-2-a) shown above in which A, $Q^1$, $Q^2$, m, W, X, Y and Z have the meanings given above are in each case
α) reacted with isocyanates or isothiocyanates of the formula (XII)

R⁶—N=C=L (XII)

in which
$R^6$ and L have the meanings given above,
if appropriate in the presence of a diluent and if appropriate in the presence of a catalyst, or
β) reacted with carbamoyl chlorides or thiocarbamoyl chlorides of the formula (XIII)

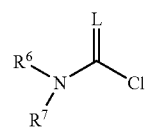

in which
L, $R^6$ and $R^7$ have the meanings given above,
if appropriate in the presence of a diluent and if appropriate in the presence of an acid binder, (Jα) compounds of the formulae (I-1-a) to (I-1-g) shown above in which A, D, G, $Q^1$, $Q^2$, m, W, X, Y and Z have the meaning given above, compounds of the formulae (I-1-a') to (I-2-g') in which A, D, G, $Q^1$, $Q^2$, m, W, X and Y have the meaning given above and Z' represents bromine or iodine

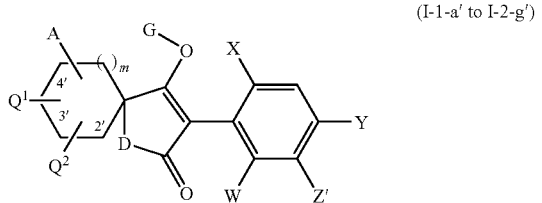
(I-1-a' to I-2-g')

and (Jβ) compounds of the formulae (I-1-a) to (I-2-g) shown above in which A, D, G, $Q^1$, $Q^2$, m, W, X, Y and Z have the meaning given above, compounds of the formulae (I-1-a″) to (I-2-g″) in which A, D, G, $Q^1$, $Q^2$, m, W, X and Z have the meaning given above and Y' represents bromine or iodine

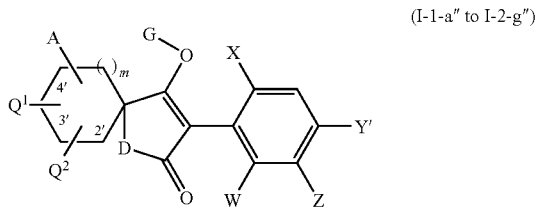
(I-1-a″ to I-2-g″)

are coupled with (het)aryl derivatives of the formulae (XVα) and (XVβ)

or esters thereof, in the presence of a solvent, in the presence of a catalyst and in presence of a base.

7. A composition for controlling pests and/or unwanted vegetation, characterized in that it comprises at least one compound of the formula (I) as claimed in claim 1.

8. A method of controlling animal pests and/or unwanted vegetation, characterized in that a compound of the formula (I) as claimed in claim 1 is allowed to act on pests, unwanted vegetation and/or their habitat.

9. A process for preparing compositions for controlling pests and/or unwanted vegetation, characterized in that a compound of the formula (I) as claimed in claim 1 is mixed with extenders and/or surfactants.

10. A composition comprising an effective amount of an active compound combination comprising, as components, (a') at least one compound of the formula (I) in which A, D, G, $Q^1$, $Q^2$, m, W, X, Y and Z have the meaning given above and (b') at least one crop plant compatibility-improving compound from the following group of compounds:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf, also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf, also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf, also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf, also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, a-(1,3-dioxolan-2-ylmethoximino)phenylacetonitrile (oxabetrinil), 2,2-dichloro-N-(1,3-dioxolan-2-ylmethyl)-N-(2-propenyl) acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl) butyric acid, 4-(4-chlorophenoxy)butyric acid, diphenylmethoxyacetic acid, methyl diphenylmethoxyacetate, ethyl diphenylmethoxyacetate, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf, also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf, also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8- oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulfonylbenzene, 1-[4-(N-2-methoxybenzoylsulfamoyephenyl]-3-methylurea (also known as N-(2-methoxybenzoyl)-4-[(methylaminocarbonyl)amino]benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclopropylamino-carbonyl)benzenesulfonamide, and/or one of the following compounds, defined by general formulae, of the general formula (IIa)

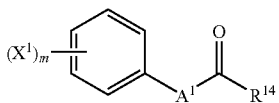

(IIa)

or of the general formula (IIb)

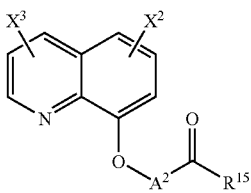

(IIb)

or of the formula (IIc)

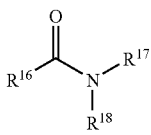

(IIc)

where m represents a number 0, 1, 2, 3, 4 or 5, $A^1$ represents one of the divalent heterocyclic groupings shown below,

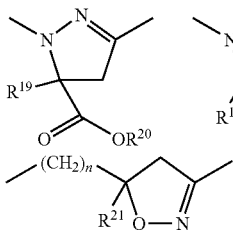

n represents a number 0, 1, 2, 3, 4 or 5, $A^2$ represents optionally $C_1$-$C_4$-alkyl- and/or $C_1$-$C_4$-alkoxycarbonyl- and/or $C_1$-$C_4$-alkenyloxycarbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

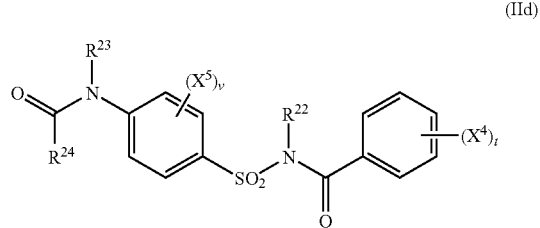

(IId)

or of the general formula (IIe)

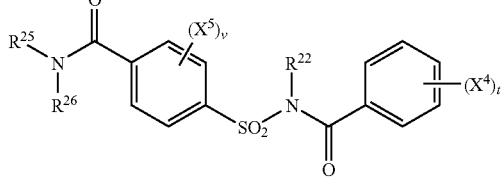

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

11. The composition as claimed in claim 10 where the crop plant compatibility-improving compound is selected from the following group of compounds:

cloquintocet-mexyl, fenchlorazole-ethyl, isoxadifen-ethyl, mefenpyr-diethyl, furilazole, fenclorim, cumyluron, dymron or the compounds

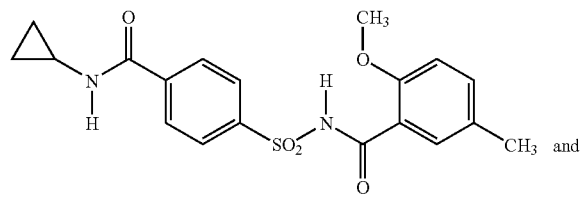

and

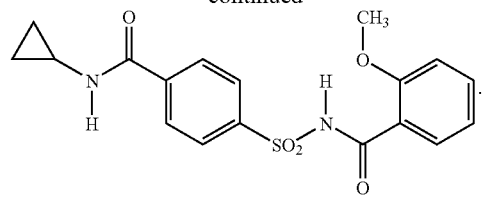

12. The composition as claimed in claim 11 where the crop plant compatibility-improving compound is cloquintocet-mexyl.

13. The composition as claimed in claim 11 where the crop plant compatibility-improving compound is mefenpyr-diethyl.

14. A method for controlling unwanted vegetation, characterized in that a composition as claimed in claim 10 is allowed to act on the plants or their surroundings.

15. A method for controlling unwanted vegetation, characterized in that a compound of the formula (I) as claimed in claim 10 and the crop plant compatibility-improving compound as set forth in claim 10 are allowed to act separately, in close temporal succession on the plants or their surroundings.

16. A composition, comprising
at least one compound of the formula (I) as claimed in claim 1 and
at least one salt of the formula (III')

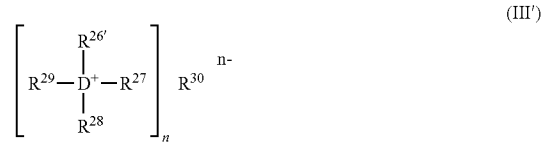

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano, n represents 1, 2, 3 or 4, $R^{30}$ represents an inorganic or organic anion.

17. The composition as claimed in claim 16, characterized in that it comprises at least one penetrant.

18. A method of increasing an activity of pesticides and/or herbicides comprising preparing a ready-to-use composition by mixing (a) an active compound of formula (I) as claimed in claim 1, (b) a salt of the formula (III')

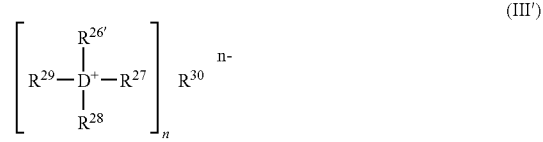

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano, n represents 1, 2, 3 or 4, $R^{30}$ represents an inorganic or organic anion, and (c) an extender.

19. The method as claimed in claim 18, further comprising:

(d) a penetrant.

* * * * *